United States Patent [19]

Chakravarty et al.

[11] Patent Number: 5,238,942

[45] Date of Patent: Aug. 24, 1993

[54] SUBSTITUTED QUINAZOLINONES BEARING ACIDIC FUNCTIONAL GROUPS AS ANGIOTENSIN II ANTAGONISTS

[75] Inventors: Prasun K. Chakravarty, Edison; William J. Greenlee, Teaneck; Nathan B. Mantlo; Arthur A. Patchett, both of Westfield; Dooseop Kim, Scotch Plains; Stephen E. de Laszlo, Atlantic Highlands; Tomasz W. Glinka, Scotch Plains, all of N.J.

[73] Assignee: Merck & Co., Inc., Rahway, N.J.

[21] Appl. No.: 867,794

[22] Filed: Apr. 16, 1992

Related U.S. Application Data

[63] Continuation-in-part of Ser. No. 698,506, May 10, 1991, abandoned.

[51] Int. Cl.[5] .................. A61K 31/505; C07D 239/84; C07D 239/72
[52] U.S. Cl. ................................. 514/259; 514/234.8; 514/260; 514/269; 514/272; 544/116; 544/119; 544/244; 544/284; 544/287; 544/293; 544/333
[58] Field of Search ............... 544/244, 284, 289, 293, 544/287, 333; 514/256, 269, 259, 260

[56] References Cited

FOREIGN PATENT DOCUMENTS

58696/90 1/1991 Australia .
407342 7/1989 European Pat. Off. .
0411766 2/1991 European Pat. Off. .

Primary Examiner—Nicholas S. Rizzo
Assistant Examiner—Y. N. Gupta
Attorney, Agent, or Firm—Valerie J. Camara; William H. Nicholson; Joseph F. DiPrima

[57] ABSTRACT

Novel substituted quinazolinones of the formula (I) are useful as angiotensin II antagonists.

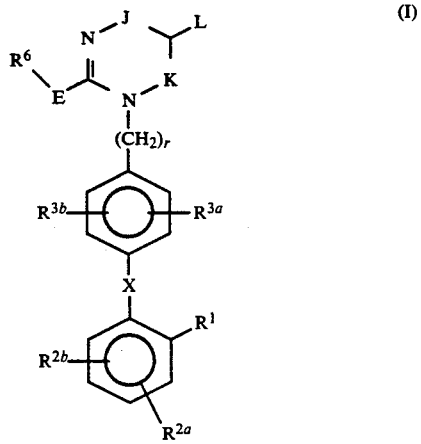

9 Claims, No Drawings

SUBSTITUTED QUINAZOLINONES BEARING ACIDIC FUNCTIONAL GROUPS AS ANGIOTENSIN II ANTAGONISTS

RELATED APPLICATION

The present patent application is a continuation-is-part of copending application Ser. No. 698,506, filed May 10, 1991 now abandoned.

INTRODUCTION OF THE INVENTION

This invention relates to novel substituted quinazolinone compounds and derivatives thereof which are useful as angiotensin II antagonists in the treatment of elevated blood pressure and congestive heart failure. The substituted quinazolinone compounds of the invention are also useful to reduce elavated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

The compounds of this invention also have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens.* A4, 27-46 (1982); D. H. P. Streeten and G. H. Anderson, Jr. —*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; 291,969; 392,317; 399,731; 403,158; 403,159; 407,342; 411,507; 412,848; and 415,886; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7(1988), *Hypertension*, 13, 489-497 (1989)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted quinazolinone compounds and derivatives thereof which are useful as angiotensin II antagonists, primarily as antihypertensives. The compounds of this invention have the general formula (I):

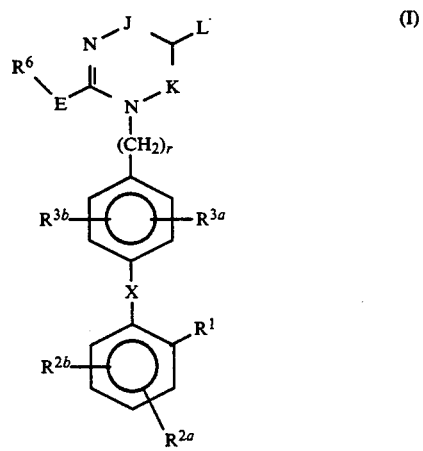

or a pharmaceutically acceptable salt thereof, wherein:
L is connected with J or K to form an aromatic ring as defined below;
J is —C(=M)— or J and L are connected together to form a 6 carbon aromatic ring substituted with $R^{7a}$, $R^{7b}$, $R^{8a}$ and $R^{8b}$, provided that only one of J and K is —C(=M)—;
K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—;
M is O or $NR^{22}$;
$R^1$ is
(a) —$SO_2N(R^{25})$—$OR^{25}$,
(b) —$SO_2NHSO_2R^{23}$,
(c)

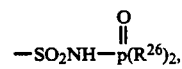

(d)

(e) —SO₂NHCO₂R²³,
(f)
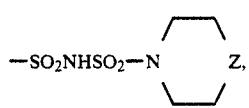
(g) —NHSO₂NHSO₂R²³,
(h)
(i)
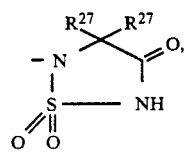
(j)
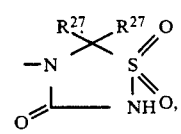
(k)
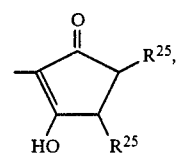
(l)
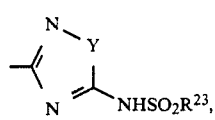
(m)
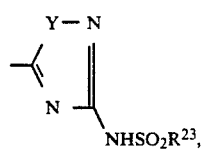
(n)
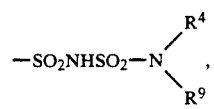
(o)
(p)
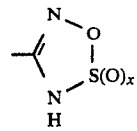
(q)
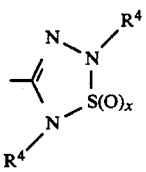
(r)
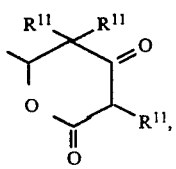
(s)
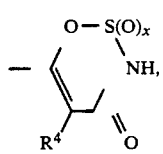
(t)
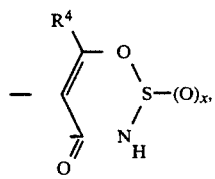
or
(u) —NHSO₂R²³; wherein
Y is O or S; and
Z is O, S(O)$_x$ or NR¹¹;
R$^{2a}$ and R$^{2b}$ are each independently
(a) H,
(b) halogen, (Cl, Br, I, F),
(c) NO₂,
(d) NH₂,
(e) C₁–C₄-alkylamino,
(f) di(C₁–C₄-alkyl)amino,
(g) SO₂NHR⁹,
(h) CF₃,
(i) C₁–C₆-alkyl,
(j) C₁–C₆-alkoxy, (k) ($C_1$-$C_6$-alkoxy)—$CH_2$—,
(l) ($C_1$-$C_6$-alkyl-S)—$CH_2$—,
(m) $C_1$-$C_6$-alkyl—S—,
(n) —$CH_2NR^9R^9$,
(o) $C_2$-$C_6$-alkenyl,
(p) $C_2$-$C_6$-alkynyl;
(q) aryl as defined below,
(r) aryl ($C_1$-$C_4$-alkyl), or
(s) $C_3$-$C_7$-cycloalkyl;

$R^{3a}$ is
(a) H,
(b) halogen (Cl, Br, I, F),
(c) $C_1$-$C_6$-alkyl,
(d) $C_1$-$C_6$-alkoxy, or
(e) $C_1$-$C_6$-alkoxyalkyl;

$R^{3b}$ is
(a) H,
(b) halogen (Cl, Br, I, F),
(c) $NO_2$,
(d) $C_1$-$C_6$-alkyl,
(e) $C_1$-$C_6$-acyloxy, or
(f) $C_3$-$C_7$-cycloalkyl,
(g) $C_1$-$C_6$-alkoxy,
(h) —$NHSO_2R^4$,
(i) hydroxy($C_1$-$C_4$-alkyl),
(j) aryl($C_1$-$C_4$-alkyl),
(k) $C_1$-$C_4$-alkylthio,
(l) $C_1$-$C_4$-alkyl sulfinyl,
(m) $C_1$-$C_4$-alkyl sulfonyl,
(n) $NH_2$,
(o) $C_1$-$C_4$-alkylamino,
(p) di($C_1$-$C_4$-alkyl)amino,
(q) fluoro-$C_1$-$C_4$-alkyl-,
(r) —$SO_2$—$NHR^9$,
(s) aryl as defined below,
(t) furyl,
(u) $CF_3$,
(v) $C_2$-$C_6$-alkenyl, or
(w) $C_2$-$C_6$-alkynyl;

wherein aryl is phenyl or naphthyl optionally substituted with one or two substituents selected from the group consisting of halogen (Cl, Br, I, F), $N(R^4)_2$, $CO_2R^4$, $C_1$-$C_4$-alkyl, $C_1$-$C_4$-alkoxy, $NO_2$, $CF_3$, $C_1$-$C_4$-alkylthio, OH, —$SO_2NR^9R^{10}$, $C_3$-$C_7$-cycloalkyl, $C_3$-$C_{10}$-alkenyl, and —$S(O)_x(C_1$-$C_4$-alkyl);

$R^4$ is H, aryl as defined above, straight chain or branched $C_1$-$C_6$ alkyl optionally substituted with aryl as defined above, or heteroaryl, wherein heteroaryl is an unsubstituted, monosubstituted or disubstituted heteroaromatic 5 or 6 membered ring which can contain one or two heteroatoms selected from the group consisting of N, O, and S, and wherein the substituents are members selected from the group consisting of —OH, —SH, $C_1$-$C_4$-alkyl, $C_1$-$C_4$-alkoxy, —$CF_3$, halogen (Cl, Br, I, F), and $NO_2$;

$R^{4a}$ is aryl as defined above, $C_1$-$C_6$-alkyl, or aryl-$C_1$-$C_6$-alkyl $R^5$ is H,

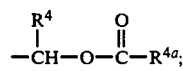

E is a single bond, —$NR^{13}(CH_2)_s$—, —$S(O)_x(CH_2)_s$— where x is 0 to 2 and s is 0 to 5, —CH(OH)—, —O—, or CO—;

$R^6$ is
(a) aryl,
(b) straight chain or branched $C_1$-$C_6$-alkyl, $C_2$-$C_5$-alkenyl or $C_2$-$C_5$-alkynyl each of which can be optionally substituted with a substituent selected from the group consisting of aryl as defined above, $C_3$-$C_7$-cycloalkyl, halogen (Cl, Br, I, F), $CF_3$, $CF_2CF_3$, —$NH_2$, —$NH(C_1$-$C_4$-alkyl), —$OR^4$ —$N(C_1$-$C_4$-alkyl)_2$, —NH—$SO_2R^4$, —$COOR^4$, and —$SO_2NHR^9$; or
(c) heteroaryl as defined hereinabove;
(d) $C_3$-$C_7$-cycloalkyl;
(e) perfluoro-$C_1$-$C_4$-alkyl, or
(f) H;

$R^{7a}$ and $R^{7b}$ are independently
(a) H,
(b) straight chain or branched $C_1$-$C_6$-alkyl, $C_2$-$C_6$-alkenyl or $C_2$-$C_6$-alkynyl,
(c) halogen (Cl, Br, I, F)
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) $C_1$-$C_6$-alkyl optionally substituted with a substituent selected from the group consisting of —OH, -guanidino, $C_1$-$C_4$-alkoxy, —$N(R^4)_2$, $COOR^4$, —$CON(R^4)_2$, —O—$COR^4$, -aryl, -heteroaryl, —$S(O)_x$—$R^{23}$, -tetrazol-5-yl, —$CONHSO_2R^{23}$, —$SO_2NH$-heteroaryl, —$SO_2NHCOR^{23}$, —$PO(OR^4)_2$, —$PO(OR^4)R^9$, —$SO_2NH$-CN, —$NR^{10}COOR^{23}$, morpholino, —N—($C_1$-$C_6$-alkyl)-piperazine, —$COR^4$,

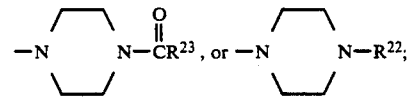

(c) —CO-aryl,
(d) —$C_3$-$C_7$-cycloalkyl,
(e) halogen (Cl, Br, I, F),
(f) —OH,
(g) —$OR^{23}$,
(h) —$C_1$-$C_4$-perfluoroalkyl,
(i) —$S(O)_x$—$R^{23}$,
(j) —$COOR^4$,
(k) —$SO_3H$,
(l) —$NR^4R^{23}$,
(m) —$NR^{24}COR^{23}$,
(n) —$NR^{24}COOR^{23}$,
(o) —$SO_2NR^9R^{10}$,
(p) —$NO_2$,
(q) —$NR^{24}SO_2R^{23}$,
(r) —$NR^{24}CONR^4R^{23}$,
(s)

(t) -aryl or -heteroaryl as defined above,
(u) —$NR^{24}SO_2CF_3$,
(v) —$SO_2NH$-heteroaryl, (w) —$SO_2NHCOR^{23}$,
(x) —$CONHSO_2R^{23}$,
(y) —$PO(OR^4)_2$,
(z) —$PO(OR^4)R^9$,
(aa) —tetrazol-5-yl,
(bb) —CONH(tetrazol-5-yl),
(cc) —$COR^4$,
(dd) —$SO_2NHCN$
(ee)

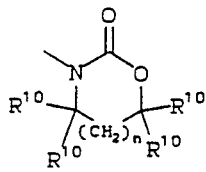

where n=0 or 1,
(ff) —CO-heteroaryl,
(gg) —$NR^{24}SO_2NR^{23}R^9$,
(hh)

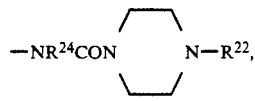

(ii)

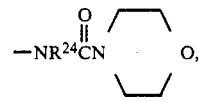

(jj)

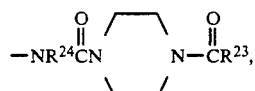

(kk)

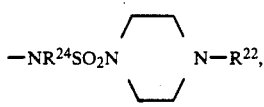

(ll)

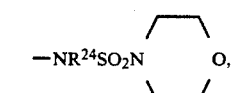

(mm)

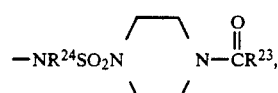

(nn)

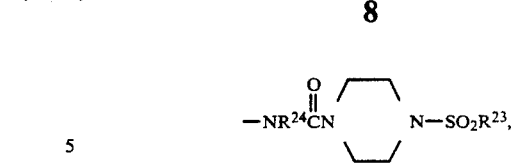

or
(oo)

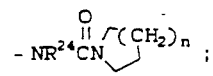

$R^9$ is H, $C_1$-$C_5$-alkyl, aryl or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxy alkyl, or

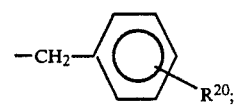

$R^{12}$ is —CN, —$NO_2$, —$CF_3$ or —$CO_2R^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;
$R^{17}$ is —$NR^9R^{10}$, —$OR^{10}$, —$NHCONH_2$, —$NHCSNH_2$,

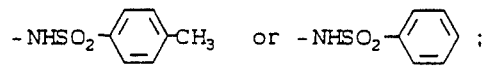

$R^{18}$ and $R^{19}$ are independently $C_1$-$C_4$-alkyl or taken together are —$(CH_2)_q$— where q is 2 or 3;
$R^{20}$ is H, —$NO_2$, —$NH_2$, —OH or —$OCH_3$;
$R^{21}$ is H, aryl, or $C_1$-$C_4$-alkyl optionally substituted with aryl, —$NH_2$, —NH($C_1$-$C_4$-alkyl), —N($C_1$-$C_4$-alkyl)$_2$, —$CO_2R^4$, —OH, —$SO_3H$, or —$SO_2NH_2$;
$R^{22}$ is
  (a) aryl as defined above,
  (b) heteroaryl as defined above, or
  (c) $C_1$-$C_4$-alkyl optionally substituted with a substituent selected from the group consisting of aryl as defined above, heteroaryl as defined above, —OH, —$NH_2$, —NH($C_1$-$C_4$-alkyl), —N($C_1$-$C_4$-alkyl)$_2$, —$CO_2R^4$, halogen (Cl, Br, F, I), and —$CF_3$;
$R^{23}$ is
  (a) aryl as defined above,
  (b) heteroaryl as defined above,
  (c) $C_3$-$C_7$-cycloalkyl,
  (d) $C_1$-$C_6$-alkyl optionally substituted with a substituent selected from the group consisting of aryl as defined above, heteroaryl as defined above, —OH, —SH, $C_1$-$C_4$-alkyl, —O($C_1$-$C_4$-alkyl), $C_3$-$C_7$-cycloalkyl, —S(O)$_x$($C_1$-$C_4$-alkyl), —$CF_3$, halogen (Cl, Br, F, I), —$NO_2$, —$CO_2H$, $CO_2$-$C_1$-$C_4$-alkyl, —$NH_2$, —NH(-

$C_1$-$C_4$-alkyl), —N($C_1$-$C_4$-alkyl)$_2$, —PO$_3$H$_2$, —PO(OH)(O—$C_1$-$C_4$-alkyl), —N($C_1$-$C_4$-alkyl)COR$^{4a}$, —CON($C_1$-$C_4$-alkyl)$_2$, or —PO(OR$^4$)R$^9$, or (e) perfluoro-$C_1$-$C_4$-alkyl, or (f) CH(aryl)$_2$;

$R^{24}$ is (a) $C_1$-$C_6$ alkyl, (b) substituted $C_1$-$C_6$ alkyl in which the substituent is $C_3$-$C_7$ cycloalkyl, $C_1$-$C_4$ alkoxy, hydroxy, di7($C_1$-$C_4$ alkyl)amino, CO$_2$R$^2$, morpholinyl, $C_1$-$C_4$ alkylpiperazinyl, CF$_3$, $C_1$-$C_4$ alkylthio, $C_1$-$C_4$ alkylsulfinyl or $C_1$-$C_4$ alkyl sulfonyl, (c) $C_2$-$C_6$ alkenyl, (d) phenyl $C_1$-$C_6$ alkyl, (e) substituted phenyl $C_1$-$C_6$ alkyl, in which the substituent on the phenyl group is hydroxy, $C_1$-$C_4$ alkoxy, F, Cl, NO$_2$, cyano, CO$_2$R$^2$, di($C_1$-$C_4$ alkyl)amino, CF$_3$, phenyl $C_1$-$C_4$ alkoxy, $C_1$-$C_4$ alkylthio, $C_1$-$C_4$ alkylsulfinyl, or $C_1$-$C_4$ alkylsulfonyl, (f) heteroaryl $C_1$-$C_6$ alkyl, (g) substituted heteroaryl $C_1$-$C_6$ alkyl, in which the substituent on the heteroaryl group is F, Cl, NO$_2$, CO$_2$R$^2$, or di7($C_1$-$C_4$ alkyl)amino, and (h) H;

$R^{25}$ is (a) H, (b) aryl as defined above, or (c) $C_1$-$C_6$-alkyl optionally substituted with aryl, F, Cl, Br, —OH, —NH$_2$, —NH($C_1$-$C_4$-alkyl), —N($C_1$-$C_4$-alkyl)$_2$, or CF$_3$;

$R^{26}$ is (a) aryl as defined above, (b) $C_1$-$C_6$-alkyl optionally substituted with aryl, F, Cl, Br, —OH, —NH$_2$, —NH($C_1$-$C_4$-alkyl), —N($C_1$-$C_4$-alkyl)$_2$, CF$_3$, —COOR$^4$, or CN, (c) —OCH(R$^4$)—O—CO—R$^{4a}$, or (d) —OH or —O—$C_1$-$C_6$-alkyl wherein alkyl is as defined in (b);

$R^{27}$ is (a) H, (b) $C_1$-$C_6$-alkyl optionally substituted with aryl, F, Cl, Br, —OH, —NH$_2$, —NH($C_1$-$C_4$-alkyl), —N($C_1$-$C_4$-alkyl)$_2$, CF$_3$, —COOR$^4$, or CN, or (c) F, Cl, Br;

X is (a) a carbon-carbon single bond, (b) —CO—, (c) —O—, (d) —S—, (e)

(f)

(g)

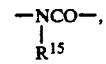

(h) —OCH$_2$—, (i) —CH$_2$O—

(j) —SCH$_2$—, (k) —CH$_2$S—, (l) —NHC(R$^9$)(R$^{10}$), (m) —NR$^9$SO$_2$—, (n) —SO$_2$NR$^9$—, (o) —C(R$^9$)(R$^{10}$)NH—, (p) —CH=CH—, (q) —CF=CF—, (r) —CH=CF—, (s) —CF=CH—, (t) —CH$_2$CH$_2$—, (u) —CF$_2$CF$_2$—, (v)

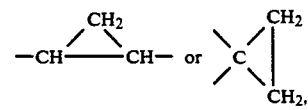

(w)

(x)

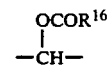

(y)

or (z)

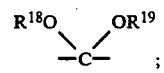

n is 1 to 3;

r is 1 or 2; and x is 0 to 2.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

One embodiment of the compounds of formula (I) are those compounds wherein:

J is —C(O)—;

K and L are connected together to form a 6 carbon aromatic ring substituted with $R^{7a}$, $R^{7b}$, $R^{8a}$ and $R^{8b}$;

$R^1$ is
  (a) —SO$_2$N(R$^{25}$)—OR$^{25}$,
  (b) —SO$_2$NHSO$_2$R$^{23}$,
  (c)

$$-SO_2NH-\overset{\overset{O}{\|}}{P}(R^{26})_2,$$

(d) —SO$_2$NHCO$_2$R$^{23}$,
  (e)

$$-SO_2NHSO_2-N\diagup\diagdown Z,$$

(f) —SO$_2$NHSO$_2$—N(R$^4$)(R$^9$),
  (g) —NHSO$_2$NHSO$_2$R$^{23}$,
  (h)

$$-NHSO_2NH\overset{\overset{O}{\|}}{P}(R^{26})_2;$$

(i)

$$\begin{array}{c}R^{27}\phantom{xx}R^{27}\\-N\phantom{xxx}\diagdown\phantom{x}\diagup\phantom{x}O\\\phantom{xx}|\phantom{xxxxx}\|\\\phantom{xxx}S\phantom{xx}---NH\\\phantom{xx}\diagup\phantom{x}\diagdown\\\phantom{xx}O\phantom{xxx}O\end{array}$$

(j)

$$\begin{array}{c}Y-N\\\diagdown\\\phantom{x}N\\\phantom{xxxx}NHSO_2R^{23},\end{array}$$

(k)

$$\begin{array}{c}N\diagdown\\\phantom{xx}\diagdown O\\\phantom{xxxx}|\\\phantom{xx}N\phantom{xx}S(O)_x,\\\phantom{x}|\\\phantom{x}H\end{array}$$

(l)

$$\begin{array}{c}\phantom{xx}\diagdown N\diagdown\phantom{xx}R^4\\\phantom{xxxxxxxxx}N\\-N\phantom{xxx}\diagup\\\phantom{xxx}\diagdown\phantom{x}S(O)_x,\\\phantom{xxx}R^4\end{array}$$

(m)

$$\begin{array}{c}\phantom{xx}O\phantom{xx}O\\\phantom{xx}\|\phantom{xx}\|\\-N-C-COH,\\\phantom{x}|\\\phantom{x}R^4\end{array}$$

or
  (n) —NHSO$_2$R$^{23}$;

X is a single bond;

$R^{2a}$ is H;

$R^{2b}$ is H, F, Cl, CF$_3$, C$_1$-C$_6$-alkyl, C$_2$-C$_4$-alkenyl, or C$_2$-C$_4$-alkynyl;

$R^{3a}$ is H;

$R^{3b}$ is H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;

E is a single bond, —O— or —S—;

$R^6$ is
  (a) C$_1$-C$_5$ alkyl optionally substituted with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F,
  (b) C$_2$-C$_5$-alkenyl or C$_2$-C$_5$-alkynyl, or,
  (c) C$_3$-C$_5$-cycloalkyl;

$R^{7a}$ and $R^{7b}$ are each H;

$R^{8a}$ and $R^{8b}$ are independently
  (a) H,
  (b) C$_1$-C$_4$-alkyl optionally substituted with COOR$^4$, OCOR$^{4a}$, OH, aryl, heteroaryl, morpholinyl, $$-N\diagup\diagdown N-\overset{\overset{O}{\|}}{C}R^{23},\text{ or }-N\diagup\diagdown N-R^{22},$$

(c) C$_2$-C$_4$-alkenyl,
  (d) —OH,
  (e) —NO$_2$,
  (f) —NR$^{24}$COR$^{23}$,
  (g) —C$_1$-C$_4$-alkoxy,
  (h) —NR$^{24}$CO$_2$R$^{23}$,
  (i) —NR$^4$R$^{23}$,
  (j) halogen (Cl, F, Br),
  (k) —CF$_3$,
  (l) —CO$_2$R$^4$,
  (m) —CO-aryl as defined above,
  (n) heteroaryl,
  (o) —S(O)$_x$—C$_1$-C$_4$-alkyl,
  (p) —SO$_2$—NH—C$_1$-C$_4$-alkyl,
  (q) —SO$_2$—NH-aryl as defined above,
  (r) —NR$^{24}$SO$_2$CH$_3$,
  (s) aryl as defined above,
  (t) —NR$^{24}$CONR$^4$R$^{23}$,
  (u)

(v) 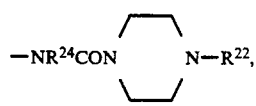

(w) 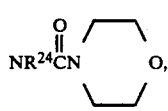

or
(x) 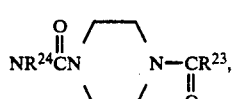

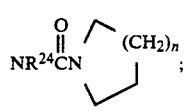

X is a single bond;
r is one; and
x is 0 to 2.

In a class of this embodiment are those compounds of Formula (I) wherein:

$R^1$ is:
(a) $-SO_2N(R^{25})-OR^{25}$,
(b) $-SO_2NHSO_2R^{23}$,
(c)

(d) $-SO_2NHCO_2R^{23}$,
(e)

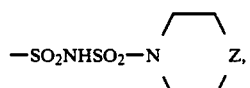

(f) $-SO_2NHSO_2-N(R^4)(R^9)$,
(g) $-NHSO_2NHSO_2R^{23}$, or
(h)

(i)

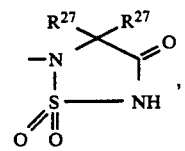

(j)

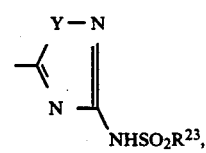

(k)

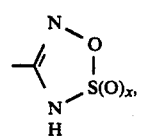

(l)

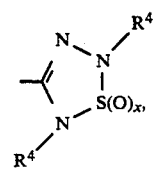

(m)

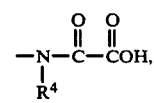

or
(n) $-NHSO_2R^{23}$;

X is a single bond;
E is a single bond;
r is one;
x is 0 to 2;
$R^{2a}$, $R^{2b}$, $R^{3a}$ and $R^{3b}$ are each H, $-C_1-C_6$-alkyl, $-C_2-C_4$-alkynyl, $-Cl$, $-F$, $-NO_2$, or $-CF_3$;
$R^6$ is methyl, ethyl, -n-propyl, isopropyl, -n-butyl, -trans-2-butenyl, $CH_2CH_2CF_3$, $-CH_2CH_2CH_2CF_3$, -cyclopropyl, or -cyclopropylmethyl;
$R^{8a}$ and $R^{8b}$ are each independently H, $-NO_2$, $-C_1-C_4$-alkyl, $-NHR^4$, $-NR^{24}CO-R^{23}$, $-S(O)_x-(C_1-C_4$-alkyl), $-N(CH_3)_2$, $-OCH_3$, $-NR^{24}COCH_2NH_2$, $-NR^{24}CO$-furoyl, $-NR^{24}COCH_2N(CH_3)_2$, $-COOH$, $-COOCH_3$, $-CH_2OCOCH_3$, $Cl$, $-CH_2COOCH_3$, $-NR^{24}CON(R^4)_2$, $-NR^{24}CO_2R^4$, $-CH_2COOH$, $CH_2OH$, aryl, heteroaryl, $-CH_2$-heteroaryl,

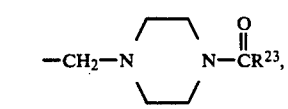

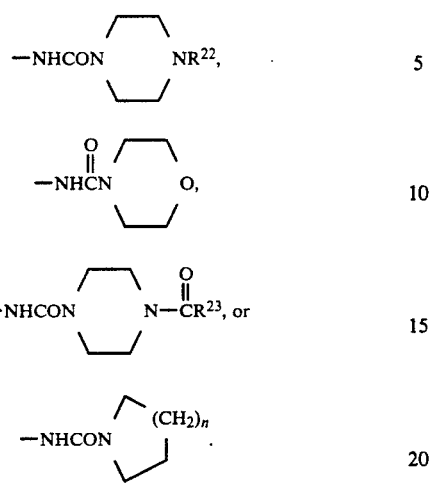

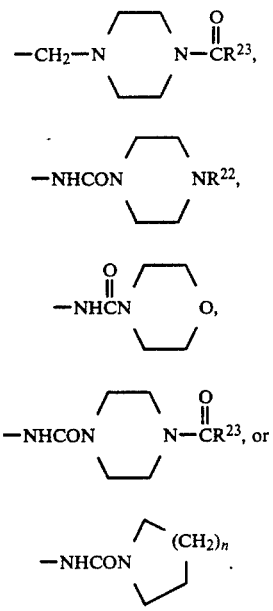

In a subclass of this class are those compounds of Formula (I) wherein:

$R^1$ is: $-SO_2NHCO_2R^{23}$;

X is a single bond;

$R^{2a}$, $R^{2b}$, $R^{3a}$ and $R^{3b}$ are each H, $-C_1-C_4$-alkyl, $-Cl$ or F;

$R^6$ is methyl, ethyl, -n-propyl, isopropyl, -n-butyl, -trans-2-butenyl, $CH_2CH_2CF_3$, $-CH_2CH_2CH_2CF_3$, -cyclopropyl, or -cyclopropylmethyl;

$R^{8a}$ and $R^{8b}$ are each independently H, $-NO_2$, $-C_1-C_4$-alkyl, $-NHR^4$, $-NR^{24}CO-R^{23}$, $-S(O)_x-(C_1-C_4$-alkyl$)$, $-N(CH_3)_2$, $-OCH_3$, $-NR^{24}COCH_2NH_2$, $-NR^{24}CO$-furoyl, $-NR^{24}COCH_2N(CH_3)_2$, $-COOH$, $-COOCH_3$, $-CH_2OCOCH_3$, Cl, $-CH_2COOCH_3$, $-NR^{24}CON(R^4)_2$, $-NR^{24}CO_2R^4$, $-CH_2COOH$, $CH_2OH$, aryl, heteroaryl, $-CH_2$-heteroaryl, Exemplifying this embodiment are the compounds of the Formula II shown in Table A:

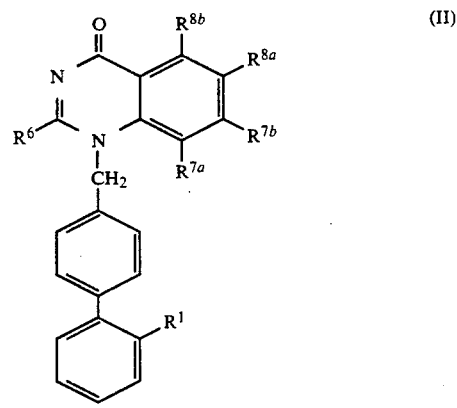

(II)

TABLE A

| Compound No. | $R^1$ | $R^6$ | $R^{7a}$ | $R^{7b}$ | $R^{8a}$ | $R^{8b}$ |
|---|---|---|---|---|---|---|
| A1 | $-SO_2NHOH$ | Pr | H | Me | Me | H |
| A2 | $-SO_2NHSO_2Ph$ | Pr | H | Me | Me | H |
| A3 | $-SO_2NHSO_2Me$ | Pr | H | H | Me | H |
| A4 | $-SO_2NHSO_2-\prec$ | Bu | H | Me | $CO_2H$ | H |
| A5 | (structure with N, O, S(O)_2) | Pr | Me | Me | H | H |
| A6 | (structure with N, N—Ph, S=O) | Pr | H | Me | Me | H |
| A7 | $-NH-C(=O)-CO_2H$ | Pr | H | H | Me | H |

TABLE A-continued

| Compound No. | R¹ | R⁶ | R⁷ᵃ | R⁷ᵇ | R⁸ᵃ | R⁸ᵇ |
|---|---|---|---|---|---|---|
| A8 | —SO₂NHSO₂—⟨(i-Pr) | Pr | H | Me | Et | H |
| A9 | —SO₂NHP(O)(O—CH₂Ph)₂ | Pr | Me | Me | H | H |
| A10 | (N-sulfonyl glycinimide ring) | Pr | H | Me | Me | H |
| A11 | (isoxazole)—NHSO₂Ph | Bu | H | Me | i-Pr | H |
| A12 | (oxathiazole ring) | Bu | H | H | Me | Me |
| A13 | —NHSO₂—(2-thienyl) | Pr | H | H | i-Pr | Me |
| A14 | —NHSO₂—(2,4-difluorophenyl) | Pr | H | H | i-Pr | Me |
| A15 | —NHSO₂—(3-pyridyl) | Pr | H | H | i-Pr | Me |
| A16 | —SO₂NHCO₂Et | Pr | H | H | i-Pr | H |

In a second embodiment are those compounds of formula (I) wherein:

K is —C(O)—;

J and L are connected together to form a 6 carbon aromatic ring substituted with $R^{7a}$, $R^{7b}$, $R^{8a}$ and $R^{8b}$; and, the class and sub-class of this embodiment are as defined above.

Exemplifying this embodiment are the compounds of the Formula III shown in Table B:

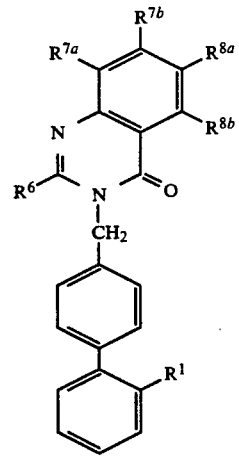

(III)

TABLE B

| Compound No. | R¹ | R⁶ | R⁷ᵃ | R⁷ᵇ | R⁸ᵃ | R⁸ᵇ |
|---|---|---|---|---|---|---|
| B1 | —SO₂NHOH | Pr | Me | Me | Me | H |
| B2 | —SO₂NHSO₂Ph | Bu | H | H | i-Pr | H |
| B3 | —SO₂NHSO₂Me | Pr | H | H | Me | H |

TABLE B-continued

| Compound No. | R$^1$ | R$^6$ | R$^{7a}$ | R$^{7b}$ | R$^{8a}$ | R$^{8b}$ |
|---|---|---|---|---|---|---|
| B4 | —SO$_2$NHSO$_2$—CH(CH$_3$)$_2$ | Pr | H | H | i-Pr | H |
| B5 | (1,2,4-oxathiazoline, N—S(O)$_2$, NH) | Pr | H | Me | Me | H |
| B6 | (N-Ph substituted 1,2,4-thiadiazoline S=O, NH) | Pr | Me | H | i-Pr | H |
| B7 | —NH—C(=O)—CO$_2$H | Bu | H | H | Me | Me |
| B8 | —SO$_2$NHSO$_2$—CH(CH$_3$)$_2$ | Pr | H | H | i-Pr | H |
| B9 | —SO$_2$NHP(=O)(O—CH$_2$Ph)$_2$ | Pr | H | H | i-Pr | H |
| B10 | (cyclic sulfamide with C=O, N—H) | Bu | H | Me | H | Me |
| B11 | (1,2,4-oxadiazole —NHSO$_2$Ph) | Pr | H | H | —N(Me)CO$_2$i-Bu | H |
| B12 | (1,2,4-oxathiadiazoline, NH, S(=O)$_2$) | Pr | H | Me | —N(Me)CO$_2$i-Bu | H |
| B13 | —NHSO$_2$-(2-thienyl) | Pr | H | H | —N(Me)CO$_2$i-Bu | H |
| B14 | —NHSO$_2$-(2,4-difluorophenyl) | Pr | H | H | —N(Bzl)CO$_2$i-Bu | Me |
| B15 | —NHSO$_2$-(3-pyridyl) | Pr | H | H | —N(Bu)COPh | H |
| B16 | —SO$_2$NHCO$_2$Et | Pr | H | H | iPr | H |
| B17 | —SO$_2$NHCO$_2$i-Pr | Pr | H | H | iPr | H |
| B18 | —SO$_2$NHPO(OEt)$_2$ | Pr | H | H | iPr | H |

TABLE C

Further exemplifications of this embodiment include:

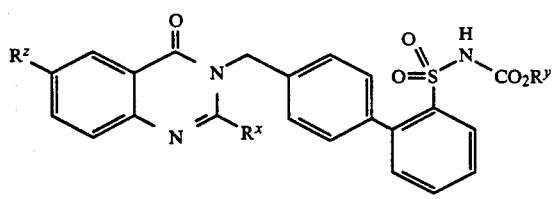

| $R^x$ | $R^y$ | $R^z$ |
|---|---|---|
| Pr | butyl | NO2— |
| Pr | butyl | NH2— |
| Pr | butyl | BuNHCONH— |
| Pr | butyl | EtNHCONH— |
| Pr | 2-dimethylaminoethyl | EtNHCONH— |
| Bu | butyl | iPrN(Me)CONH— |
| Pr | butyl | iPrNHCONH— |
| Pr | propyl | iPrNHCONH— |
| Pr | pentyl | iPrNHCONH— |
| Pr | butyl | MeNHCONH— |
| Pr | 3-methylbutyl | EtNHCONH— |
| Pr | 3-methylbutyl | MeNHCONH— |
| Pr | butyl | PrNHCONH— |
| Pr | 2-cyclopropylethyl | EtNHCONH— |
| Pr | 3,3-dimethylbutyl | EtNHCONH— |
| Bu | pentyl | iPrNHCONH— |
| Bu | butyl | iPrNHCONH— |
| Bu | 2-methoxyethyl | iPrNHCONH— |
| Pr | 3-methylbutyl | PhCO— |
| Pr | 3-methylbutyl | Me2NCONH— |
| Pr | 3-methylbutyl | 4-HO—PhCONH— |
| Pr | 3-methylbutyl | 4-MeO—PhCONH— |
| Pr | 3-methylbutyl | 4-Me2N—PhCONH— |
| Bu | 3,3-dimethylbutyl | PhCONH— |
| Pr | 2-cyclopropylethyl | 2-FurylCONH— |
| Bu | butyl | HOCH2CH2CONH— |
| Pr | 3,3-dimethylbutyl | —NHCOCH2CH2COOH |
| Bu | butyl | —NHCOCH2COOH |
| Pr | 3-methylbutyl | Me2NCH2CH2CONH— |
| Bu | butyl | Me2NC(N)NH— |
| Pr | 3,3-dimethylbutyl | (4-cPrCO-piperazinyl)-CONH |
| Pr | 3,3-dimethylbutyl | (4-Me-piperazinyl)-CO—NH |
| Bu | 2-cyclopropylethyl | morpholinylCONH— |
| Pr | butyl | PrOCONH— |
| Pr | 3,3-dimethylbutyl | H2NCONH— |
| Bu | 2-cyclopropylethyl | HOCH2CONH— |
| Bu | 3,3-dimethylbutyl | 4-pyridylCONH— |
| Et | 2-cyclopentylethyl | EtNHCONH— |
| Pr | 3-methylbutyl | MeNHCONH— |
| Pr | 3-methylbuten-2-yl | EtNHCONH— |
| Bu | 2-cyclopropylethyl | EtNHCONH— |
| Bu | 3-methylbutyl | EtNHCONH— |
| i-Bu | 3-methylbutyl | EtNHCONH— |
| c-PrCH2 | 3-methylbutyl | EtNHCONH— |
| n-Pn | 3-methylbutyl | EtNHCONH— |
| Bu | 2-cyclopropylethyl | MeNHCONH— |
| Bu | 3-methylbutyl | MeNHCONH— |
| Bu | 3-methylbutyl | Et2NCONH— |
| Bu | 3-methylbutyl | i-PrNHCONH— |
| Bu | 3-methylbutyl | EtNMeCONH— |
| Bu | 3,3-dimethylbutyl | MeNHCONH— |
| Bu | 2-methoxyethyl | EtNHCONH— |
| Bu | 2-ethoxyethyl | EtNHCONH— |
| Bu | 2-isopropoxyethyl | EtNHCONH— |
| Bu | 2-isopropoxyethyl | MeNHCONH— |
| Pr | 2-cyclopropylpropyl | EtNHCONH— |
| Pr | Butyl | 2-pyridyl- |
| Pr | Butyl | 3-pyridyl- |
| Pr | Butyl | 4-Me—Ph— |
| Pr | Butyl | methyl(piperazinyl-N-acetyl) |
| Pr | Butyl | methyl(piperazinyl-N-cyclopropylcarbonyl) |
| Pr | Butyl | methyl(N1-imidazolyl) |
| Pr | i-pentyl | 2-pyridyl- |
| Pr | i-pentyl | 3-pyridyl- |
| Pr | butyl | —NH(pentyl) |
| Pr | benzyl | EtNHCONH— |
| Pr | benzyl | MeNHCONH— |

TABLE C-continued

Further exemplifications of this embodiment include:

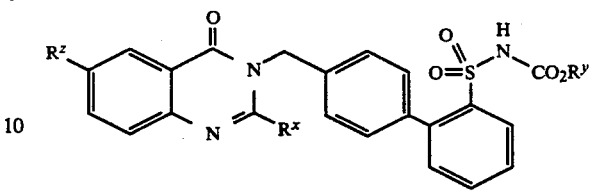

| $R^x$ | $R^y$ | $R^z$ |
|---|---|---|
| Pr | 2-methoxybenzyl | EtNHCONH— |
| Pr | 2-chlorobenzyl | EtNHCONH— |
| Pr | 2-ethylbenzyl | MeNHCONH— |
| Pr | 1,1-dimethylbutyl | EtNHCONH— |
| Bu | 1,1,3-trimethylbutyl | EtNHCONH— |
| Pr | butyl | N-pyrrolidineCONH |
| Pr | 3-methylbutyl | N-(N'-cyclopropyl-carbonylpiperazinyl)-CONH— |
| Pr | butyl | N-(N'-methyl-piperazinyl)-CONH— |
| Pr | cyclopropylmethyl | EtNHCONH— |
| Pr | butyl | i-PrNHCONH— |

TABLE D

Still further exemplifications of this embodiment include:

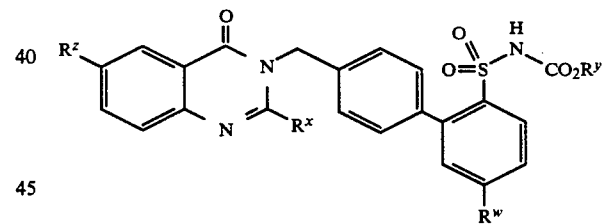

| $R^w$ | $R^x$ | $R^y$ | $R^z$ |
|---|---|---|---|
| Pr | Pr | butyl | EtNHCONH— |
| Et | Bu | ethyl | EtNHCONH— |
| EtO | Pr | butyl | iPrN(Me)CONH— |
| i-Pr | Pr | 3-methylbutyl | EtNHCONH— |

In a third embodiment are those compounds of formula (I) wherein:

K is —C(=NR$^{22}$)—;

J and L are connected together to form a 6 carbon aromatic ring substituted with $R^{7a}$, $R^{7b}$, $R^{8a}$ and $R^{8b}$; and, the class and sub-class of this embodiment are as defined above.

Exemplifying this embodiment are the compounds of the Formula IV shown in Table E:

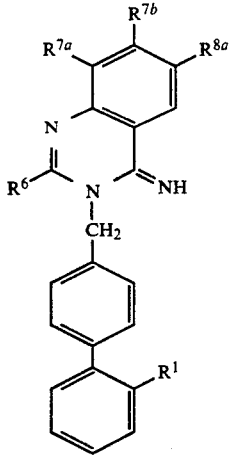
(IV)

TABLE E

| Compound No. | R¹ | R⁶ | R⁷ᵃ | R⁷ᵇ | R⁸ᵃ |
|---|---|---|---|---|---|
| C1 | —SO₂NHOH | Pr | Me | H | i-Pr |
| C2 | —SO₂NHSO₂Ph | Bu | Me | Me | H |
| C3 | —SO₂NHSO₂Me | Pr | H | H | i-Pr |
| C4 | —SO₂NHSO₂—⟨ | Pr | H | Me | Me |
| C5 | (N–O / N–SO cyclic with H) | Pr | H | H | i-Pr |
| C6 | (N–N-Ph / N–S=O cyclic with H) | Pr | H | H | Me |
| C7 | —NH—C(=O)—CO₂H | Bu | H | H | Me |
| C8 | —SO₂NHSO₂—⟨ | Pr | H | H | i-Pr |
| C9 | —SO₂NHP(=O)(O—CH₂Ph)₂ | Pr | H | H | i-Pr |
| C10 | (—N / S(O₂)—N–H cyclic with =O) | Bu | H | H | Me |
| C11 | (N—O / N cyclic)—NHSO₂Ph | Pr | H | H | Me |
| C12 | (N–O / N–S(=O)₂ cyclic with H) | Pr | H | H | i-Pr |

TABLE E-continued

| Compound No. | R¹ | R⁶ | R⁷ᵃ | R⁷ᵇ | R⁸ᵃ |
|---|---|---|---|---|---|
| C13 | —NHSO₂-(2-thienyl) | Pr | H | H | i-Pr |

| ABBREVIATIONS USED IN SCHEMES | |
|---|---|
| DMAP | Dimethylaminopyridine |
| -OTs | p-toluenesulphonate |
| -OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

Scheme 1 illustrates the preparation of 1,2-disubstituted quinazolin-4-(1H)-ones of Formula 1 wherein J=—C(O)— and E is a single bond. An appropriately substituted anthranilonitrile is acylated using the requisite acyl chloride. The resulting amide is alkylated with sodium hydride and the appropriate alkyl halide (or pseudohalide). The resulting tertiary amide is then rearranged/cyclized with basic hydrogen peroxide[1]. 2-Substituted quinazolin-4-(1H)-ones 6 wherein E is a single bond and K is —C(O)— may be prepared from substituted anthranilonitriles as described in Scheme 1. The appropriately substituted anthranilonitrile is acylated using the requisite acyl chloride to give 2 then cyclized with basic hydrogen peroxide to give 6.

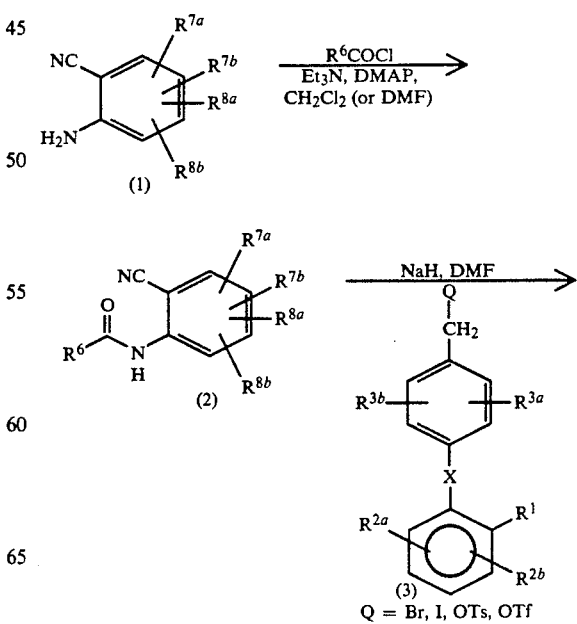

SCHEME 1

Q = Br, I, OTs, OTf

-continued
SCHEME 1

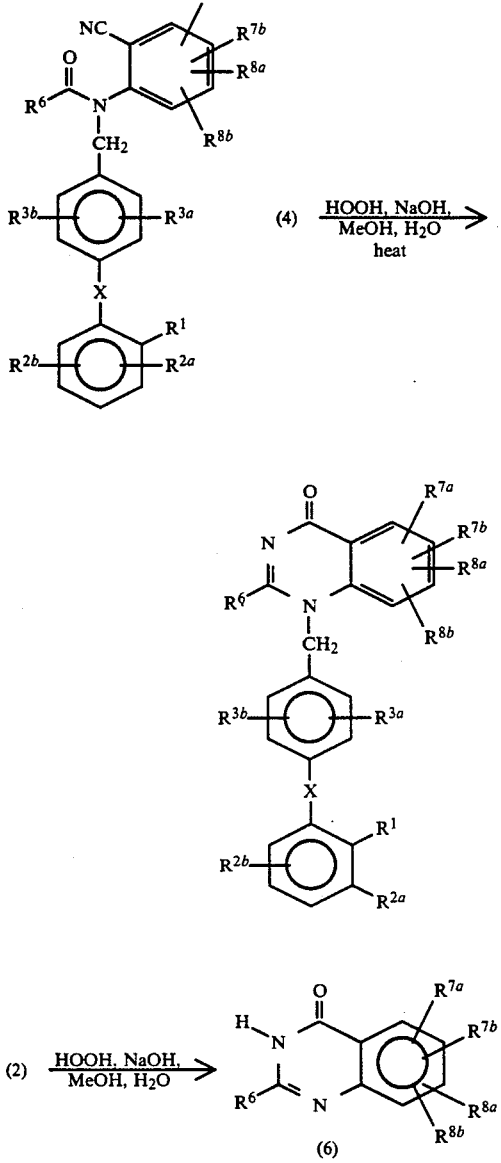

SCHEME 2

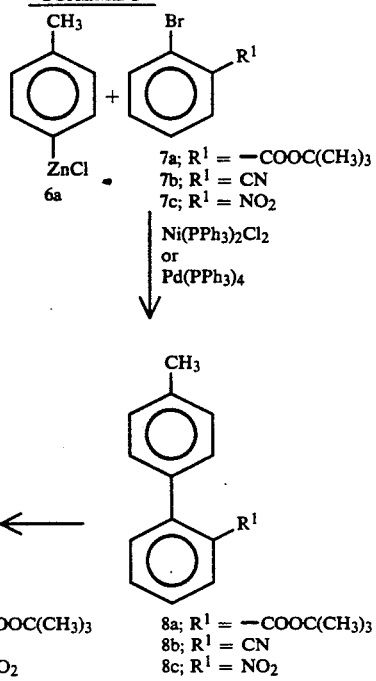

The benzyl halides (3) including alkylating agents 9a and 9b (Reaction Scheme 2) can be prepared as described in European Patent Applications 253,310 and 291,969 and the references cited therein. However, a preferred method to prepare the biphenyl precursors 8a, 8b and 8c using Ni(O) or Pd(O) catalyzed cross-coupling reaction [E. Negishi, T. Takahashi, and A. O. King, *Org. Synthesis*, 66, 67 (1987)] is outlined in Reaction Scheme 2 (for other alkylating agents, see Schemes 16 and 17). As shown in Reaction Scheme 2, treatment of 4-bromotoluene (4a) with t-BuLi, followed by the addition of a solution of $ZnCl_2$, produces the organozinc compound (6a). Compound (6a) is then coupled with 7a or 7b in the presence of $Ni(PPh_3)_2Cl_2$ catalyst to produce the desired biphenyl compound 8a or 8b ($PPh_3$=triphenylphosphine). Similarly, 1-iodo-2-nitrobenzene (7c) is coupled with organo-zinc compound 6a in the presence of $Pd(PPh_3)_4$ catalyst [prepared by treating $Cl_2Pd(PPh_3)_2$ with $(i-Bu)_2AlH$ (2 equiv.)] to give the biphenyl compound 8c. These precursors, 8a, 8b and 8c, are then transformed into halomethylbiphenyl derivatives 9a, 9b and 9c, respectively, according to procedures described in European Patent Applications 253,310 and 291,969.

When there is additional substitution on the second phenyl ring ($R^{2a}$, $R^{2b}$=hydrogen) the preferred method to prepare the biphenyl precursors 8d and 8e, using the Pd(O) catalyzed cross-coupling reaction [J. K. Stille, *Angew. Chem. Int. Ed. Engl.*, 25, 508 (1986)], is outlined in reaction Scheme 2a. (Similar chemistry may be applied to the alkylating agents of the type outlined in Schemes 16 and 17). As shown in reaction Scheme 2a, p-tolyltrimethyltin (6a) is coupled with 7d or 7e in refluxing toluene in the presence of 5 mole % of $Pd(PPh_3)_4$ to produce the desired biphenyl compounds 8d and 8e. Table I illustrates the synthetic utility of this protocol. Compounds 8d ($R^2=NO_2$) and 8e ($R^2=NO_2$) could be converted to their respective chlorides by catalytic hydrogenation, diazotization and treatment with copper (I) chloride. The biphenyl fluorides which could not be obtained by direct coupling to a fluoro arylbromide were prepared from 8d ($R^2=NO_2$) and 8e ($R^2=NO_2$) via reduction, formation of the diazonium tetrafluoroborate salt and thermal decomposition. These precursors 8d ($R^2=NO_2$ or F or Cl) and 8e ($R^2=NO_2$ or F or Cl) are then transformed into the halomethyl biphenyl derivatives 9d and 9e respectively according to the procedures described in European Patent Applications 253,310 and 292,969.

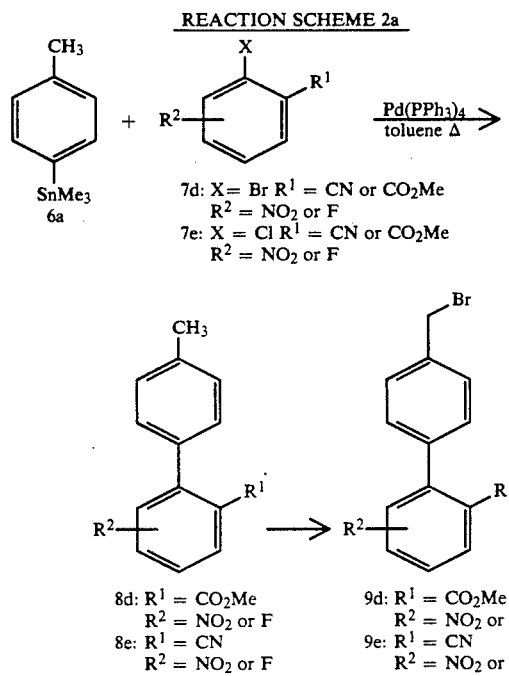

SCHEME 3

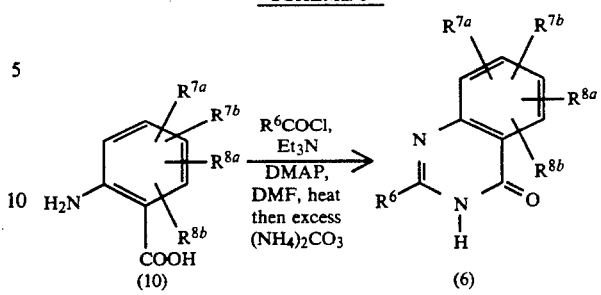

Scheme 4 illustrates the general preparation of 2,3-disubstituted quinazolin-4(3H)-ones (11a) of formula (I) wherein E is a single bond and K is —C(O)—. An appropriately substituted 2-substituted quinazolin-4(1H)-one (6) (see Scheme 1 or Scheme 3) is alkylated using sodium hydride and the appropriate alkyl halide (or pseudohalide). This reaction sometimes gives some O-alkylated product, generally less than 20% of the isolated reaction products.

SCHEME 4

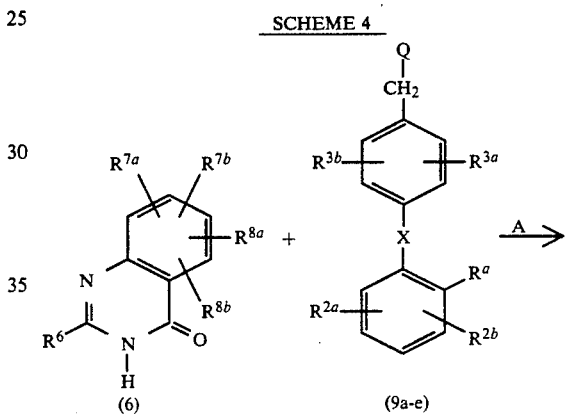

TABLE I
Biphenyl Synthesis

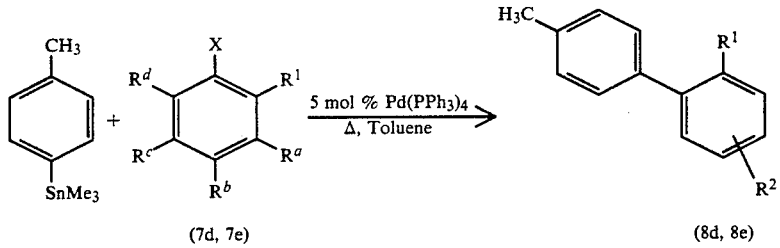

| X | $R^1$ | $R^a$ | $R^b$ | $R^c$ | $R^d$ | Product ($R^2$) | Rf (solvent) | Yield |
|---|---|---|---|---|---|---|---|---|
| Br | CO$_2$Me | NO$_2$ | H | H | H | 8d (3'-nitro) | 0.35 (15:1 Hex/EtOAc) | 71% |
| Br | CN | H | NO$_2$ | H | H | 8e (4'-nitro) | 0.62 (2 × 6:1 Hex/EtOAc) | 74% |
| Br | CO$_2$Me | H | F | H | H | 8d (4'-fluoro) | 0.43 (15:1 Hex/EtOAc) | 83% |
| Cl | CO$_2$Me | H | H | NO$_2$ | H | 8d (5'-nitro) | 0.22 (15:1 Hex/EtOAc) | 70% |
| Br | CO$_2$Me | H | H | H | NO$_2$ | 8d (6'-nitro) | 0.24 (15:1 Hex/EtOAc) | 79% |
| Br | CN | H | F | H | H | 8e (4'-fluoro) | 0.44 (15:1 Hex/EtOAc) | 64% |
| Cl | CN | H | H | F | H | 8e (5'-fluoro) | 0.40 (15:1 Hex/EtOAc) | 62% |

Scheme 3 shows an alternate preparation of 2-substituted quinazolin-4(3H)-ones (6) starting with the corresponding anthranilic acid. The appropriately substituted anthranilic acid (10) is treated with two equivalents of the requisite acyl chloride in DMF with triethylamine and DMAP at 0° C. This is then heated to 110° C. for two hours after which time excess ammonium carbonate is added.[2]

-continued
SCHEME 4

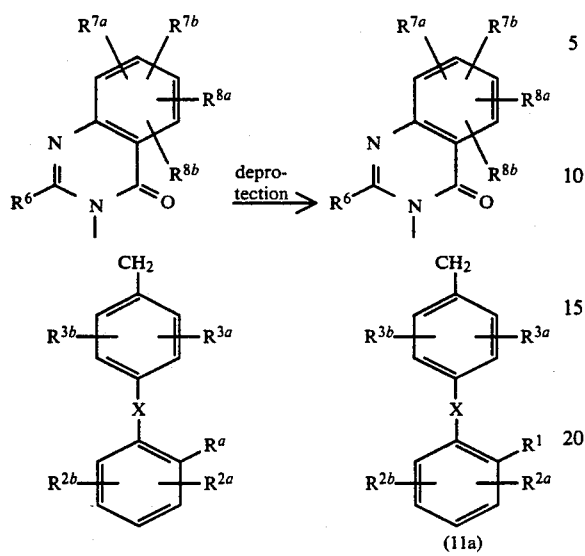

$R^1$ = fully protected precursor of $R^1$
A = (1) NaH, DMF or
(2) NaOH, PhCH$_2$N$^+$Me$_3$$^-$OH, toluene.

Schemes 5, 6, and 7 provide an alternate route to compounds of Formula (1) (11b) wherein E is a single bond, K is —C(O)—, and r is 1 or 2.

Two methods for preparing 3,1,4-benzoxazones (10) are illustrated in Scheme 5. Substituted anthranilic acids (10) may be acylated and cyclized by heating them in DMF with an acyl chloride, triethylamine and DMAP.[3] Alternatively, they may also be prepared by heating an appropriately substituted anthranil (13) with an acyl chloride in pyridine.[4]

The necessary alkyl amine may then be prepared from the alkyl halide (or pseudohalide) using the standard literature procedures (Scheme 6)[5]. The amine where r=2 may be prepared from (9a-e) using procedures known to those skilled in the art where appropriate protecting groups are used for $R^1$, $R^{2a}$, $R^{2b}$, $R^{3a}$ and $R^{3b}$. Then, the amine and the 3,1,4-benzoxazone are heated together to give the desired 2,3-disubstituted quinazolinone (11b) (Scheme 7). Removal of the protecting group and/or further elaboration of $R^a$ provides the desired analogs bearing $R^1$.

SCHEME 5

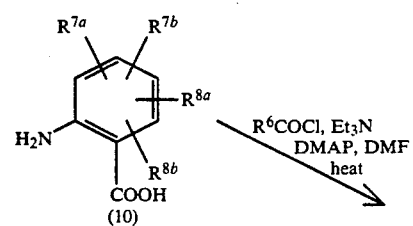

-continued
SCHEME 5

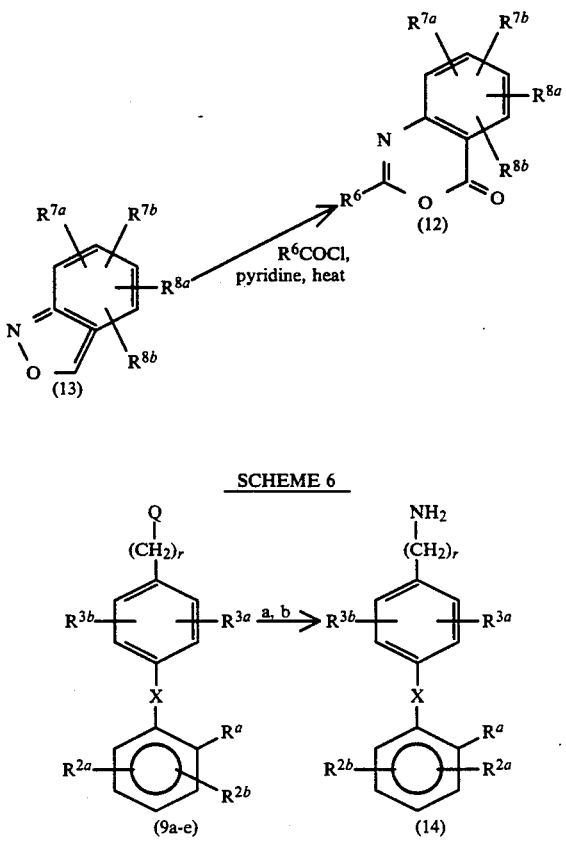

SCHEME 6 for r = 1:
a) LiN$_3$/DMSO
b) P(Ph)$_3$, H$_2$O
for r = 2:
a) Na$^+$ $^-$CH$_2$NO$_2$, DMF
b) H$_2$, 10% Pd/C

SCHEME 7

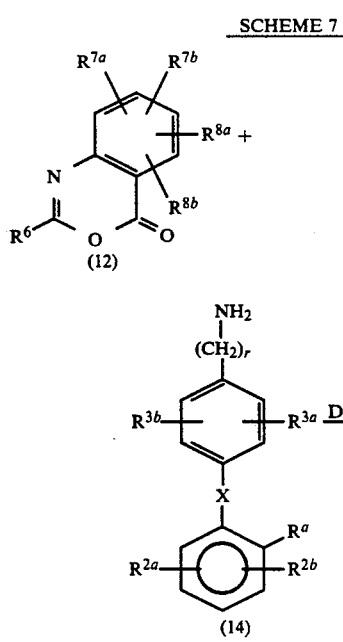

-continued
SCHEME 7

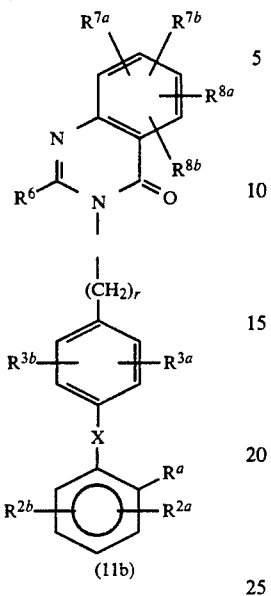

(11b)

Substituted 2-alkylthioquinazolin-4(3H)-ones wherein K is —C(O)— and E is —S— (15) may be prepared from their corresponding substituted anthranilic acids as shown in Scheme 8. The amine (14) from Scheme 6 can be converted to its isothiocyanate (16) upon treatment with thiophosgene. This may then be reacted with an appropriately substituted anthranilic acid to give the desired 3-alkyl-2-mercaptoquinazolin-4(3H)-one.(17)[6] A second alkylation of the mercapto group then gives the desired 2-alkylthio-3-alkylquinazolin-4(3H)-one. (15)[7]

SCHEME 8

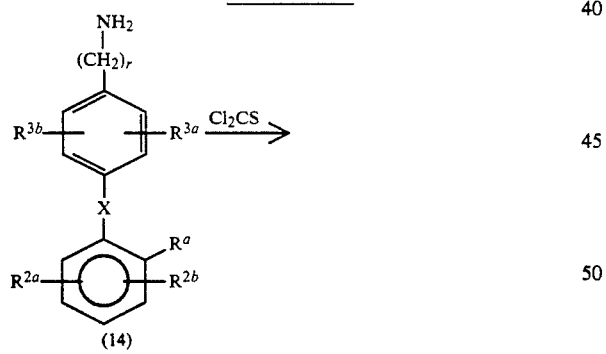

-continued
SCHEME 8

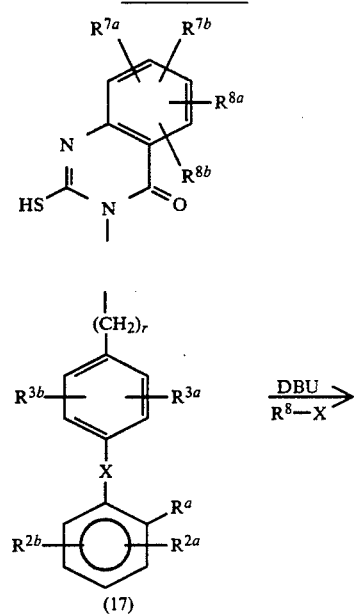

(17)

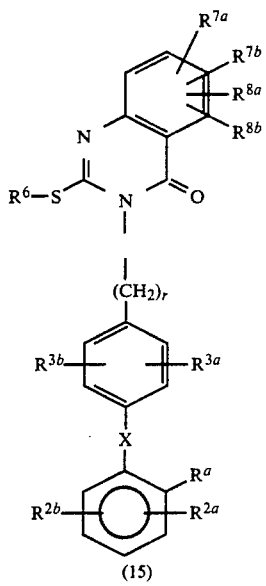

(15)

Similarly, 2-alkoxyquinazolin-4(3H)-ones wherein K is —C(O)— and E is —O— may be prepared from their corresponding substituted anthranilic acids as shown in Scheme 9.[8] Alkylation with the appropriate alkyl halide 9a–e according to the methods developed by Lange and Sheibley [9] then gives the final product 19.

SCHEME 9

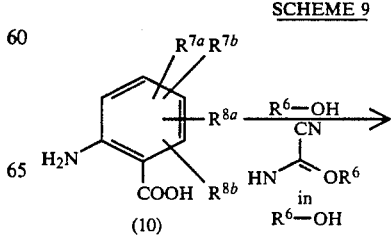

(10)

-continued
SCHEME 9

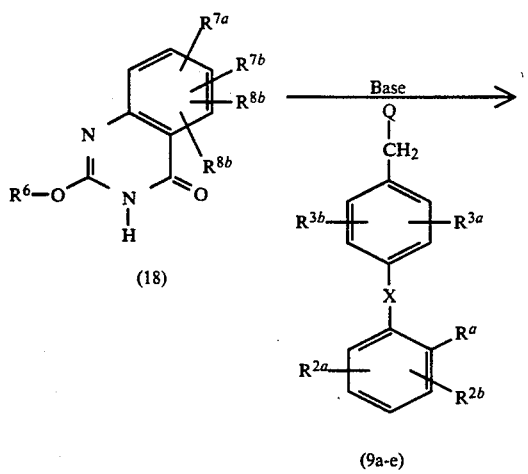

(18)

(9a-e)

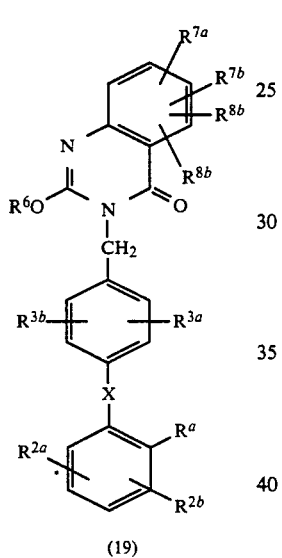

(19)

Scheme 10 illustrates a route to the isomeric 1,2-disubstituted quinazolin-4(1H)-ones (20) wherein J is —C(O)— and where E is S or O. An anthranilonitrile 1 is acylated with an alkyl haloformate or an alkylthiol haloformate to give 21.[10] This may then be deprotonated and alkylated with the appropriate alkyl halide to give the intermediate carbamate nitrile 22.[11] Conversion of the intermediate then occurs when the material is treated with basic hydrogen peroxide to yield the desired product 20.

SCHEME 10

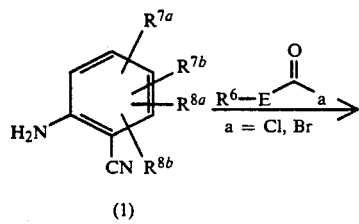

(1)

-continued
SCHEME 10

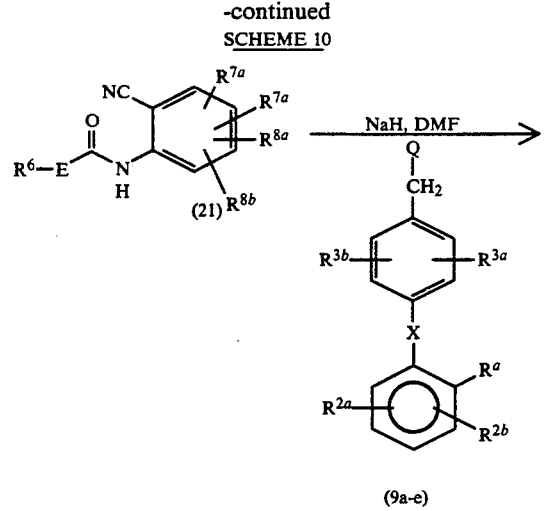

(21)
(9a-e)

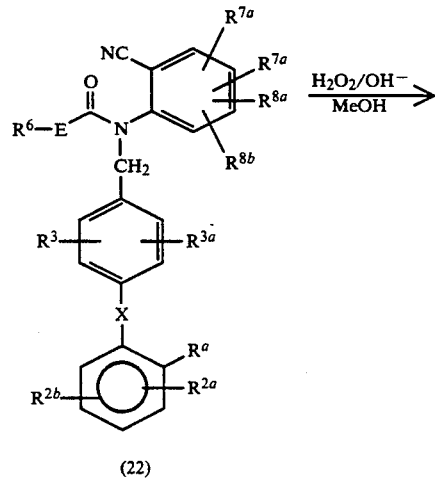

(22)

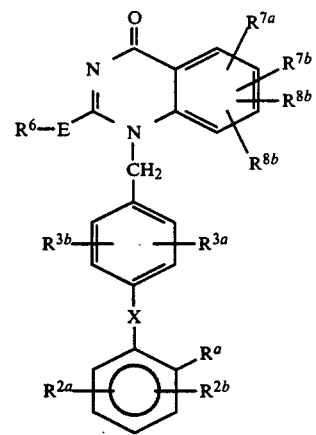

(20)

E = O or S

Scheme 11 illustrates the method by which a 2-amino-3-alkylquinazolinone 23 can be made. The 2-mercaptoquinazolinone (17) shown in Scheme 8 can be treated with sulfuryl chloride to give the corresponding 2-chloroquinazolinone 24.[12] Displacement of the chloride with an R[6] amine then gives 23 with E=NH.[13]

SCHEME 11

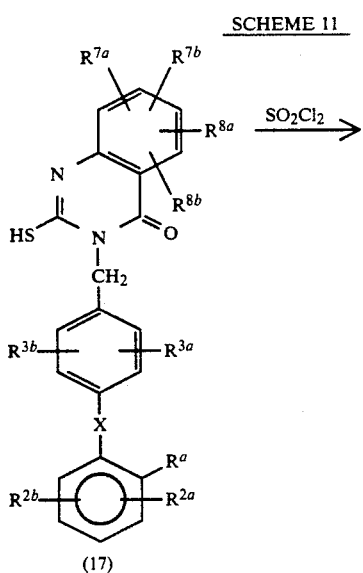

(17)

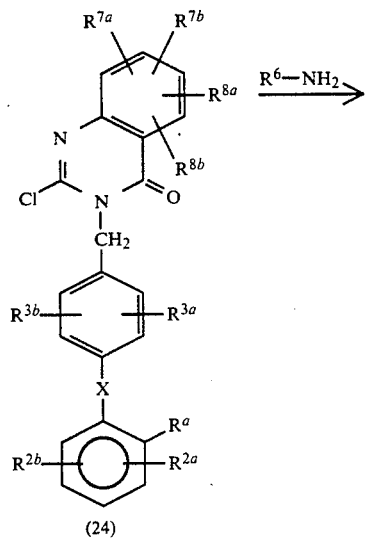

(24)

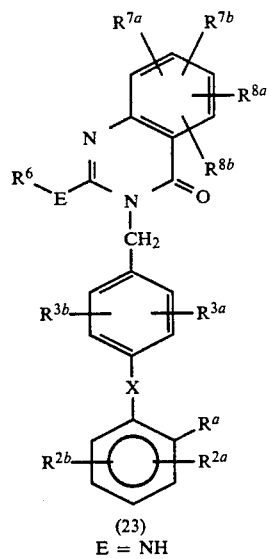

(23)
E = NH

Scheme 12 illustrates the method by which a 2-amino-1-alkylquinazolinone 25 can be made. The products from Scheme 10 where E is sulfur (20) can be used as a synthetic intermediate if the initial $R^6$ is a protecting group such as benzyl or t-butyl.[14] Deprotection and subjection of the resulting 2-mercapto-1-alkyl-quinazolinone to the same conditions used in Scheme 11 will result in the formation of the desired 2-amino-1-alkylquinazolinone. Alternatively, the sulfide may be displaced directly by an $R^6$ amine as shown in Scheme 13 ($R^6$—S— and $R^6$—NH$_2$ may or may not have the same $R^6$).

SCHEME 12

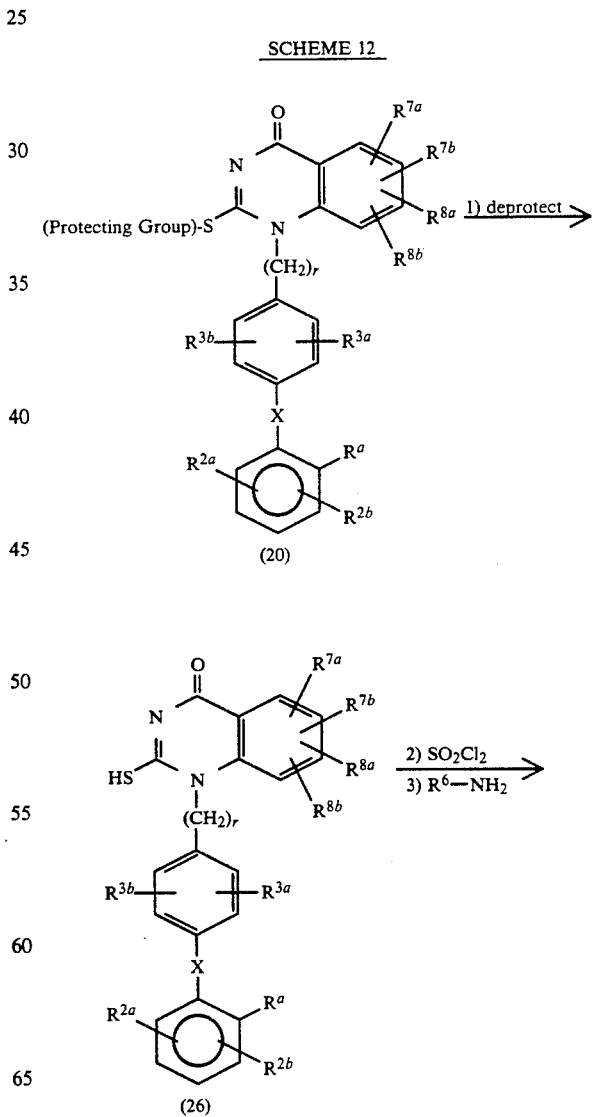

SCHEME 12 (continued)

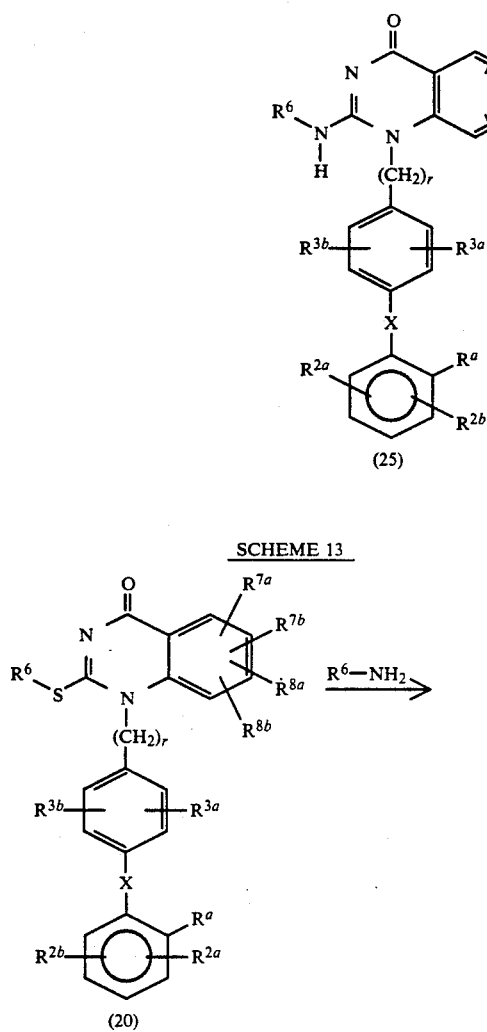

(25)

SCHEME 13

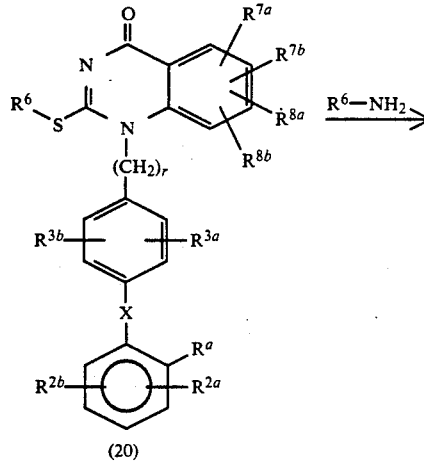

(20)

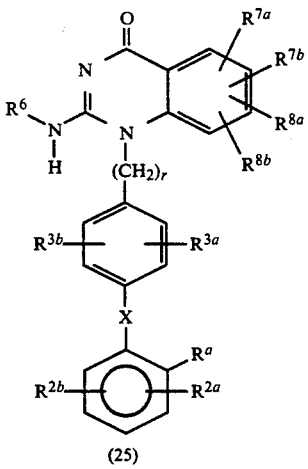

(25)

Scheme 14 illustrates the method by which a quinazolin-4(3H)-imine 27 may be prepared. A 3-substituted or unsubstituted quinazolin-4(3H)-one 28 can be converted to a quinazolin-4(3H)-thione 29 by the action of Lewesson's reagent. Addition of amine and heating will result in the formation of an imine 27 as shown.

SCHEME 14

(28)

(29) $\xrightarrow{R^{22}NH_2}$ (27)

$Z = -(CH_2)_r$ 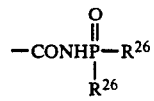 , H

Compounds of formula I where $R^1$ is $$-CONHP-R^{26}\atop R^{26}$$

may be prepared from the corresponding carboxylic acid derivatives (I) as outlined in Scheme 15. The carboxylic acid (I), obtained as described in Scheme 1, can be converted into the corresponding amide by treatment with carbonyldiimidazole and then with ammonia. The resulting amide then can be treated with sodium hydride or n-butyllithium in THF at $-20°$ C. followed by an appropriately substituted phosphonyl or phosphinyl halide to form the desired compounds (30).

SCHEME 15

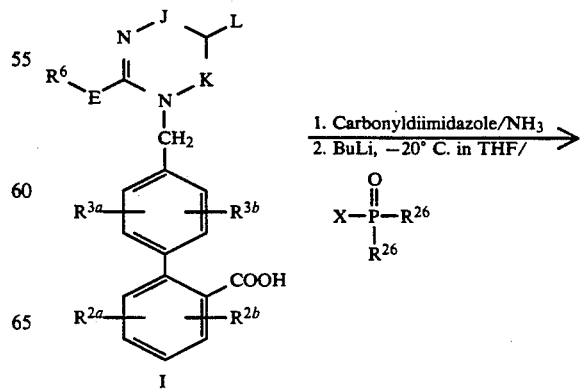

I

SCHEME 15 -continued

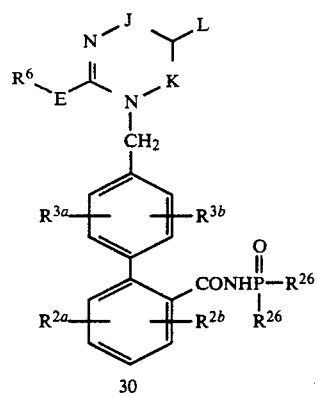

SCHEME 16 -continued

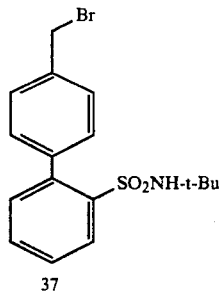

37 a. i) t-BuLi/ether, −78° C. ii) Me₃SnCl
b. i) NaNO₂/HCl ii) SO₂, CuCl₂ (iii) t-butylamine
c. Pd(PPh₃)₄, Toluene or (PPh₃)₂PdCl₂, DMF, Heat
d. NBS/CCl₄, AIBN, Reflux The biaryl sulfonamides (36) and (41), precursors for the alkylating agent 37, can be prepared from appropriate aryl-organotin precursors using palladium(0) catalyzed cross-coupling reactions [J. K. Stille, *Pure Appl. Chem.*, 57, 1771 (1985); T. R. Baiely, *Tetra Lett.*, 27, 4407 (1986); D. A. Widdowson and Y. Z. Zhang, *Tetrahedron*, 42, 2111 (1986)], as outlined in Schemes 16 and 17. The organotin compound (33) [S. M. Moerlein, *J. Organometallic Chem.*, 319, 29 (1987)], obtained from the aromatic precursors (35 or 36), may be coupled with aryl sulfonamide (39) using Pd(PPh₃)₄ or (PPh₃)₂PdCl₂ as catalysts to give biaryl sulfonamide 36. Similarly, the biphenylmethyl bromide (37) may be alternatively prepared from the appropriate organotin precursor (40) using the Pd(0) catalyzed cross-coupling reaction as outlined in Scheme 17.

SCHEME 16

SCHEME 17 a. t-BuMe₂Si—Cl/Imidazole, DMF
b. t-BuLi, −78° C., Me₃SnCl
c. Tetrabutylammonium fluoride
d. CBr₄/Ph₃P.

Compounds of formula I where R¹ is —SO₂N-HSO₂R²³ may be prepared from the key sulfonamide intermediate 42 as outlined in Scheme 18. The intermediate 42 may be prepared by the alkylation of appropriate heterocycles with the alkylating agent 37 as outlined in Scheme 1. Treatment of 42 with trifluoroacetic acid followed by acylation of the resulting sulfonamide 43 with appropriate sulfonyl chlorides may produce the desired compounds (44).

SCHEME 18

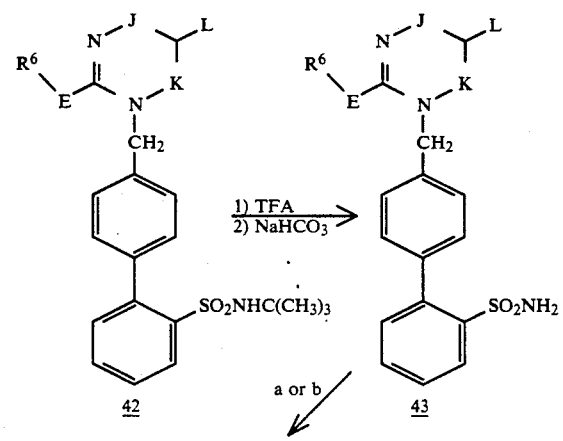

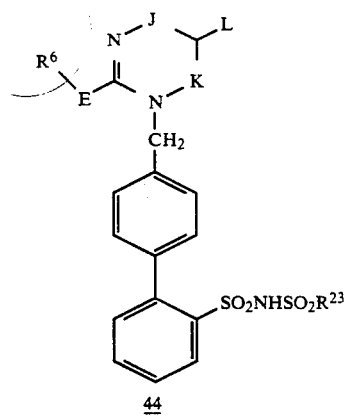

a. i) NaH/THF or DMF (ii) $R^{23}SO_2Cl$ b. $R^{23}SO_2Cl$, DBU, THF

Compounds of Formula (I) wherein $R^1$ is —$SO_2NH$-$CO_2R^{23}$ may be prepared by reacting an appropriate chloroformate with the sulfonamide (43) in pyridine or in the presence of DBU in THF to afford the desired compound (45), as outlined in Scheme 19.

SCHEME 19

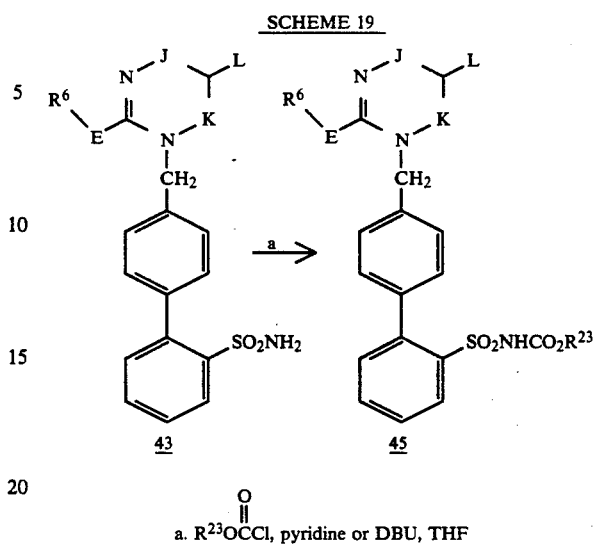

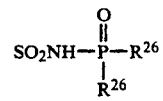

a. $R^{23}OCCl$, pyridine or DBU, THF

Compounds of Formula (I) wherein $R^1$ is $$SO_2NH-\underset{R^{26}}{\overset{O}{\underset{\|}{P}}}-R^{26}$$

may be prepared by treating sulfonamide (43) with n-butyllithium in THF followed by the treatment of the resulting anion with an appropriately substituted phosphonyl or phosphinyl halide to form the desired compounds (46). (Scheme 20)

SCHEME 20

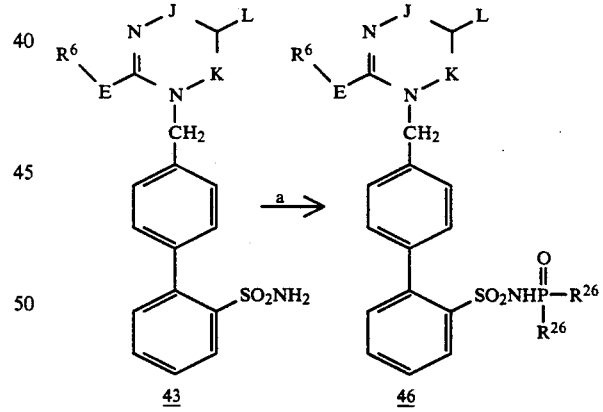

a. BuLi, −20° C. in THF/X—$\underset{R^6}{\overset{O}{\underset{\|}{P}}}R^{26}$

Compounds of Formula (I) wherein $R^1$ is $SO_2N$-$HSO_2N(R^4)(R^9)$ or

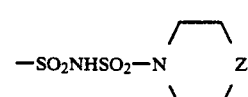

may also be prepared from sulfonamide (43) as outlined in Scheme 21. Treatment of 43 with n-butyllithium in THF at −25° C. and then with an appropriate sulfamoyl halide may produce the desired product (47) or (48).

SCHEME 21

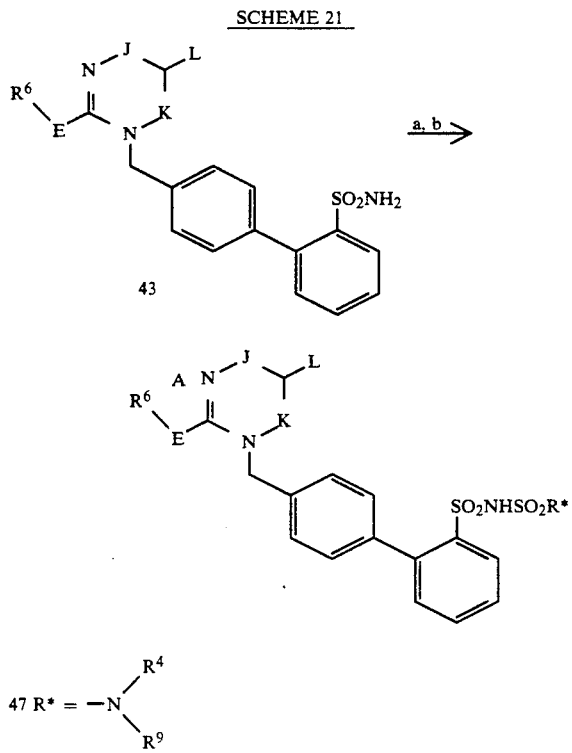

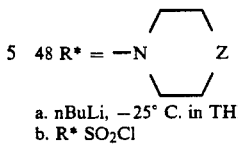

a. nBuLi, −25° C. in THF
b. R* SO₂Cl

Compounds of Formula (I) wherein $R^1$ is —NHSO₂NHSO₂$R^{23}$ or

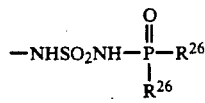

may be prepared from arylamine (50) as outlined in Scheme 22. The arylamine (50) obtained from the corresponding nitro compound 49 can be treated with t-butylsulfamoyl chloride to afford the protected amino sulfonamide (51). The amino sulfonamide (52) obtained after removal of the t-butyl protecting group may then be reacted with an appropriate acylating agent in the presence of a base such as pyridine or DBU in an organic solvent such as THF or DMF to form the desired products (53a) or (53b).

Compounds of the Formula (I) wherein $R^1$ is —NHSO₂$R^{23}$ may be prepared by the reaction of an appropriate sulfonyl halide ($R^{23}$SO₂Cl) or sulfonyl imidazole derivative with the aryl amine 50 in the presence of an appropriate base such as pyridine, triethylamine or DBU.

SCHEME 22

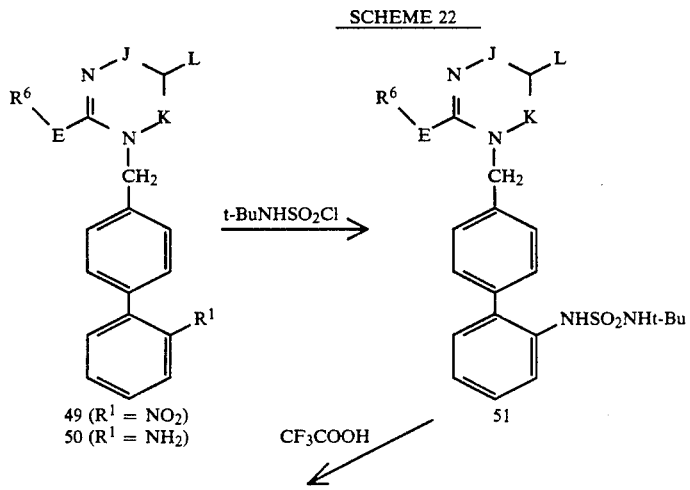

SCHEME 22

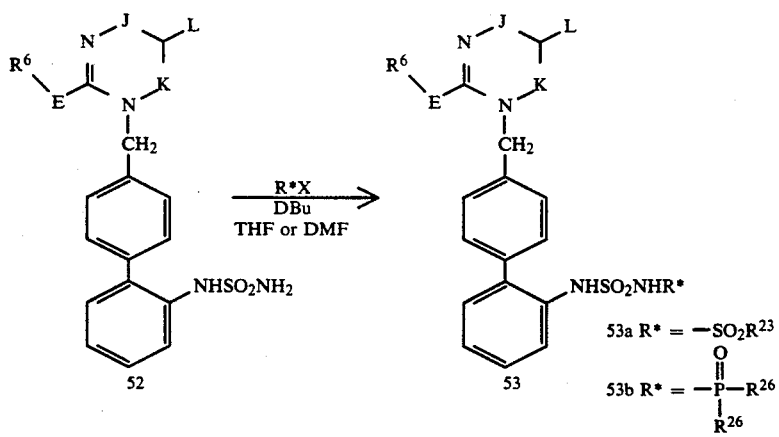

53a R* = —SO$_2$R$^{23}$

53b R* = —P(=O)(R$^{26}$)R$^{26}$

Compounds of Formula (I) and the benzyl halides of the formula (59) wherein R$^1$ is 1,2,3,5-oxathiadiazole-2-oxide may be prepared from the corresponding cyano derivative (54) or cyano precursor (8b) as outlined in Schemes 23 and 24, respectively utilizing procedures described in U.S. Pat. No. 4,910,019. The cyano derivatives (54), obtained as described in Scheme 1, can be converted into the corresponding amidoxime (55) by treatment with hydroxylamine hydrochloride and sodium methoxide in an organic solvent, such as methanol or DMSO. The amidoxime (55) then can be treated with base and thionyl chloride in an aprotic solvent to form the desired 1,2,3,5-oxathiadiazole-2-oxide (56). Similarly, the oxathiadiazole-2,2-dioxide 56 a can be prepared by treatment of amidoxime 66 with a base and sulfuryl chloride. As shown in Scheme 23, the cyano precursor (8b) may be converted into the desired 1,2,3,5-oxathiadiazole (59) which is then protected with the trityl group prior to the formation of the desired benzyl halide (59). The protecting group is removed subsequent to the alkylation of heterocycle (1) to give the desired product (56).

SCHEME 23

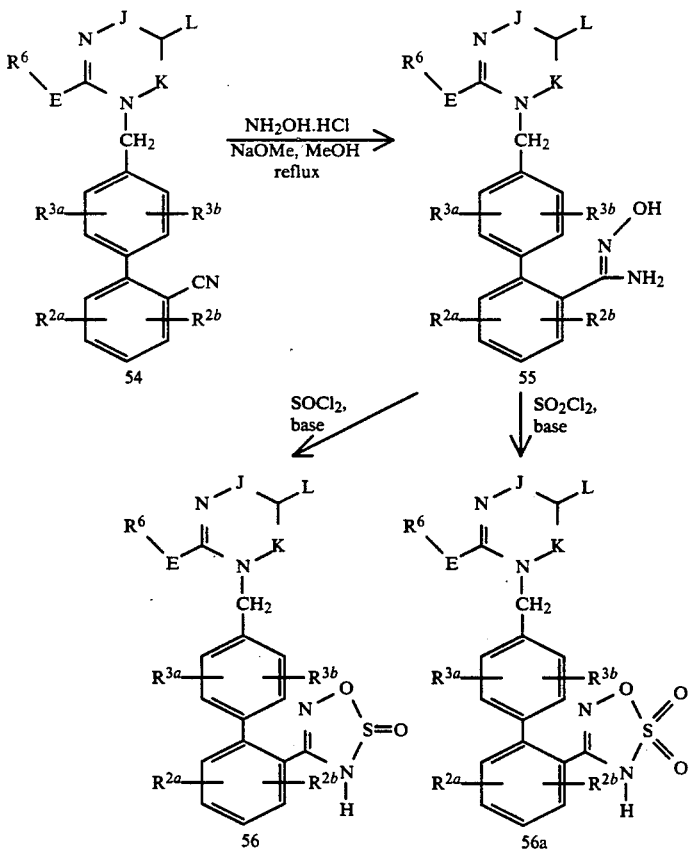

SCHEME 24

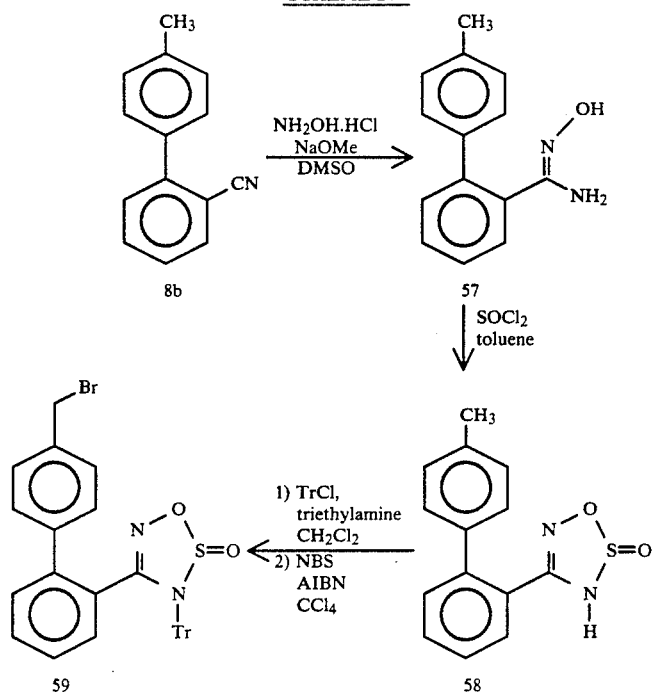

Compounds of Formula (I) and the benzyl halides of the formula (3) wherein $R^1$ is 1,2,3,5-thiatriazole-1-oxide may be prepared from the corresponding precursors 60 or 65 as outlined in Schemes 25 and 26, respectively. Intermediate 65 may be prepared from the biphenyl 8a according to the scheme illustrated (see procedures in U.S. Pat. No. 4,870,186). Intermediates (61) and (66) can be treated with $SOCl_2$ (see procedures in: *Ber. Deutsch. Chem. Ges.* 1971, 104 pp 639) to give intermediates, (62) and (67). Bromination of the N-protected compounds (62) and (67) provides intermediates 64 and 68 respectively. After alkylation with an appropriate heterocycle, the trityl group of the intermediate derived from 64 is removed with protic acid and the cyanoethyl group of the intermediate derived from 68 is removed upon treatment with hydroxide. Alternatively, (64) and (68) may be prepared as shown in Scheme 27 and 28. Treatment of (65) with $SOCl_2$ (see procedures in: *Ber. Deutsch. Chem. Ges.* 1971, 104 pp 639) provides (70), which under mild hydrolytic conditions provides (62). The conversion of (62) to (64) is as described for Scheme 25. Alkylation of the trityl protected analog (71) by treatment with a base such as NaH and an alkyl halide would provide (64), which then may be converted to (68) as previously described.

SCHEME 25

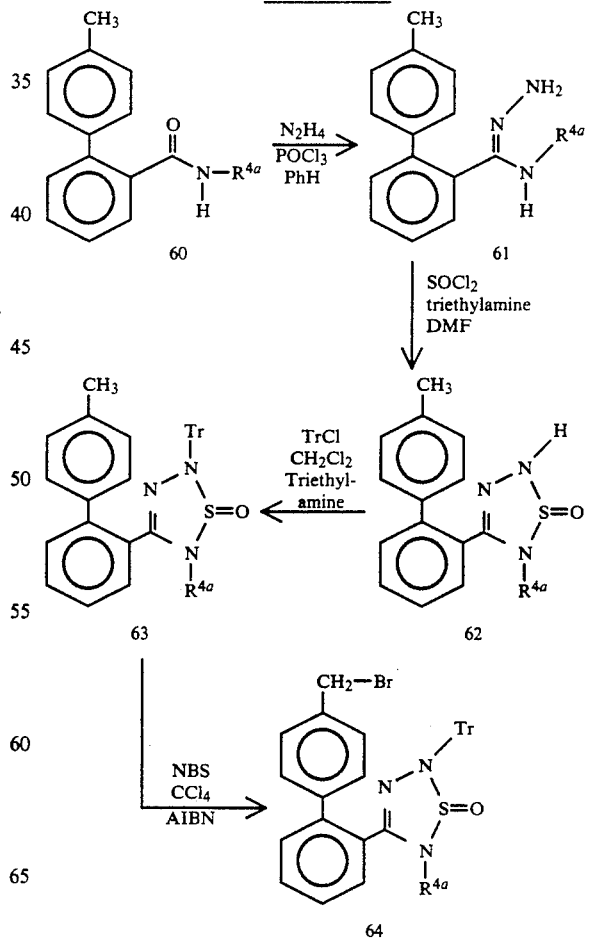

5,238,942
SCHEME 26
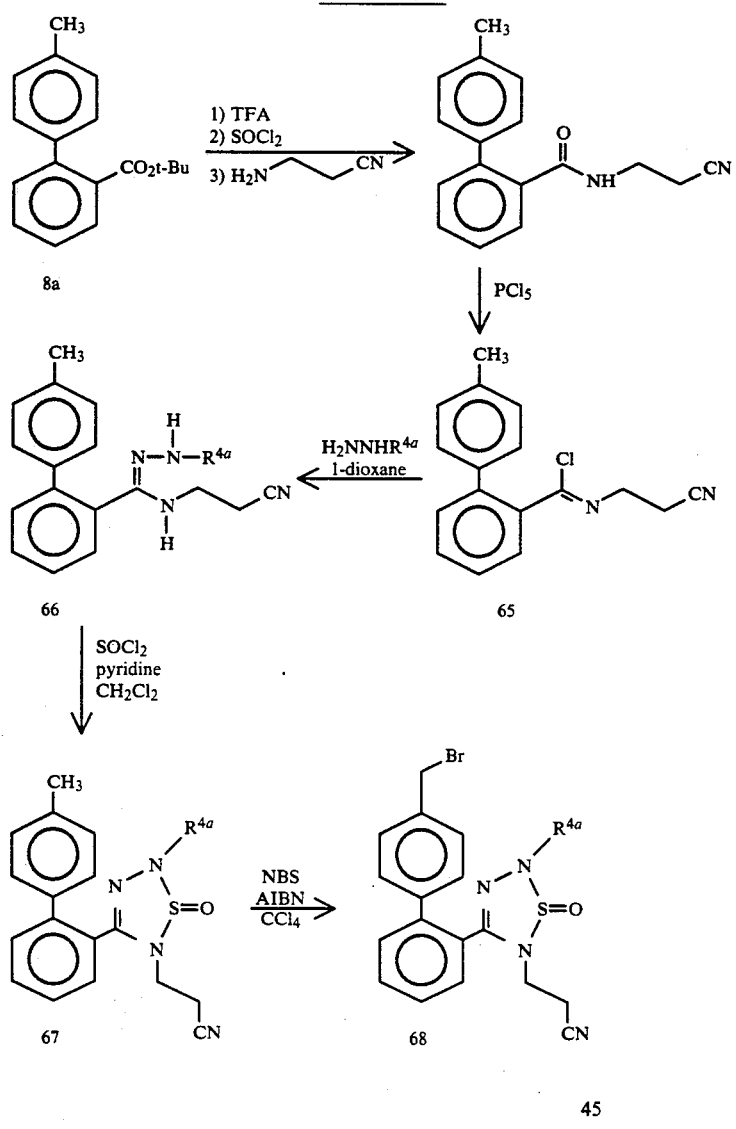
SCHEME 27
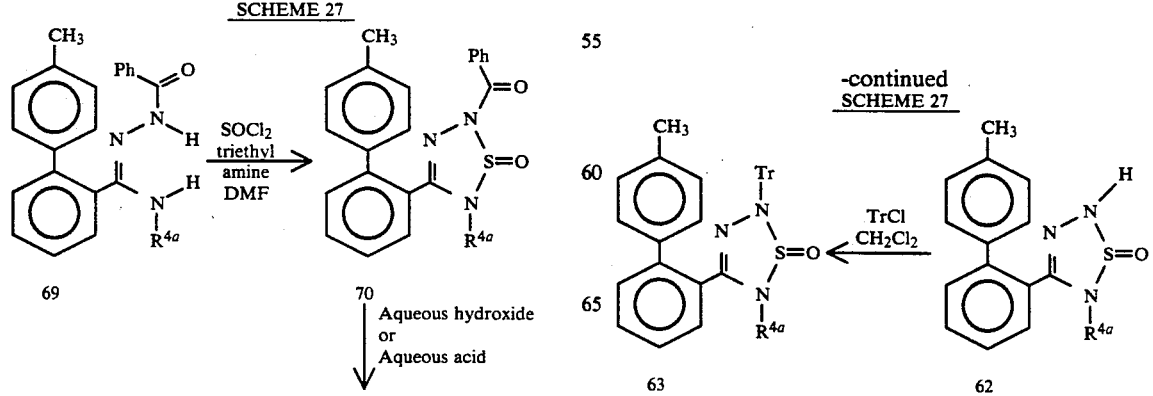

SCHEME 27

-continued

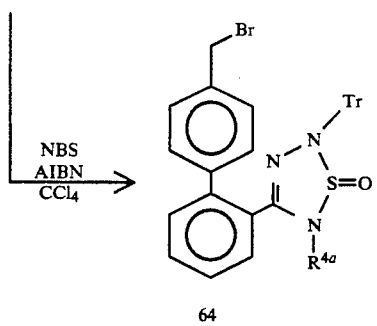

64

SCHEME 28

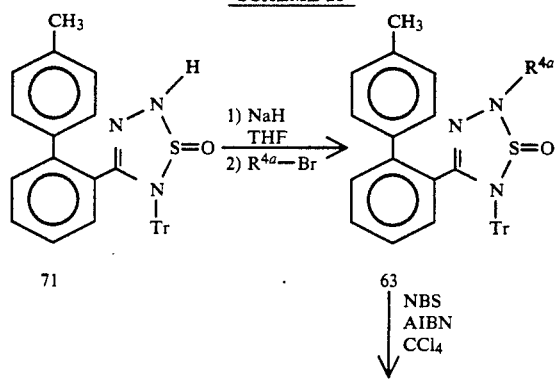

SCHEME 28

-continued

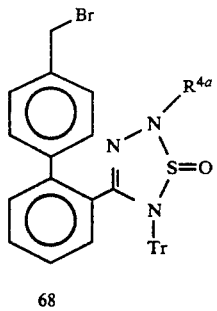

68

Compounds of Formula (I) and the benzyl halides of formula (2) wherein $R^1$ is 1,2,3,5-thiatriazole-1,1-dioxide-4-yl may be prepared using procedures described in *Monatsh. Chem.*, 1985, 116, pp 1321 and described herein. Sequential treatment of intermediates such as (65) or (61) with n-BuLi and $SO_2F_2$ will provide the 1,2,3,5-thiatriazol-1,1-dioxide analogs of (62) and (66). Further elaboration of the afore mentioned analogs by the methods described for the conversion of (62) to (66) in Scheme 25 and the methods described for the conversion of (66) to (68) in Scheme 26 would give the benzyl halides of formula (2) wherein $R^1$ is 2-triphenylmethyl-1,2,3,5-thiatriazole-1,1-dioxide-4-yl and 5-triphenylmethyl-1,2,3,5-thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (8c) as outlined in Scheme 29. The amino compound 72 obtained from 8c may be reacted with t-butyl sulfamoylchloride to form the intermediate 73, which then can be alkylated with an appropriate bromoacetic acid derivative to give 74. Treatment of 74 with trifluoroacetic acid followed by the treatment with an appropriate base such as sodium or potassium alkoxide may produce the desired compound 75, which can be elaborated further to give the key alkylating agent 77 as outlined in the scheme. Alkylation of an appropriate heterocyclic compound with 77 may then furnish the desired antagonist.

SCHEME 29

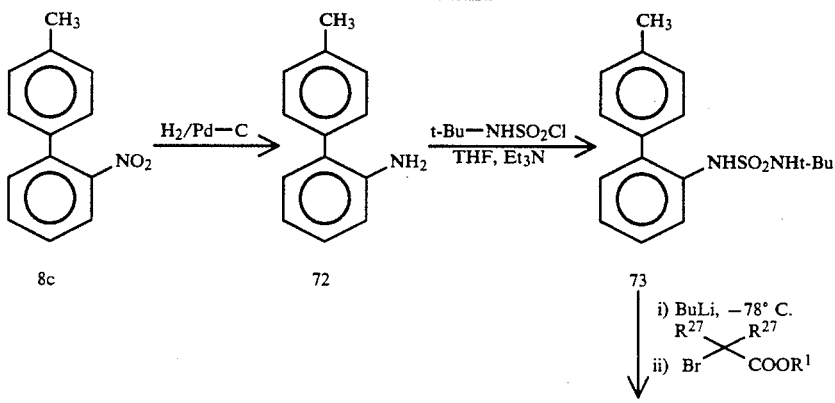

SCHEME 29

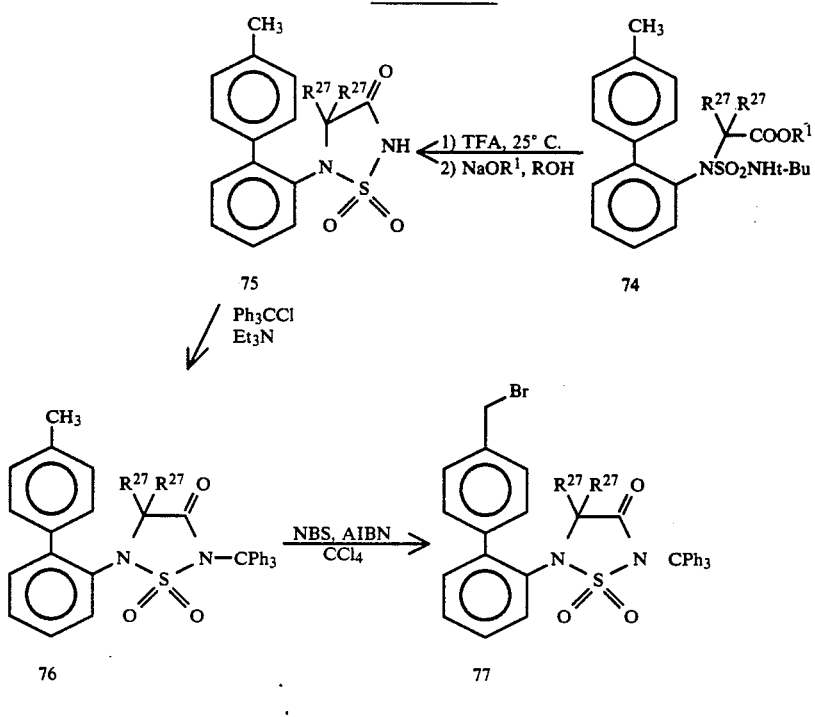

Compound of Formula (I) wherein $R^1$ is 5-aminosulfonyl-1,2,4-oxadiazole may be prepared using the bromomethyl biphenyl derivative 81 and an appropriate heterocyclic compound. The synthesis of 81 can be accomplished as outlined in Scheme 30. The amidoxime 57 may be reacted with S-methylisothiourea to form the 5-amino-1,2,4-oxadiazole 78, which can be then treated with an appropriate sulfonylchloride to give the corresponding 5-aminosulfonyl-1,2,4-oxadiazole 79. The appropriately protected derivative 80 then can be brominated to form the desired alkylating agent 81.

SCHEME 30

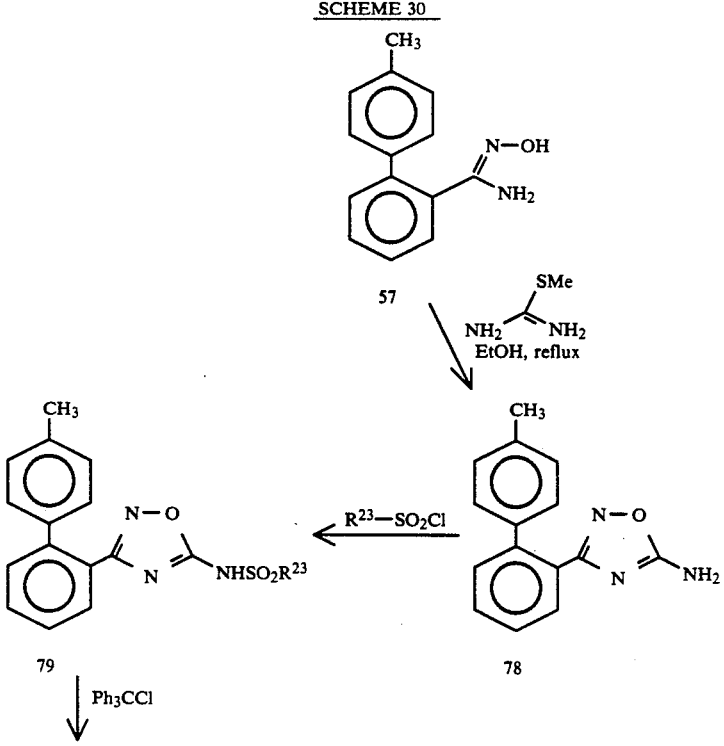

SCHEME 30

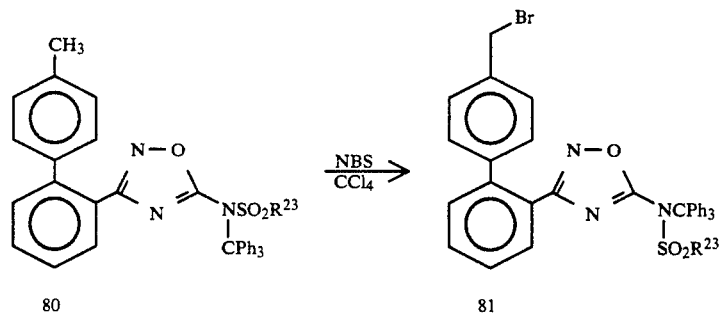

Compounds of Formula (I) wherein $R^1$ is 3-aminosulfonyl-1,2,4-oxadiazole can be prepared starting from the carboxylate derivative (8a) as outlined in Scheme 31. The ester derivative 82 obtained from 8a is treated with N-hydroxy guanidine sulfate in the presence of an alkoxide base to form the 3-amino-1,2,4-oxadiazole derivative 83, which may be reacted with an appropriate sulfonyl chloride to give the 3-aminosulfonyl-1,2,4-oxadiazole compound 84. The compound 85 can be prepared from 84 as outlined in Scheme 31.

SCHEME 31

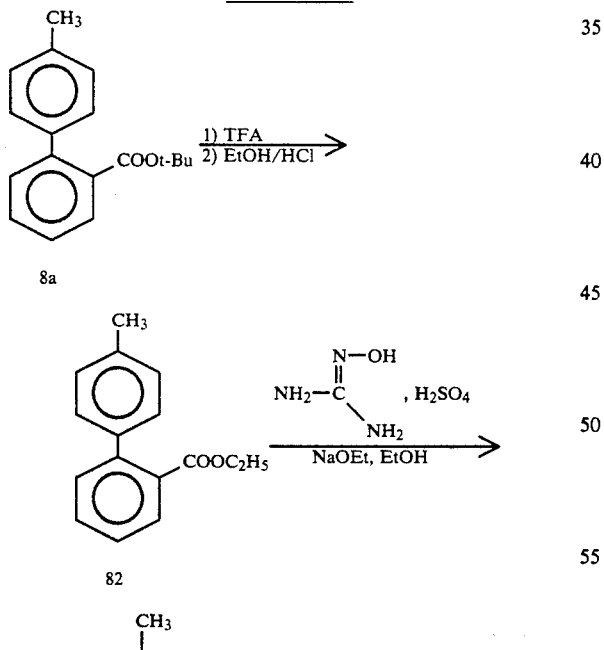

-continued SCHEME 31

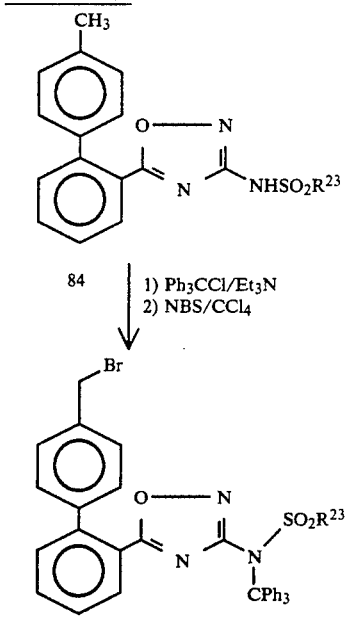

Compounds of Formula (I) and the benzyl halides of formula (2) wherein $R^1$ is 1,2,3-oxathiazin-4(3H)-one-2,2-dioxide-6-yl may be prepared as outlined in Scheme 32. As shown and according to procedures in Angew. Chem. Int. Edn., (1973), 12, pp 869, the betaketoester (86) is treated with fluorosulphonyl isocyanate, heated to extrude $CO_2$ and iso-butene, then treated with base such as KOH to form the oxathiazolinone dioxide intermediate (87). Treatment of (87) with triphenylmethyl chloride and triethylamine in $CH_2Cl_2$ gives (88) which in turn is converted to benzyl halide (89) by treatment with N-bromosuccinimide, AIBN, in $CCl_4$ at reflux.

SCHEME 32

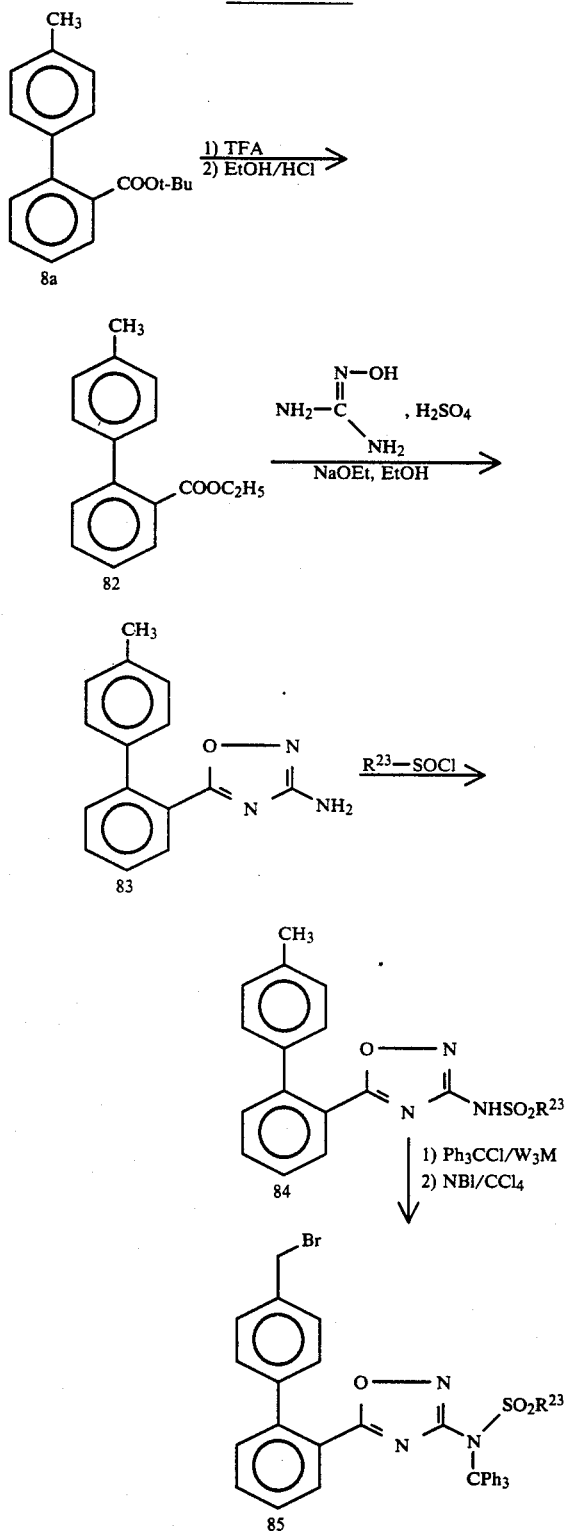

Compounds of Formula (I) wherein R¹ is oxamic acid may be prepared utilizing procedures described in *J. Med. Chem.*, 1981, 24, pp 742-748 and as outlined in Scheme 33. The amine (50) is reacted with ethyl oxalyl chloride in the presence of a base such as pyridine or triethylamine and a solvent such as $CH_2Cl_2$ to form the intermediate oxalyl ester which is subsequently saponified with hydroxide to form oxamic acid (90).

SCHEME 33

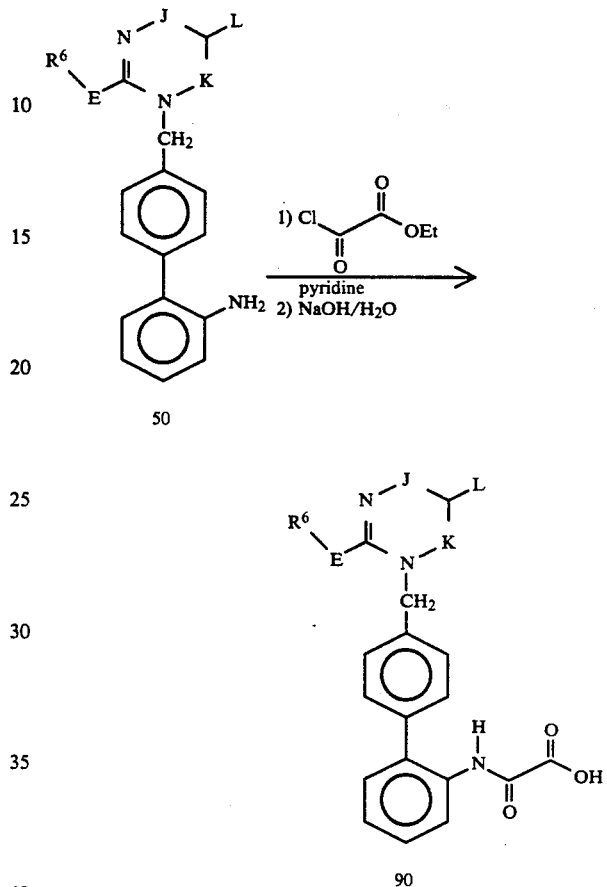

compounds of Formula (I) wherein R¹ is $-SO_2NR^{25}OR^{25}$ may be prepared as outlined in Scheme 34. The key intermediate 93 is prepared by the reaction of an appropriate heterocyclic compound (1), preferably as an alkali metal salt, with the alkylating agent 91 (prepared from 40). The compound 95, prepared from the sulfonyl chloride 94 and O-t-butylhydroxylamine, is then reacted with 93 in the presence of a Pd(0) catalyst to give 96. Removal of the t-butyl protecting group produces the desired N-hydroxy sulfonamide 97.

SCHEME 34

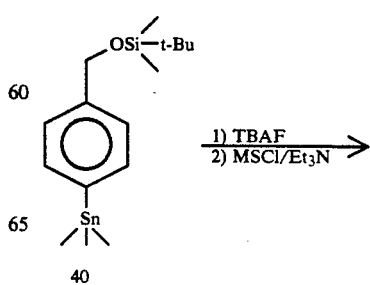

-continued

SCHEME 34

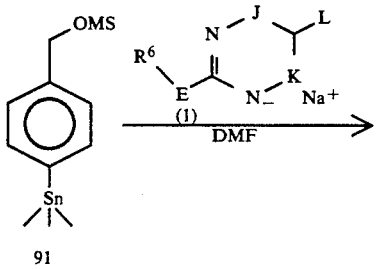

91

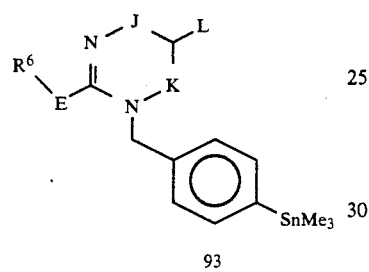

93

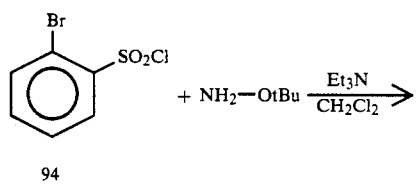

94

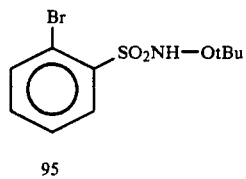

95

93
+    Pd(PPh₃)₂Cl₂
95   ───────────→
     DMF or THF,
     Heat

-continued

SCHEME 34

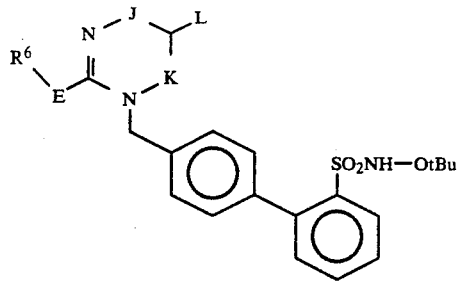

96

TFA
25° C.

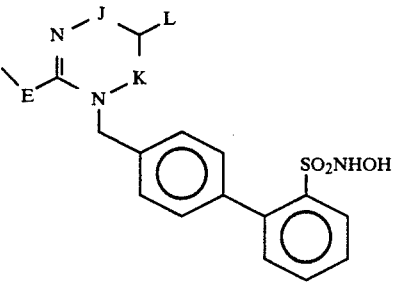

97

Further functionalization of compounds of Formula 1 where $R^{8a}$ or $R^{8b}$ is nitro is available through the following route (Scheme 35). The nitro group of 98 may be reduced to the amine 99 by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates 100. The amine reacts slowly with isocyanates to give ureas 101. Trisubstituted ureas 102 may be prepared from the benzyl carbamate 100 ($R^{23}$=benzyl) by treatment with the magnesium salt of a secondary amine. The amine may be further derivatized or converted to other groups by means of chemical procedures well known to those skilled in the art.

SCHEME 35
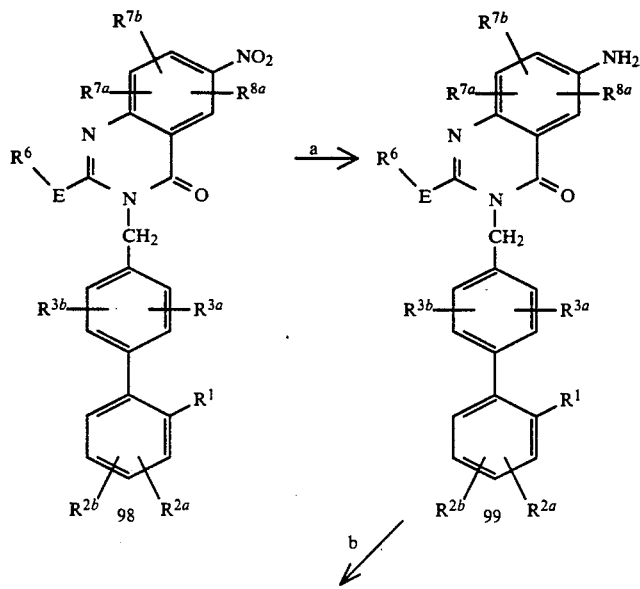
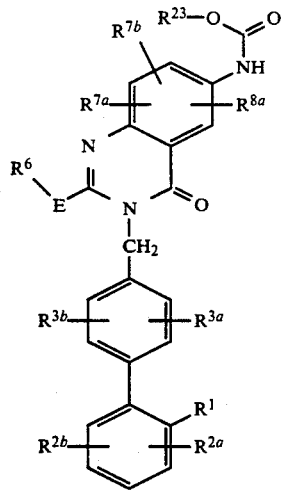
100

SCHEME 35

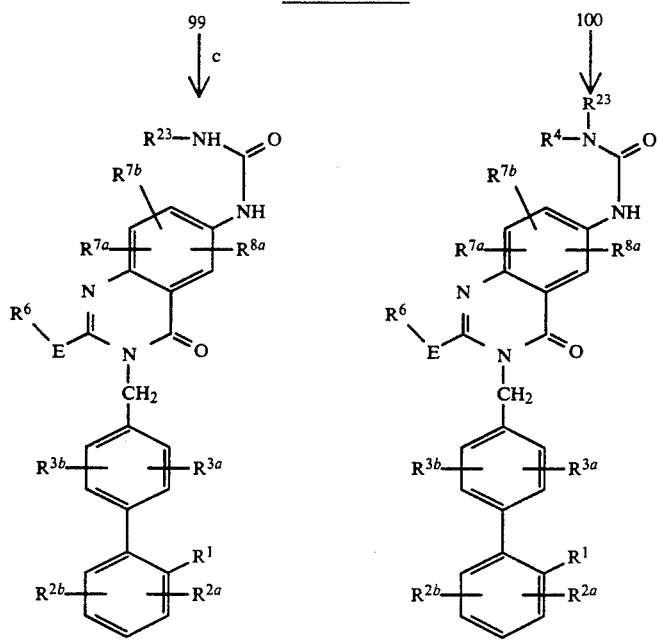

$^a$H$_2$, 10% Pd/C, EtAc
$^b$NaH, ClCOR$^{23}$, DMF
$^c$R$^{23}$NCO, CH$_2$Cl$_2$
$^d$MeMgBr, R$^4$NHR$^{23}$, THF, reflux

ADDITIONAL REFERENCES CITED IN SCHEMES

E. C. Taylor, R. J. Knopf, A. L. Borror, *J. Am. Chem. Soc.* (1960) 82, 3152.

R. L. McKee, M. K. McKee, R. W. Bost, *J. Am. Chem. Soc.* (1946) 68, 1902.

A. Khan, R. K. Saksena, *Pharmazie* (1988) 43 H. 12.

M. T. Bogert, W. F. Hand, *J. Am. Chem. Soc.* (1906) 28, 94.

See A. Khan, reference 1.

L. A. Errede, J. J. McBrady, H. T. Oien, *J. Org. Chem.* (1977) 42, 656.

L. A. Errede, *J. Org. Chem.* (1976) 41 1763.

L. A. Errede, H. T. Oien, D. R. Yarian, *J. Org. Chem.* (1977) 42, 12.

K. Wunsch, A. J. Boulton, *Adv. Het. Chem.* (1967) 8, pp 326–9, and references therein.

I. R. Gambhir, S. S. Joshi, *J. Ind. Chem. Soc.* (1964) 41, 47.

Bayley, Stranding, Knowles, *Tetrahedron. Lett.* (1978) 3633.

Rolla, *J. Org. Chem.* (1982) 47, 4327.

Gibson, Bradshaw, *Angew, Chem, Int. Ed. Engl.* (1968) 7, 919.

R. G. Dave, G. S. Mewada, G. C. Amin, *J. Ind. Chem. Soc.* (1960) 37, 595.

J. E. McCarty, E. L. Haines, C. A. VanderWerf, *J. Am. Chem. Soc.* (1960) 82, 964.

P. N. Bhargava, P. Ram, *Bull. Chem. Soc. Jap.* (1965) 38, 342.

M. R. Chaurasia, A. K. Sharma, *Heterocycles* (1983) 20, 1549.

K. Lempert, G. Doleschall, *Chem Ber.* (1963) 96, 1271.

H. Singh, K. S. Narang, *J. Ind. Chem. Soc.* (1963) 40, 545.

M. S. Dhatt, K. S. Narang, *J. Ind. Chem. Soc.* (1954) 31, 787.

M. S. Dhatt, K. S. Narang, *J. Ind. Chem. Soc.* (1954) 31, 864.

D. S. Bariana, H. S. Sachdev, K. S. Narang, *J. Ind. Chem. Soc.* (1955) 32, 647.

Griess, *Ber. Deut, Chem. Ges.* (1869) 2, 415.

N. A. Lang, F. E. Shiebley, *J. Am. Chem. Soc.* (1933) 55, 1188.

H. B. Milne, S. L. Razniak, R. P. Bayer, D. W. Fish, *J. Am. Chem. Soc.* (1960) 82, 4582.

E. J. Corey, M. G. Bock, A. P. Kozikowski, A. V. R. Rao, D. Floyd, B. Lipshutz, *Tetrahedron Lett.* (1978) 1051.

M. Bergmann, L. Zervas, *Ber.* (1932) 65 1192.

R. L. Dannley, M. Lukin, *J. Org. Chem.* (1957) 22, 268.

R. Zibuck, N. J. Liverton, A. B. Smith, *J. Am. Chem. Soc.* (1986) 10,8 2451.

D. J. Brown, *Fused Pyrimidines*, Part I Quinazolines, (1967), J. Wiley & Sons, p. 222.

D. J. Brown, *Fused Pyrimidines*, Part I Quinazolines, (1967), J. Wiley & Sons, p. 323.

T. W. Greene, *Protective Groups in Organic Synthesis*, (1981), J. Wiley & Sons, pp. 193–217.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, $R^1$ as carboxyl is often protected as its t-butyl ester which in the last step is removed by treatment with trifluoroacetic acid.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

RECEPTOR BINDING ASSAY USING RABBIT AORTAE MEMBRANE PREPARATION

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^{125}$I-Sar$^1$Ile$^8$-angiotensin II is presented as a measure of the efficacy of such compounds as AII antagonists.

RECEPTOR ASSAY USING BOVINE ADRENAL CORTEX PREPARATION

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^3$H-angiotensin II is presented as a measure of the efficacy of such compounds as AII antagonists.

RECEPTOR ASSAY USING RAT BRAIN MEMBRANE PREPARATION

Membranes from rat brain (thalamus, hypothalamus and midbrain) are prepared by homogenization in 50 mM Tris HCl (pH 7.4), and centrifuged at 50,000×g. The resulting pellets are washed twice in 100 mM NaCl, 5 mM $Na_2$•EDTA, 10 mM $Na_2HPO_4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$•EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$,Ile$^8$-angiotensin II (23–46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an $IC_{50}<50$ μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down the spinal column. The rats are immediately placed on a Harvard Rodent Ventilator (rate-60 strokes per minute, volumn-1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer. Chemical shifts are reported as (parts per million) downfield from tetramethyl silane. Mass spectra were obtained from the Merck and Co. mass spectral facility in Rahway N. J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of dry nitrogen under standard conditions for those skilled in the art.

PREPARATION OF BIPHENYL SYNTHETIC INTERMEDIATES:

EXAMPLE 1

2-t-Butoxycarbonyl-4'-methylbiphenyl

To a solution of p-bromotoluene (30 g) in dry ether (150 ml) at $-78°$ C., a solution of t-BuLi in pentane (1.7M) (210 ml) was added slowly over a period of 1.5 hours, using a dropping funnel. The bath was than removed and the mixture was stirred at room temperature for an additional 2 hours. The content of the flask was then added slowly (using a cannula) at room temperature to a premixed solution of $ZnCl_2$ in ether (1M, 180 ml) and dry THF (360 ml). The mixture was stirred for 2 hours at that temperature and then the slurry was added (using a cannula) to a solution of 2-t-butoxycarbonyl iodobenzene (35.6 g) and $NiCl_2(Ph_3P)_2$ (2.1 g) in dry THF (360 ml). The mixture, after stirring at room temperature overnight (18 hours), was poured slowly under stirring into ice-cold 0.5N HCl (1500 ml). The organic layer was separated, and the aqueous phase was extracted with ether (3×300 ml). The combined organic layer was washed with water, brine and then dried over $MgSO_4$. Removal of the solvent gave the crude product as an oil (32 g). The material was purified on a silica-gel flash column using ethyl acetate-hexane (1:12) to give the titled compound as an oil (24 g, 76%). $^1$H NMR ($CDCl_3$): δ1.24 (s,9H), 2.42 (s,3H), 7.2–7.8 (m,8H); FAB-MS: m/e 269(M+H).

EXAMPLE 2

4-Bromomethyl-2'-t-butoxycarbonylbiphenyl

To a solution of 2-t-butoxycarbonyl-4'-methylbiphenyl (25.3 g, 95 mmol) in $CCl_4$ (200 ml) were added freshly opened N-bromosuccinimide (17.6 g, 0.099 mole) and dibenzoyl peroxide (2.28 g, 0.0094 moles). The mixture was refluxed for 4 hours, cooled to room temperature and filtered. The filtrate was washed with sat. $NaHSO_3$ (1×50 ml), sat. $NaHCO_3$ (1×50 ml), water (1×50 ml), sat. NaCl (1×50 ml) and dried over $MgSO_4$. The solution was filtered, and concentrated in vacuo. The residue was dissolved in 100 ml of hot hexane. Crystallization gradually took place as the solution cooled. The flask was finally cooled to $-20°$ C. and the precipitate recovered by filtration. The solid was washed with ice cold hexanes and dried in vacuo to give 27 g (88%) of a white solid. $^1$H-NMR ($CDCl_3$): 1.23 (s, 9H), 4.53 (s, 2H), 7.2–7.5 (m, 7H), 7.68 (d, 1H).

EXAMPLE 3

2-Cyano-4'-methylbiphenyl

To a solution of p-bromotoluene (30 g) in dry ether (150 ml) at $-78°$ C., a solution of t-BuLi in pentane (1.7M) (210 ml) was added slowly over a period of 1.5 hours, using a dropping funnel. The bath was then removed and the mixture was stirred at room temperature for an additional 2 hours. The contents of the flask was then added slowly (using a cannula) at room temperature to a premixed solution of $ZnCl_2$ in ether (1M) (180 ml) and dry THF (360 ml). The mixture was stirred for 2 hours at that temperature and then the slurry was added (using a cannula) to a solution of 2-bromobenzonitrile (21.3 g) and $NiCl_2(Ph_3P)_2$ (2.1 g) in dry THF (300 ml). The mixture, after stirring at room temperature overnight (18 hours), was poured slowly under stirring into ice-cold 1N HCl (1500 ml). The organic layer was separated, and the aqueous phase was extracted with ether (3×300 ml). The combined organic layer was washed with water, brine and then dried over $MgSO_4$. Removal of the solvent gave the crude product as a semisolid mass (34 g). The material was purified on a silica-gel flash column using ethyl acetate-hexane (1:12) to give the desired nitrile as a low-melting solid (28 g, 88%). $^1$H-NMR ($CDCl_3$): 2.42 (s, 3H), 7.2–7.8 (m, 8H); FAB-MS: m/e 194 (M++1).

EXAMPLE 4

4-Bromomethyl-2'-nitrobiphenyl

Step 1: 4-Methyl-2'-nitrobiphenyl

A 1 L three-necked 24/40 round-bottom flask equipped with a mechanical stirrer, a 250 mL constant pressure addition funnel with a nitrogen inlet at the top, and a spetum was flame dried, cooled and then charged with a solution of 29.07 g (0.17 mol) of p-bromotoluene in 100 mL of anhydrous tetrahydrofuran under a nitrogen atmosphere. The solution was stirred and cooled to $-78°$ C. and 200 mL (0.34 mol) of a 1.7M solution of t-butyllithium in pentane was added via the addition funnel over 30 minutes. When the addition was complete, the cooling bath was removed and the reaction mixture was stirred for 30 minutes and allowed to warm to room temperature. The dropping funnel was next charged with 170 mL (0.17 mol) of a 1.0M solution of zinc chloride in diethylether which was added to the reaction mixture over a 10 minute period. A separate 1

L three-necked 24/40 round-bottom flask equipped with a mechanical stirrer, a nitrogen inlet and a septum, was flame dried, cooled and then charged with 4.04 g (6.0 mmol) of bis(triphenylphosphine)palladium(II) chloride and 50 mL of anhydrous tetrahydrofuran under a nitrogen atmosphere. The stirrer was started and 8.0 mL of a 1.5M solution (12 mmol) of diisobutylaluminum hydride in toluene was added to the suspension via syringe. The catalyst was stirred an additional 10 minutes at room temperature, and then a solution of 23.23 g (0.115 mol) of 1-bromo-2-nitrobenzene in 100 mL of anhydrous tetrahydrofuran was added. The suspension of the tolylzinc chloride was then transferred to the second flask via a wide diameter cannula. The reaction mixture was stirred an additional 45 minutes at room temperature, then most of the tetrahydrofuran was removed on a rotary evaporator. The resulting oil was partitioned between ethyl acetate and 1.0N hydrochloric acid. The organic layer was washed successively with water and brine, then dried (MgSO$_4$), filtered and evaporated. The residual oil was purified on a silica gel flash chromatography column eluted with 10% ethyl acetate-hexane to afford after evaporation and drying in vacuo the product as a viscous yellow oil: $^1$H-NMR (CDCl$_3$): δ2.36 (s, 3H), 7.16–7.24 (m, 4H), 7.38–7.46 (m, 2H), 7.55–7.62 (m, 1H), 7.80 (d, J=10 Hz, 1H); MS (FAB) m/e 214 (MH+).

Step 2: 4-Bromomethyl-2'-nitrobiphenyl

A 2 L 24/40 three necked round-bottom flask equipped with a mechanical stirrer, a reflux condenser and a stopper, was charged with 15.427 g (72 mmol) of 4-methyl-2'-nitro[1,1'-biphenyl], 1.2 L of carbon tetrachloride, 14.164 g (80 mmol) of N-bromosuccinimide, and 0.50 g of 2,2'-azobis(2-methylpropionitrile). The stirred reaction mixture was refluxed under a nitrogen atmosphere for 4 hours, then cooled to room temperature and filtered. The filtrate was evaporated in vacuo and the residual oil was purified on a silica gel flash chromatography column eluted with 10% ethyl acetate-hexane. Evaporation of the pure fractions afforded the product as a yellow crystalline solid which had: mp 109°–110° C.; $^1$H-NMR (CDCl$_3$): δ4.52 (s, 2H), 7.24–7.30 (m, 2H), 7.40–7.52 (m, 4H), 7.58–7.65 (m, 1H), 7.86 (d, J=10 Hz, 1H); MS (FAB) m/e 294 (MH+).

EXAMPLE 5

2-Cyano-4-fluoro-4'-methylbiphenyl

A solution of p-tolyltrimethyltin (1.26 g; 4.96 mmol) in dry toluene (8 mL) was degassed with a stream of N$_2$ for ca. 5 min. To this solution under N$_2$ was added 2-bromo-5-fluorobenzonitrile (0.901 g; 4.51 mmol) and Pd(PPh$_3$)$_4$ (260 mg; 5 mol%). The reaction was stirred at reflux under N$_2$ for 12 hr and then cooled to room temperature. The reaction mixture was filtered through a pad of celite and the filtrate was concentrated in vacuo. The product was purified by flash chromatography on a silica gel column, eluting with Hex/CH$_2$Cl$_2$ to afford the title compound as a slightly yellow solid.

$^1$H-NMR (300 MHz, CDCl$_3$): δ2.40 (s, 3H), 7.28 (d, 2H), 7.34 (dd, 1H), 7.40 (d, 2H), 7.44 (t, 1H), 7.46 (dd, 1H); MS (FAB) m/e 211 (M+, calcd for C$_{14}$H$_{10}$NF, 211).

EXAMPLE 6

4'-Bromomethylbiphenyl-2-tert-butyl-sulfonamide

Step 1: 2-bromobenzene(tert-butyl)-sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tertbutyl)sulfonamide as a white solid; $^1$H NMR (300 MHz, CDCl$_3$) δ8.18 (d, J=8.5 Hz, 1H), 7.73 (d, J=8.5 Hz, 1H), 7.50–7.35 (m, 2H), 5.11 (s, 1H), 1.20 (s, 9H).

Step 2: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 0.1 mm Hg) which was further purified by flash chromatography (silica gel, hexane) to give p-tolyltrimethyltin as a colorless liquid; $^1$H NMR (300 MHz, CDCl$_3$) δ7.40 (d, J=7.7 Hz, 2H), 7.19 (d, J=7.7 Hz, 2H), 2.34 (s, 3H), 0.30 (s, 9H).

Step 3: 4'-methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4'-methylbiphenyl-2-tert-butylsulfonamide as a white solid; $^1$H NMR (300 MHz, CDCl$_3$) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step 4: 4'-Bromomethylbiphenyl-2-tert-butylsulfonamide

N-Bromosuccinimide (0.387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4'-bromomethylbiphenyl-2-tert-butylsulfonamide (77% pure (the remainder of the material was 4'-dibromomethylbiphenyl-2-tert-butylsulfonamide)) as a white solid; $^1$H NMR (300 MHz, CDCl$_3$) δ8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLE 6A

4'-Bromomethylbiphenyl-2-(O-tert-butyl)-N-hydroxysulfonamide

Step 1: 2-Bromobenzene(O-tert-butyl)-N-hydroxysulfonamide

To a stirred solution of 2-bromobenzenesulfonyl chloride (Lancaster Synthesis) (1.0 g, 4.0 mmol) in chloroform (10 ml) under nitrogen at 0° C. was added O-tert-butylhydroxylamine hydrochloride (Fluka) (0.6 g, 4.77 mmol) in three portions. The solution was stirred at room temperature for 18 h and then diluted with methylene chloride (20 ml). The organic phase was washed successively with 5% citric acid, water and then dried over MgSO$_4$. Removal of the solvent in vacuo gave the crude product as white solid, which was then purified by flash chromatography (silica gel, 10% ethyl acetate-hexane) to afford 2-bromobenzene(O-tert-butyl)N-hydroxysulfonamide (1.12 g, 89%) as a white solid;

$^1$H NMR (300 MHz, CDCl$_3$) δ8.15 (dd, J=7.5, 2.1 Hz, 1H), 7.75 (d, J=7.6, 1.8 Hz, 1H), 7.55–7.35 (m, 3H), 5.11 (s, 1H), 1.21 (s, 9H). FAB-MS: 309 (M+H).

Step 2: 4′-Methylbiphenyl-2-(O-tert-butyl)-N-hydroxysulfonamide

A solution of 2-bromobenzene(O-tert-butyl)-N-hydroxysulfonamide (0.31 g, 1.0 mmol), p-tolyltrimethyltin (0.3 g, 1.18 mmol) and bis(triphenylphosphine)palladium(II) chloride (Aldrich) (0.036 g) in dry dimethylformamide (6 ml) was stirred under nitrogen at 90° C. for 6 h. The black suspension was cooled to room temperature, then filtered through a pad of celite which was washed with tetrahydrofuran. The colorless filtrate was evaporated to dryness then purified by flash chromatography (silica gel, 8% ethyl acetate-hexane) to give the titled compound as a semi-solid mass. $^1$H NMR (300 MHz, CDCl$_3$) δ8.15 (d, J=7.8, 1.6 Hz, 1H), 7.67–7.50 (m, 2H), 7.36–7.24 (m, 5H), 5.78 (s, 1H), 2.42 (s, 3H), 1.08 (s, 9H). FAB-MS: 320 (M+H).

Step 3: 4′-Bromomethylbiphenyl-2-(O-tert-butyl)-N-hydroxysulfonamide

A mixture of N-Bromosuccinimide (0.14 g, 0.78 mmol), a,a′-azoisobutyronitrile (10 mg) and 4′-methylbiphenyl-2-(O-tert-butyl)-N-hydroxy sulfonamide (0.25 g, 0.78 mmol) in carbon tetrachloride (10 ml) was refluxed for 7 h. After cooling to room temperature the mixture was filtered and the filtrate evaporated to dryness. Flash chromatography (silica gel, 10% ethyl acetate-hexane) afforded 4′-methylbiphenyl-2-(O-tert-butyl)-N-hydroxy sulfonamide as a white solid.

$^1$H NMR (300 MHz, CDCl$_3$) δ8.15 (d, J=7.8 Hz, 1H), 7.70–7.30 (m, 7H), 5.72 (s,1H), 4.55 (s, 2H), 1.08 (s, 9H). FAB-MS: 398, 400 (M+H).

PREPARATION OF 2-ALKYL-QUINAZOLIN-4(1H)-ONES

EXAMPLE 7

2-Butyl-6-methylquinazolin-4(1H)-one

To a solution of 3.0 g (20 mmol) of 2-amino-5-methylbenzoic acid in 20 mL of dry DMF at 0° C. was added 200 mg of DMAP followed by 6.07 g (60 mmol) of triethyl amine and 5.02 g (40 mmol) of valeryl chloride. The resulting mixture was stirred at 0° C. for 30 minutes. The mixture was heated to 110° C. and monitored by TLC for the formation of the intermediate quinoxazolone (rf=0.8, 40% EtOAc/hexane). Following complete formation of the intermediate 10 g (100 mmol) of NH$_4$CO$_3$ was added cautiously. Heating was continued to ensure consumption of the quinoxazolone and formation of the polar (rf=0.4, 40% EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystallized from MeOH to give 1.07 g (5 mmol) of a white crystaline solid. 25% yield overall. $^1$H-NMR (CDCl$_3$): 0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H). Anal (C$_{13}$H$_{16}$N$_2$O), C, H, N.

EXAMPLE 8

6-Methyl-2-propylquinazoline-4(1H)-one

The 2-propyl derivative was prepared in the identical fashion as the 2-butyl derivative through the use of butyryl chloride in place of valeryl chloride. The product was recrystallized from hexane/acetone to give white crystals. 32% yield. $^1$H-NMR (CDCl$_3$): 11.51 (bs, 1H), 8.08 (s, 1H), 7.60 (s, 2H), 2.78 (3 line m, 2H), 2.01 (s, 3H), 1.92 (m, 2H), 1.09 (t, 3H).

EXAMPLE 9

2-Butyl-7-methylquinazoline-4(1H)-one

Same procedure as in Example 7 with valeroyl chloride and 2-amino-4-methylbenzoic acid. The product was recrystallized from MeOH recovering 0.91 g (4.2 mmol). 21% yield overall. $^1$H-NMR (CDCl$_3$): 0.99 (t, 3H, J=7.4 Hz), 1.49 (m, 2H), 1.86 (m, 2H), 2.50 (s, 3H), 2.76 (t, 2H, J=7.81 Hz), 7.28 (d, 1H, J=8.3 Hz), 7.49 (s, 1H), 8.15 (d, 1H, J=8.3 Hz). Anal (C$_{13}$H$_{16}$N$_2$O), C, H, N.

EXAMPLE 10

2-Butyl-naphtho[2,3-e]quinazoline-4(1H)-one

Same procedure as in Example 7 with valeroyl chloride and 2-aminonapthoic acid. Product was recrystallized from MeOH. A contaminant co-crystallizes with the desired product. The contaminant is 25% of the product by $^1$H-NMR. Recovered 1.6 g (59% yield).

$^1$H-NMR (CDCl$_3$): 0.97 (t, 3H, J=7.3 Hz), 1.42 (m, 2H), 1.75 (m, 2H), 2.48 (t, 2H, J=7.4 Hz), 7.42 (t, 1H, J=7.8 Hz), 7.54 (t, 1H, J=8.3 Hz), 7.77 (d, 1H, J=7.8 Hz), 7.82 (d, 1H, J=8.31 Hz),8.07 (s, 1H), 9.08 (s, 1H), 10.89 (bs, 1H).

EXAMPLE 11

2-Butyl-5-methylquinazoline-4(1H)-one

Same procedure as in Example 7 with valeroyl chloride and 2-amino-6-methylbenzoic acid on a 16 mmol scale. The concentrated reaction mixture was diluted with 50 mL ether and 50 mL H$_2$O. The mixture was agitated for several minutes and then filtered in vacuo. On filtration further crystalline material formed in the filtrate. The filtrate was filtered again. This procedure was repeated a further two times. The precipitates were collected and combined. The ethereal phase was decanted from the aqueous phase, and concentrated to 15 mL. 25 mL of hexanes was then added and the mixture filtered. The combined precipitates were recrystallized from MeOH/H$_2$O to give 0.73 g (3.37 mmol) of fluffy white crystals. 21% yield. $^1$H-NMR (CDCl$_3$): 0.98 (t, 3H, J=7.38 Hz), 1.48 (m, 2H), 1.87 (m, 2H), 2.75 (dd, 2H, J=8.09 Hz), 2.89 (s, 3H), 7.20 (d, 1H, J=6.73 Hz), 7.56 (m, 2H), 11.68 (bs, 1H).

EXAMPLE 12

2-Butyl-6,8-dimethylquinazoline-4(1H)-one

Same procedure as in Example 7 with valeroyl chloride and 2-amino-5,8-dimethylbenzoic acid on a 12 mmol scale. The product collected from filtration of the ether/water mixture was recrystalized from MeOH. $^1$H-NMR and TLC indicated that the product isolated was a 50% mixture of the desired quinazoline and a contaminant. An aliquot of 0.5 g of this material was concentrated onto 5 mL of flash silica and applied to the surface of a flash chromatography column. The column was eluted with 60% EtOAc/hexanes. The first eluted compound (0.14 g) was collected as a TLC homogeneous sample of the desired product. $^1$H-NMR (CDCl$_3$): 0.99 (t, 3H, J=7.32 Hz), 1.48 (m, 2H), 1.85 (m, 2H), 2.44 (s, 3H), 2.58 (s, 3H), 2.75 (dd, 2H, J=7.87,7.87 Hz), 7.43 (s, 1H), 7.91 (s, 1H), 10.70 (bs, 1H).

EXAMPLE 13

2-Butyl-8-methylquinazoline-4(1H)-one

Same procedure as in Example 7 with valeroyl chloride and 2-amino-6-methylbenzoic acid on a 1 mmol scale. The concentrated reaction mixture was diluted with 20 mL ether/20 mL H$_2$O. The mixture was filtered. The ethereal phase was seperated, dried (MgSO$_4$), filtered and concentrated. The residue was flash chromatographed over silica eluting with 50% EtOAc/hexanes to give rise to 48 mg (0.22 mmol) of a fluffy yellow solid. 22% yield. $^1$H-NMR (CDCl$_3$): 1.02 (t, 3H), 1.52 (m, 2H), 1.88 (m, 2H), 2.62 (s, 3H), 2.79 (dd, 2H), 7.35 (dd, 1H), 7.61 (d, 1H), 8.12 (d, 1H). FABMS: 217 (M$^+$+1) calc for C$_{13}$H$_{16}$N$_2$O.

EXAMPLE 14

2-Butyl-6-isopropylquinazolin-4(1H)-one

Same procedure as in Example 7 with valeroyl chloride and 2-amino-5-isopropylbenzoic acid on a 16 mmol scale. The concentrated reaction mixture was partitioned between 20 mL water and 20 mL of ether. A fine white precipitate was removed by filtration and recrystallized from MeOH/water. The first crop gave rise to 0.56 g of fluffy white crystals. $^1$H-NMR (CDCl$_3$): 0.99 (t, 3H, J=7.3 Hz), 1.32 (d, 6H, J=6.89 Hz), 1.48 (m, 2H), 1.85 (m, 2H), 2.77 (3 line m, 2H, J=7.9 Hz), 3.06 (m, 1H), 7.65 (m, 2H), 8.11 (s, 1H), 11.22 (bs, 1H). FABMS: 245 (M$^+$+1) calc for C$_{15}$H$_{20}$N$_2$O.

EXAMPLE 15

2-Butyl-6-thiomethylquinazolin-4(1H)-one

Same procedure as that described in Example 7. However on addition of ether/water to the reaction mixture a precipitate of the quinazolinone was not formed. The aqueous phase was extracted with ether and the combined ethereal extracts were washed with brine and dried over MgSO$_4$. The mixture was filtered and concentrated in vacuo to give a mixture of the desired product and 2-(N-valeroyl-amino)-5-thiomethylbenzamide. This mixture was heated with 2 equivalents of 1N NaOH solution in water at 100° C. until a clear solution was obtained. The solution was cooled, acidified, and filtered to give a pale yellow precipitate. The product was recrystalized from MeOH to give the title compound. $^1$H-NMR (CDCl$_3$-300 MHz): 1.00 (t, 3H, J=7.3 Hz), 1.50 (m, 2H), 1.86 (m, 2H), 2.58 (s, 3H), 2.76 (3 line m, 2H, J=7.9 Hz), 7.62 (m, 2H), 8.03 (d, 1H, J=1.9 Hz), 11.11 (bs, 1H).

EXAMPLE 16

6-Nitro-2-propylquinazolin-4(1H)-one

To a solution of 16.3 g (0.1 mol) of 2-amino-5-nitrobenzonitrile in 200 ml of CH$_2$Cl$_2$ at 0° C. was added 21 ml (0.15 mol) of triethyl amine followed by 0.3 g of DMAP and 11.71 g (0.11 mol) of butyryl chloride. The reaction mixture was warmed to room temperature and then heated over night at 50° C. The solution was washed with 1N HCl (1×20 ml), water (1×20 ml), saturated NaHCO$_3$ (2×20 ml) and brine (1×20 ml) and dried over MgSO$_4$. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% H$_2$O$_2$ and 50 ml of water. The mixture was refluxed for 4 hours, cooled and filtered. The filtrate was acidified with 1N HCl and the resulting precipitate recovered by filtration. The residue was recrystalized from MeOH to provide the title compound.

$^1$H-NMR (CDCl$_3$): 1.10 (t, 3H, J=7.4 Hz), 1.93 (m, 2H), 2.79 (3 line m, 2H, J=7.3 Hz), 7.80 (d, 1H, J=8.9 Hz), 8.55 (dd, 1H, J=2.5, 8.8 Hz), 9.14 (bs, 1H).

EXAMPLE 17

2-Butylquinazolin-4(1H)-one

To a solution of 500 mg 2-aminobenzonitrile (4.23 mmol), 514 mg triethylamine (5.08 mmol), and 50 mg DMAP (0.41 mmol) in 6 mL CH$_2$Cl$_2$ at 0° C. was added 562 mg valeryl chloride (4.66 mmol) dropwise over 1 minute. The mixture was warmed to room temperature and stirred for twenty minutes. The mixture was then diluted with water and brine and then was extracted three times with ether. The combined organic material was dried over MgSO$_4$, stripped of solvent in vacuo, and was purified by flash chromatography eluting with 20% ethyl acetate in hexane to give 2-valerylamidobenzonitrile. R$_f$ 0.22 in 20% ethyl acetate in hexane. $^1$H-NMR (300 MHz, CDCl$_3$): 8.42 (d, 1H), 7.60–7.10 (m, 2H), 6.72 (m, 1H), 4.40 (br s, 1H), 2.46 (t, 2H), 1.74 (m, 2H), 1.43 (m, 2H), 0.97 (t, 3H).

To a solution of 5.1 g of the amide in 90 mL methanol were added 21 mL 3N NaOH and 10 ml 30% H$_2$O$_2$ at room temperature. The mixture was refluxed for 30 minutes and concentrated in vacuo. Water and sat. NH$_4$Cl was added and the mixture extracted 3 times with ether. The combined organic extracts were dried over MgSO$_4$, filtered and concentrated in vacuo and the residue was recrystallized from hexane/acetone to give two crops of the product as white needles. 2.2 g, 43% yield. R$_f$ 0.16 in 20% EtOAc in CH$_2$Cl$_2$. $^1$H-NMR (CDCl$_3$): 8.29 (m, 1H), 7.81–7.68 (m, 2H), 7.47 (m, 1H), 2.79 (3 line m, 2H), 1.87 (m, 2H), 1.51 (m, 2H), 1.00 (t, 1H).

EXAMPLE 18

6-Bromomethyl-2-butylquinazolin-4(1H)-one

To a suspension of 2.6 g (12 mmol) of the product of Example 8 in 100 mL of dry CCl$_4$ was added 2.56 g of N-bromosuccinimide followed by 200 mg of benzoyl peroxide. The reaction mixture was heated to reflux for 45 minutes at which time a precipitate formed throughout. The reaction mixture was concentrated in vacuo and the residue partitioned between 150 mL of EtOAc and 100 mL of water. The mixture was shaken and then filtered to give the title compound. The filtrate was separated into two phases and the organic phases was washed with 75 mL of sat. NaHCO$_3$ solution followed by 75 mL of water and 75 mL of brine. The organic phase was dried over MgSO$_4$, filtered and the filtrate was concentrated in vacuo. The residue was purified by recrystalization from EtOAc to give more of the same product as was recovered above. $^1$H-NMR (CDCl$_3$):

1.00 (t, 3H, J=7.33 Hz), 1.49 (m, 2H), 1.84 (m, 2H), 2.77 (3 line m, 2H, J=7.7 Hz), 4.61 (s, 2H), 7.68 (d, 1H, J=8.4 Hz), 7.80 (dd, 1H, J=8.4, 2.1 Hz), 8.27 (d, 1H, J=2.1 Hz), 11.02 (bs, 1H).

EXAMPLE 19

5-Bromomethyl-2-butylquinazolin-4(1H)-one

The product of Example 11 was treated as in Example 19 to give the titled compound as a white solid. $^1$H-NMR (CDCl$_3$): 1.0 (t, 3H, J=7.3 Hz), 1.53 (m, 2H), 2.90 (m, 2H), 2.81 (3 line m, 2H, J=7.98 Hz), 5.31 (s, 2H), 7.45 (m, 1H), 7.71 (m, 2H), 11.28 (bs, 1H).

EXAMPLE 20

6-Acetoxymethyl-2-butylquinazolin-4(1H)-one

To a solution of 2.1 g (7.0 mmol) of the quinazolinone prepared in Example 18 in 15 mL of dry DMF was added 1.74 g (20.0 mmol) of sodium acetate. The mixture was heated to 60° C. for 3 hours. The reaction mixture was concentrated in vacuo and the residue dissolved in 100 mL of CH$_2$Cl$_2$. The solution was washed with water (3×20 mL), brine (1×20 mL) and dried over MgSO$_4$. The mixture was filtered and concentrated in vacuo. The residue was recrystallized from MeOH/H$_2$O to give the titled compound as a colorless solid. 68% yield. $^1$H-NMR (CDCl$_3$): 0.99 (t, 3H, J=7.32 Hz), 1.50 (m, 2H), 1.83 (m, 2H), 2.14 (t, 3H), 2.77 (3 line m, 2H, J=7.71 Hz), 5.23 (s, 2H), 7.69-7/78 (m, 2H), 8.25 (s, 1H), 10.90 (bs, 2H).

EXAMPLE 21

5-Acetoxymethyl-2-butylquinazolin-4(1H)-one

The product of Example 19 was treated as in Example 20 to give after recrystallization from EtOAc the desired acetylated product. $^1$H-NMR (CDCl$_3$): 0.98 (t, 3H, J=7.38 Hz), 1.50 (m, 2H), 1.88 (m, 2H), 2.19 (s, 3H), 2.77 (3 line m, 2H, J=7.93 Hz), 5.85 (s, 2H), 7.48 (m, 1H), 7.70 (m, 2H), 11.65 (bs, 1H).

EXAMPLE 22

2-Butyl-6-nitroquinazolin-4(1H)-one

The title compound was prepared as described above in Example 16 utilizing pentanoyl chloride in place of butyroyl chloride.

$^1$H-NMR (CDCl$_3$): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

PREPARATION OF 3-N-ALKYL-2-ALKYLQUINAZOLIN-4(3H)-ONES

A general procedure for the synthesis of 3-N-akylated-quinazolin-4(3H)-ones is given below. Chromatography conditions, yields, and spectral data are given for the compounds prepared by this procedure.

A suspension of 1.1 mmol of NaH in 2 mL of dry DMF at 0° C. under nitrogen was treated with 1 mmol of the quinazolin-4(1H)-one as a solid (most quinazolin-4(1H)-ones prepared were insoluble in DMF). Immediate evolution of hydrogen could be observed as the quinazolin-4(1H)-one was deprotonated and dissolved. After 30 minutes the solution was warmed to room temperature for a further 30 minutes. To this solution cooled to 0° C. was added a solution of 1 mmol of the appropriate 4-bromomethyl-2'-substituted-biphenyl compound in DMF. After 30 minutes, the reaction mixture was warmed to room temperature and stirred overnight. The solution was concentrated in vacuo, and the residue dissolved in 50 mL of EtOAc. The solution was washed with water (3×10 mL) and brine (2×10 mL). The organic phase was dried over MgSO$_4$, filtered and concentrated in vacuo. The residue was purified as indicated below:

EXAMPLE 23

2-Butyl-3-[(2'-(t-butoxycarbonyl)biphen-4-yl)methyl]-quinazolin-4(3H)-one

The quinazolinone prepared as described in Example 17 was alkylated with 4-bromomethyl-2'-t-butoxycarbonyl-biphenyl. The product was purified by flash chromatography over silica gel eluting with 1% EtOAc/methylene chloride. $^1$H-NMR (300 MHz, CDCl$_3$): 8.32 (m, 1H), 7.76 (m, 2H), 7.46 (m, 2H), 7.38 (m, 1H), 7.32-7.18 (m, 5H), 5.46 (bs, 2H), 2.79 (3 line m, 2H), 1.80 (m, 2H), 1.44 (m, 2H), 1.23 (s, 9H), 0.95 (t, 3H).

EXAMPLE 24

2-Butyl-3-[(2'-(cyano)biphen-4-yl)methyl]quinazolin-4(3H)-one

The quinazolinone prepared as described in Example 17 was alkylated with 4-bromomethyl-2'-cyanobiphenyl. The product was purified by MPLC Lobar C silica column eluting with 25% EtOAc/hexane. R$_f$ 0.13 in 30% EtOAc/hexane. $^1$H-NMR (300 MHz, CDCl$_3$): 8.32 (m, 1H), 7.84-7.59 (m, 7H), 5.46 (bs, 2H), 2.79 (3 line m, 2H), 1.80 (m, 2H), 1.44 (m, 2H), 0.94 (t, 3H).

EXAMPLE 25

2-Butyl-3-[(2'-(t-butoxycarbonyl)biphen-4-yl)methyl]-8-methylquinazolin-4(3H)-one The quinazolinone prepared as described in Example 13 was alkylated with 4-bromomethyl-2'-t-butoxycarbonyl-biphenyl. The product was purified by flash chromatography over silica eluting 12.5% EtOAc/hexane. 58% yield. $^1$H-NMR (CDCl$_3$): 0.95 (t, 3H, J=7.3 Hz), 1.23 (s, 9H), 1.44 (m, 2H), 1.85 (m, 2H), 2.62 (s, 3H), 2.79 (dd, 2H, J=7.65, 7.65 Hz), 5.45 (bs, 2H), 7.20-7.50 (m, 8H), 7.59 (dd, 1H, J=1.1, 8.47 Hz), 7.77 (dd, 1H, J=1.6, 7.7 Hz), 8.16 (dd, 1H, J=1.2, 7.7 Hz). FABMS, 483 (M$^+$+1).

EXAMPLE 26

2-Butyl-3-[(2'-(t-butoxycarbonyl)biphen-4-yl)methyl]-6-methylquinazolin-4(3H)-one The quinazolinone prepared as described in Example 7 was alkylated with 4-bromomethyl-2'-t-butoxycarbonyl-biphenyl. The product was purified by flash chromatography over silica gel eluting with 15% EtOAc/hexane, 43% yield. $^1$H-NMR (CDCl$_3$): 0.95 (t, 3H, J=7.3 Hz), 1.23 (s, 9H), 1.43 (m, 2H), 1.79 (m, 2H), 2.49 (s, 3H), 2.77 (dd, 2H, J=8.0, 8.0 Hz), 5.46 (bs, 1H), 7.19-7.60 (m, 10H), 7.77 (dd, 1H, J=1.6, 7.6 Hz). FABMS, 483 (M$^+$+1).

EXAMPLE 27

2-Butyl-3-[(2'-(t-butoxycarbonyl)biphen-4-yl)methyl]-6-nitroquinazolin-4(3H)-one The quinazolinone prepared as described in Example 16 was alkylated with 4-bromomethyl-2'-t-butoxycarbonylbiphenyl. The product was purified by flash chromatography over silica gel eluting with 20% EtOAc/- hexane. $^1$H-NMR (CDCl$_3$): 0.96 (t, 3H, J=7.38 Hz), 1.25 (s, 9H), 1.45 (m, 2H), 1.83 (m, 2H), 2.84 (dd, 2H, J=8.08 Hz), 5.47 (bs, 2H), 7.20–7.50 (m, 8H), 7.78 (d, 1H, J=9.07 Hz), 8.53 (dd, 1H, J=2.5, 8.8 Hz), 9.18 (d, 1H, J=2.5 Hz). FABMS, m/z 514 (M$^+$+1).

EXAMPLE 28

2-Butyl-3-[(2'-cyanobiphen-4-yl)-methyl]-6-methyl-quinazolin-4(3H)-one

The quinazolinone prepared as described in Example 7 was alkylated with 4-bromomethyl-2'-cyanobiphenyl. The product was purified by MPLC Lobar C silica gel column eluting with 20% EtOAc/hexane. $^1$H-NMR (CDCl$_3$): 0.95 (t, 3H, J=7.5 Hz), 1.42 (m, 2H), 1.77 (m, 2H), 2.48 (s, 3H), 2.77 (dd, 1H, J=8.0, 8.0 Hz), 5.46 (bs, 3H), 7.30 (d, 1H, J=7.9 Hz), 7.40–7.65 (m, 7H), 7.74 (d, 1H, J=7.9 Hz), 8.09 (s, 1H).

EXAMPLE 29

2-Butyl-3-[(2'-(t-butoxycarbonyl)biphen-4-yl)methyl]-7-methylquinazolin-4(3H)-one The quinazolinone prepared as described in Example 9 was alkylated with 4-bromomethyl-2-t-butoxycarbonylbiphenyl. The product was purified by flash chromatography over silica eluting with 20% EtOAc/hexane. $^1$H-NMR (CDCl$_3$): 0.95 (t, 3H, J=7.33 Hz), 1.23 (s, 9H), 1.42 (m, 2H), 1.79 (m, 2H), 2.50 (s, 3H), 2.77 (dd, 2H, J=7.9, 7.9 Hz), 5.44 (bs, 2H), 7.20–7.51 (m, 9H), 7.76 (dd, 1H, J=1.31, 7.71 Hz), 8.19 (d, 1H, J=8.13 Hz). Anal (C$_{31}$H$_{34}$N$_2$O$_3$), C, H, N.

EXAMPLE 30

2-Butyl-3-[(2'-(t-butoxycarbonyl)biphen-4-yl)methyl]-naphtho[2,3-e]quinazolin-4(3H)-one The quinazolinone prepared as described in Example 10 was alkylated with 4-bromomethyl-2'-t-butoxycarbonyl-biphenyl. The product was purified by MPLC Lobar B silica gel column eluting with 15% EtOAc/hexane. $^1$H-NMR (CDCl$_3$): 0.97 (t, 3H, J=7.27 Hz), 1.24 (s, 9H), 1.46 (m, 2H), 1.85 (m, 2H), 2.82 (dd, 2H, J=8.2, 8.2 Hz), 5.49 (bs, 1H), 7.2–7.61 (m, 9H), 7.76 (d, 1H, J=7.97 (d, 1H, J=8.6 Hz), 8.06 (d, 1H, J=7.9 Hz), 8.17 (s, 1H), 8.94 (s, 1H).

EXAMPLE 31

2-Butyl-3-[(2'-(t-butoxycarbonyl)biphen-4-yl)methyl]-6,8-dimethylquinazolin-4(3H)-one The quinazolinone prepared as described in Example 12 was alkylated with 4-bromomethyl-2'-t-butoxycarbonyl-biphenyl. The product was purified by MPLC Lobar B silica column eluting with 17% EtOAc/hexane. $^1$H-NMR (CDCl$_3$): 0.95 (t, 3H, J=7.2 Hz), 1.23 (s, 9H), 1.42 (m, 2H), 1.83 (m, 2H), 2.43 (s, 3H), 2.58 (s, 3H), 2.77 (dd, 2H, J=7.7 Hz), 5.44 (bs, 2H), 7.19–7.48 (m, 8H), 7.76 (d, 1H, J=6.2 Hz), 7.95 (s, 1H).

EXAMPLE 32

2-Propyl-3-[(2'-(cyano)biphen-4-yl)methyl]-6-methyl-quinazolin-4(3H)-one

The quinazolinone prepared as described in Example 8 was alkylated with 4-bromomethyl-2'-cyanobiphenyl. The product was purified by MPLC Lobar C silica column eluting with 30% EtOAc/hexane. $^1$H-NMR (CDCl$_3$): 8.10 (s, 1H), 7.79–7.25 (m, 10H), 5.49 (bs, 2H), 2.76 (3 line m, 2H), 2.49 (s, 3H), 1.84 (m, 2H), 1.02 (t, 3H, J=7.4 Hz).

EXAMPLE 33

2-Butyl-3-[2'-(t-butoxycarbonyl)biphen-4-yl)methyl]-5-methylquinazolin-4(3H)-one The quinazolinone prepared as described in Example 11 was alkylated with 4-bromomethyl-2'-t-butoxycarbonyl-biphenyl. The product was purified by MPLC Lobar B silica column eluting with 17% EtOAc/hexane. $^1$H-NMR (CDCl$_3$): 0.95 (t, 3H, J=7.3 Hz), 1.22 (s, 9H), 1.43 (m, 2H), 1.79 (m, 2H), 2.76 (dd, 2H, J=7.7, 7.7 Hz), 2.87 (s, 3H), 5.40 (bs, 2H), 7.18–7.59 (m, 10H), 7.77 (dd, 1H, J=1.4, 7.4 Hz).

EXAMPLE 34

2-Butyl-6-methyl-3-[(2'-nitrobiphen-4-yl)methyl]-quinazolinone

To a solution of 0.111 g (0.51 mmol) of 2-butyl-6-methylquinazolinone in 4.0 mL of dimethylformamide was added 0.022 g of a 60% oil dispersion of sodium hydride and the resulting mixture was stirred at room temperature under a nitrogen atmosphere. After 30 min hydrogen evolution had ceased, and 0.150 g (0.51 mmol) of 4-bromomethyl-2'-nitrobiphenyl was added to the reaction mixture. Stirring was continued for 2 h at room temperature and then the reaction mixture was partitioned between ethyl acetate and water. The organic layer was extracted, washed with water, brine, then dried (MgSO$_4$), filtered and evaporated. The residual oil was purified on a silica gel flash chromatography column eluted with 25% ethyl acetate-hexane to afford the product as a colorless oil which had: $^1$H-NMR (CDCl$_3$) δ0.91 (t, J=10 Hz, 3H), 1.34–1.47 (m, 2H), 1.69–1.80 (m, 2H), 2.46 (s, 3H), 2.74 (t, J=11 Hz, 2H), 5.43 (s, 2H), 7.18–7.28 (m, 4H), 7.36 (d, J=12 Hz, 1H), 7.45 (t, J=12 Hz, 1H), 7.52–7.62 (m, 3H), 7.83 (d, J=12 Hz, 1H), 8.08 (s, 1H); MS (FAB) m/e 428 (MH+).

EXAMPLE 35

3-[(2'-Aminobiphen-4-yl)methyl]-2-butyl-6-methyl-quinazolin-4(3H)-one

To a solution of 0.127 g (0.30 mmol) of 2-butyl-6-methyl-3-[(2'-nitrobiphen-4-yl)methyl]quinazolinone, from Example 34, in 15 mL of absolute ethanol was added 0.030 g of a 10% palladium on powdered charcoal catalyst and the resulting mixture was hydrogenated under a 35 psig hydrogen atmosphere in a Parr apparatus. After 1 h TLC analysis (50% ethyl acetate-hexane) of the reaction mixture indicated complete reduction. The mixture was filtered, evaporated and dried in vacuo to afford a viscous oil which was used directly in the next step without further purification: $^1$H-NMR (CDCl$_3$) δ0.91 (t, J=10 Hz, 3H), 1.36–1.47 (m, 2H), 1.70–1.82 (m, 2H), 2.47 (s, 3H), 2.77 (t, J=11 Hz, 2H), 3.72 (br s, 2H), 5.44 (s, 2H), 6.70–6.83 (m, 2H), 7.04–7.16 (m, 2H), 7.23 (d, J=14 Hz, 2H), 7.39 (d, J=14 Hz, 2H), 7.56 (s, 2H), 8.08 (s, 1H); MS (FAB) m/e 398 (MH+).

EXAMPLE 36

2-Butyl-3-[2'-(t-butoxycarbonyl)biphen-4-yl)methyl]-6-isopropylquinazolin-4(3H)-one To a suspension of sodium hydride (0.034 g of 50% oil suspension) in dry DMF (5 ml) was added 2-n-butyl-6-isopropylquinazolin-4-one (prepared as described in Example 14) (0.2 g, 0.76 mmol) and stirred at room temperature for 1.5 hours. At this stage, 4-bromomethyl-2'-t-butoxycarbonylbiphenyl (0.29 g, 0.77 mMol) was added, and the mixture was stirred at room temperature for 18 hours. The crude product isolated, after work-up as described in the general procedure for alkylation of quinazolin-4(3H)-ones was purified by flash chromatography over silica-gel using methylene chloride containing 1% methanol to give the desired compound as white amorphous solid. $^1$H-NMR(CDCl$_3$): 0.97 (t 3H, J=7.35 Hz), 1.19 (s, 9H), 1.31 (d, 6H, J=6.9 Hz), 1.45 (m, 2H), 1.81 (m, 2H, 2.95 (t, 2H, J=7.7 Hz), 3.07 (m, 1H), 5.69 (s, 2H), 7.33–7.94 (m, 11H). FAB-MS: m/e 455 (M+H), 909 (2M+H).

EXAMPLE 37

6-Amino-2-butyl-3-[(2'-(t-butoxycarbonyl)biphen-4-yl)-methyl]quinazolin-4(3H)-one 0.11 g (0.21 mmol) of 2-butyl-3-[(2'-(t-butoxycarbonyl)biphen-4-yl)methyl]-6-nitroquinazolin-3(1H)-one (Example 27) was suspended in 7.5 mL of MeOH and hydrogenated over 55 mg of 10% Pd/C under an atmospheric pressure hydrogen blanket. After 1 hour the reaction mixture was filtered through celite and the filtrate concentrated in vacuo. The residue was purified by flash chromatography over silica gel eluting with 50% EtOAc/hexane to give a white foam. $^1$H-NMR (CDCl$_3$): 0.94 (t, 3H, J=7. Hz), 1.23 (s, 9H), 1.41 (m, 2H), 1.79 (m, 2H), 2.74 (3 line m, 2H, J=7.7 Hz), 5.44 (bs, 2H), 7.05–7.57 (m, 10H), 7.77 (d, J=7.5 Hz).

EXAMPLE 38

Acetamido-2-butyl-3-[(2'-(t-butoxycarbonyl)biphenyl-4-yl)methyl]quinazolinon-4(3H)-one To 20 mg of the product of Example 37 in 0.75 mL of CH2Cl2 at room temperature was added 4.3 μL of acetic anhydride. After 6 hours a further 2 μL of acetic anhydride was added to the reaction mixture. The solution was allowed to stir for 7 days, diluted with 10 mL of EtOAc and washed with water (3×5 mL), brine (1×5 mL) and dried over MgSO$_4$. The solution was filtered and concentrated in vacuo to give the titled compound as a white solid. $^1$H-NMR (CD$_3$OD): 0.65 (t, 3H, J=7.3 Hz), 0.91 (s, 9H), 1.12 (m, 2H), 1.48 (m, 2H), 1.87 (s, 3H), 2.63 (3 line m, 2H, J=7.7 Hz), 5.21 (bs, 2H), 6.92–7.39 (m, 10H), 7.67 (dd, 1H, J=2.5, 8.8 Hz), 8.19 (d, 1H, J=2.5 Hz). FABMS m/z 526 (M+ +1) calc for C$_{32}$H$_{35}$N$_3$O$_4$.

SYNTHESIS OF 2-BUTYL-3-[(2'-(CARBOXY)BIPHEN-4-YL)-METHYL]-ALKYLOUINAZOLIN-4(3H)-ONES

General procedure for the preparation of the carboxylic acids from the t-butyl esters is as follows:

To 1 mmol of the ester in 1 mL of dry CH$_2$Cl$_2$ at room temperature was added 0.5 mL of trifluoroacetic acid. The solution was stirred under N$_2$ over night and concentrated in vacuo. The residue was reconcentrated in vacuo after dissolving the reaction product in a mixture of 0.5 mL of CH$_2$Cl$_2$ and 3 mL of toluene. The residue was allowed to dry in vacuo overnight. Any impurities were removed by flash chromatography.

EXAMPLE 39

6-Acetamido-2-butyl-3-[(2'-(carboxy)biphen-4-yl)methyl]-quinazolin-4(3H)-one

The product of Example 38 was deprotected following the general procedure described above. Purification by flash chromatography eluting with 5:95:1 MeOH:CH$_2$Cl$_2$:HOAc to give a white solid, $^1$H-NMR (CD$_3$OD): 0.61 (t, 3H, J=7.43 Hz), 1.12 (m, 2H), 1.42 (m, 2H), 1.86 (s, 3H), 2.52 (3 line m, 2H, J=7.4 Hz), 5.18 (bs, 2H), 6.85–7.22 (m, 8H), 7.19 (d, 1H, J=7.3 Hz), 7.46 (d, 1H, J=7.3 Hz), 7.69 (dd, 1H, J=2.2,8.8 Hz), 8.12 (d, 1H, J=2.22 Hz). FABMS m/z 470 (M+ +1) calc for C$_{28}$H$_{27}$N$_3$O$_4$.

EXAMPLE 40

6-Amino-2-butyl-3-[(2'-(carboxy)biphen-4-yl)methyl]-quinazolin-4(3H)-one

The product of Example 37 was deprotected following the general procedure described above. Purification by flash chromatography over silica gel eluting with 60:40:1 EtOAc:hexane:acetic acid. The product is very insoluble when concentrated to give a white solid. $^1$H-NMR (CDCl$_3$): 0.87 (t, 3H, J=7.37 Hz), 1.35 (m, 2H), 1.69 (m, 2H), 2.71 (3 line m, 2H, J=6.9 Hz), 3.2–4.5 (bs, 4H), 5.41 (bs, 2H), 7.05–7.59 (m, 10H), 7.54 (bs, 1H).

EXAMPLE 41

2-Butyl-3-[(2'-(carboxy)biphen-4-yl)methyl]quinazolin-4(3H)-one

The product of Example 23 was deprotected following the general procedure described above. The crude material was purified by flash chromatography eluting with 1:1:38:60 acetic acid/MeOH/hexane/methylene chloride. $^1$H-NMR (CDCl$_3$): 9.60–8.50 (bs, 1H), 8.30 (m, 1H), 7.94 (m, 1H), 7.71 (m, 2H), 7.58 –7.37 (m, 3H), 7.32 (m, 3H), 7.19 (m, 2H), 5.45 (bs, 2H), 2.75 (3 line m, 2H), 1.67 (m, 2H), 1.34 (m, 2H), 0.84 (t, 3H). FABMS m/z 413 (M+ +1).

EXAMPLE 42

2-Butyl-3-[(2'-(carboxy)biphen-4-yl)methyl]-5-methyl-quinazolin-4(3H)-one

The product of Example 33 was deprotected following the general procedure described above. The crude concentrated reaction mixture was homogeneous by TLC and NMR. $^1$H-NMR (CDCl$_3$): 0.88 (t, 3H, J=7.21), 1.43 (m, 2H), 1.69 (m, 2H), 2.87 (s, 3H), 3.13 (dd, 2H, J=8.0, 8.0 Hz), 5.46 (bs, 2H), 7.21–7.36 (m, 5H), 7.43 (d, 2H, J=8.74 Hz), 7.58 (t, 1H, J=7.4 Hz), 7.69–7.81 (m, 2H), 7.96 (d, 1H, J=7.8 Hz).

EXAMPLE 43

2-Butyl-3-[(2'-(carboxy)biphen-4-yl)methyl]-naphtho[2,3-e]quinazolin-4(3H)-one

The product of Example 30 was deprotected following the general procedure described above. The crude concentrated reaction mixture was homogeneous by TLC and NMR. $^1$H-NMR (CDCl$_3$): 0.91 (t, 3H, J=7.22 Hz), 1.49 (m, 2H), 1.75 (m, 2H), 3.20 (bdd, 2H, J=7.6, 7.6 Hz), 5.52 (bs, 2H), 7.20–7.35 (m, 5H), 7.42 (t, 1H, J=7.7 Hz), 7.55 (t, 1H, J=7.3 Hz), 7.68 (t, 1H, J=7.3 Hz), 7.77 (t, 1H, J=8.0 Hz), 7.94 (d, 1H, J=7.7 Hz), 8.07 (d,2H, J=8.2 Hz), 8.93 (s, 1H), 11.99 (bs, 1H). FABMS: m/z 463 (M+ +1).

EXAMPLE 44

2-Butyl-3-[(2'-(carboxy)biphen-4-yl)methyl]-7-methyl-quinazolin-4(3H)-one

The product of Example 29 was deprotected following the general procedure described above. The product was purified by flash chromatography over silica eluting with 40% EtOAc/hexane/1% acetic acid. ¹H-NMR (CDCl₃): 0.91 (t, 3H, J=7.3 Hz), 1.42 (m, 2H), 1.71 (m, 2H), 2.54 (s, 3H), 3.01 (dd, 2H, J=7.8, 7.8 Hz), 5.44 (bs, 2H), 7.10–7.45 (m, 8H), 7.54 (t, 1H, J=7.5 Hz), 7.69 (s, 1H), 7.93 (d, 1H, J=7.7 Hz), 8.19 (d, 1H, J=8.1 Hz). FABMS: 427 (M⁺+1).

EXAMPLE 45

2-Butyl-3-[(2'-(carboxy)biphen-4-yl)methyl]-8-methyl-quinazolin-4(3H)-one

The product of Example 25 was deprotected following the general procedure described above. The product was purified by flash chromatography over silica gel eluting with 25% EtOAc/75% hexane/1% acetic acid. ¹H-NMR (CDCl₃): 0.91 (t, 3H, J=7.3 Hz), 1.41 (m, 2H), 1.82 (m, 2H), 2.61 (s, 3H), 2.78 (dd, 2H, J=7.3, 7.3 Hz), 5.44 (bs, 2H), 7.15–7.61 (m, 9H), 7.92 (d, 1H, J=7.3 Hz), 8.15 (d, 1H, J=7.8 Hz). FABMS: 427 (M⁺+1).

EXAMPLE 46

2-Butyl-3-[(2'-(carboxy)biphen-4-yl)methyl]-6-methyl-quinazolin-4(3H)-one

The product of Example 26 was deprotected following the general procedure described above. The product was purified by flash chromatography over silica gel eluting with 30% EtOAc/70% hexane/1% acetic acid. ¹H-NMR (CDCl₃): 0.89 (3H, t), 1.38 (m, 2H), 1.69 (m, 2H), 2.48 (s, 3H), 2.83 (dd, 2H), 5.41 (bs, 2H), 7.16 (d, 2H), 7.22–7.31 (m, 3H), 7.41 (t, 1H), 7.52 (t, 1H), 7.59 (m, 1H), 7.68 (d, 1H), 7.91 (d, 1H), 8.08 (s, 1H). FABMS: 427 (M⁺+1).

EXAMPLE 47

2-Butyl-3-[(2'(carboxy)biphen-4-yl)methyl]-6-nitroquinazolin-4(3H)-one

The product of Example 27 was deprotected following the general procedure described above. The product was purified by flash chromatography over silica gel eluting with 70:30:1 EtOAc:hexane:acetic acid, 80% yield. ¹H-NMR (CDCl₃): 0.91 (t, 3H, J=7.33 Hz), 1.41 (m, 2H), 1.79 (m, 2H), 2.84 (3 line m, 2H, J=7.98 Hz), 5.45 (bs, 2H), 7.18–7.32 (m, 5H), 7.42 (dd, 1H, J=7.7, 7.7 Hz), 7.55 (dd, 1H, J=6.4,6.4 Hz), 7.77 (d, 1H, J=9.0 Hz), 7.92 (d, 1H, J=7.4 Hz), 8.51 (dd, 1H, J=2.6, 9.3 Hz), 9.15 (d, 1H, J=2.6 Hz). FABMS m/z 458 (M⁺+1) calc. for $C_{26}H_{23}N_3O_5$.

EXAMPLE 48

2-Butyl-3-[(2'-(carboxy)biphen-4-yl)methyl]6,8-dimethylquinazolin-4(3H)-one

The product of Example 31 was deprotected following the general procedure described above. Purification by flash chromatography over silica gel eluting with 30% EtOAc/hexanes/1% acetic acid. ¹H-NMR (CDCl₃): 0.90 (t, 3H, J=7.3 Hz), 1.40 (m, 2H), 1.80 (m, 2H), 2.43 (s, 3H), 2.57 (s, 3H), 2.77 (3 line m, 2H, J=7.7 Hz), 5.44 (bs, 2H), 7.17–7.42 (m, 7H), 7.53 (dt, 1H, 7.5, 1.4 Hz), 7.90–7.95 (m, 2H). FABMS: 441 (M⁺+1) calc. for $C_{28}H_{28}N_2O_3$.

ALTERNATIVE METHOD OF PREPARING CARBOXYLIC ACIDS FROM t-BUTYL ESTERS

EXAMPLE 49

6-Isopropyl-2-propyl-3-[(2'-carboxybiphen-4-yl)-methyl]-quinazolin-4(3H)-one

A solution of 6-isopropyl-2-n-propyl-3-[(2'-(t-butoxycarbonyl)biphen-4-yl)-methyl]-quinazolin-4(3H)-one (0.198 g, 0.44 mmol) in a mixture of methylene chloride (3 ml) and anhydrous trifluoro acetic acid (3 ml) containing anisole (0.05 ml) was stirred at room temperature for 4 hours. The solvent was then removed under reduced pressure and the residue was triturated with dry ether to give the solid product, which was then collected by filteration and dried in vacuo over NaOH and P₂O₅ to give the desired product as the mono trifluoroacetate salt. ¹H-NMR(CDCl₃): 0.91 (t, 3H, J=7.35 Hz), 1.32 (d, 6H, J=6.9 Hz), 1.47 (m, 2H), 1.72 (m, 2H), 3.12 (m, 3H), 5.48 (s, 2H), 7.14–7.96 (m, 11H), 8.16 (d, 1H, J=1.9 Hz). FAB-MS m/e 399 (M+H).

EXAMPLE 50

6-Isopropyl-2-propyl-3-[(2'-(N-dibenzylphosphoryl)-carboxamidobiphen-4-yl)-methyl]-quinazolin-4(3H)-one The carboxylic acid (1 mMol), obtained from Example 49 is dissolved in dry THF (10 ml), and to the solution is added 1,1'carbonyl-diimidazole (2.2 mMol). The mixture is refluxed for 3–4 hours and then cooled down to room temperature. A stream of ammonia is then introduced into the reaction, and the desired amide is isolated after evaporation of the solvent and recrystallization of the crude product. The amide, thus obtained, is dissolved in dry THF (10 mL) and treated with BuLi (1.1 equiv.) at −78° C. To the resulting lithium salt is then added dibenzylphosphoryl chloride at −78° C. The mixture is then warmed to room temperature and stirred overnight. The solvent is removed in vacuo, and the residue is then partitioned between EtOAc and water. The organic phase is dried over MgSO₄ and concentrated to give the crude product, which is then purified by flash chromatography using silica gel.

PREPARATION OF 1,2 DISUBSTITUTED QUINAZOLIN-4(1H)-ONES

EXAMPLE 51

N-Valeroyl-2-aminobenzonitrile

To a solution of 500 mg 2-aminobenzonitrile (4.23 mmol), 514 mg triethylamine (5.08 mmol), and 50 mg DMAP (0.41 mmol) in 6 mL CH₂Cl₂ at 0° C. was added 562 mg valeroyl chloride (4.66 mmol) dropwise over 1 minute. The mixture was warmed to room temperature and stirred for 20 minutes. The mixture was then diluted with water and brine and was extracted three times with ether. The combined organic material was dried over MgSO₄, stripped of solvent in vacuo, and was purified by flash chromatography over silica eluting with 20% ethyl acetate in hexane to give the title compound. $R_f$ 0.22 in 20% ethyl acetate in hexane. ¹H-NMR (300 MHz, CDCl₃): 8.42 (d, 1H), 7.60–7.10 (m, 2H), 6.72 (m, 1H), 4.40 (br s, 1H), 2.46 (t, 2H), 1.74 (m, 2H), 1.43 (m, 2H), 0.97 (t, 3H)

EXAMPLE 52

N-Valeroyl-N-[(2'-(t-butoxycarbonyl)biphen-4-yl)methyl]-2-aminobenzonitrile

To a solution of 146 mg of the product from Example 51 (0.72 mmol), 250 mg (0.72 mmol) 4-bromomethyl-2'-t-butoxycarbonylbiphenyl, and 119 mg NaI (0.79 mmol) in 4 mL DMF was added 46 mg 60% NaH dispersion in oil (1.15 mmol) at room temperature. After 45 minutes the mixture was diluted with water and brine and then was extracted three times with ether. The combined organic material was dried over MgSO$_4$, stripped off solvent in vacuo, and was purified by MPLC over silica eluting with 20% ethyl acetate in hexane. R$_f$ 0.20 in 20% ethyl acetate in hexane. $^1$H-NMR (300 MHz, CDCl$_3$): 7.75 (d, J=7.7 Hz, 2H), 7.58–7.20 (m, 9H), 6.99 (d, J=7.7 Hz, 1H), 5.60 (d, J=14.5 Hz, 1H), 4.42 (d, J=14.3 Hz, 1H), 2.05 (m, 2H), 1.62 (m, 2H), 1.26 (s, 9H), 1.25 (m, 2H), 0.85 (t, 3H)

EXAMPLE 53

2-Butyl-1-[(2'-(carboxy)biphen-4-yl)methyl]quinazolin-4(1H)-one

To a solution of the purified N-valeroyl-N-[(2'-(t-butoxycarbonyl)biphen-4-yl)methyl]-2-aminobenzonitrile (from Example 52) in 4 mL methanol were added 245 mL 30% H$_2$O$_2$ and 720 mL 3.0N NaOH at room temperature. The mixture was heated to reflux for 1 hour. An additional 245 mL 30% H$_2$O$_2$ was added and the mixture was refluxed for an additional 45 minutes. The solution was diluted with brine then extracted three times with ether. The combined organic material was dried over MgSO$_4$, stripped of solvent in vacuo, and was flash chromatographed over silica eluting with 25% ethyl acetate in methylene chloride to give a white solid, R$_f$ 0.13 in 25% ethyl acetate in methylene chloride. The solid was stirred in 4 mL CH$_2$Cl$_2$ and 4 mL TFA over 4 hours. The volatiles were removed in vacuo and the crude material was flash chromatographed over silica eluting with 1:4:95 acetic acid/methanol/methylene chloride to give a white crystalline solid. R$_f$ 0.14 in 1:4:95 acetic acid/methanol/methylene chloride. $^1$H-NMR (300 MHz, CD$_3$OD): δ8.34 (m, 1H), 7.89–7.06 (m, 11H), 5.79 (s, 2H), 3.01 (3 line m, 2H), 1.81 (m, 2H), 1.49 (m, 2H), 0.95 (t, 3H). FABMS m/z 413 (M$^+$+1).

EXAMPLE 54

6-Isopropyl-2-propyl-3-(2'-(aminosulfonyl)(biphen-4-yl)methyl)-quinazolin-4(1H)-one Step 1: 6-Isopropyl-2-propyl-3-(2'-((tert-butylamino)-sulfonyl)(biphen-4-yl)methyl)-quinazolin-4(1H)-one 6-Isopropyl-2-propyl-quinolin-4(3H)-one (0.75 mmol) is added to a stirred suspension of sodium hydride (60% dispersion) (0.75 mmol) in dimethylformamide (3 ml) at 0° C. under nitrogen. The mixture is then stirred at room temperature until the solution is clear. A solution of 4'-(bromomethyl)biphenyl-2-tert-butylsulfonamide (0.832 mmol) in dimethylformamide (3 ml) is added dropwise and the solution is stirred at room temperature overnight. The solvent is removed in vacuo, and the residue is purified by flash chromatography (silica gel) to provide the desired titled product.

Step 2: 6-Isopropyl-2-propyl-3-(2'-(aminosulfonyl)-(biphen-4-yl)methyl)-quinazolin-4(1H)-one Anisole is added to a stirred solution of the compound from Step 1 (0.554 mmol) in trifluoroacetic acid (6 ml) under nitrogen at room temperature. The solution is stirred at room temperature for 8 h then the solvent removed in vacuo. Flash chromatography affords the titled product.

EXAMPLE 55

6-Isopropyl-2-propyl-3-(2'-((isopropylsulfonylamino)-sulfonyl-biphen-4-yl)methyl)quinazolin-4(1H)-one To a stirred suspension of NaH in dry DMF under nitrogen at room temperature is added 6-isopropyl-2-propyl-3-(2'-(aminosulfonyl(biphen-4-yl)methyl)-quinazolin-4-one. After stirring for 30 minutes at room temperature, isopropylsulfonylchloride is added, and the resulting mixture is stirred at room temperature overnight. The reaction mixture is poured into ice water, acidified with 5% citric acid solution and extracted with chloroform. The combined organic phase is washed with water and brine, and then dried over MgSO$_4$. Removal of the solvent in vacuo gives the crude product as a foam which is purified by flash-chromatography using silica gel to give the desired product.

EXAMPLE 56

6-Isopropyl-2-propyl-3-(2'-((dibenzylphosphonylamino)sulfonyl-biphen-4-yl)methyl)quinazolin-4(1H)-one To a stirred solution of 6-isopropyl-2-propyl-3-(2'-(aminosulfonyl-biphen-4-yl)methyl)quinazolin-4(1H)-one in dry THF is added n-BuLi at 0° C. After stirring for a few minutes at that temperature, a solution of dibenzylphosphorylchloride in THF is added, and the resulting mixture is stirred at room temperature overnight. The reaction mixture is concentrated under reduced pressure, and the residue is treated with 5% citric acid solution and extracted with methylene chloride. The organic phase is washed with water and brine, and then dried over MgSO$_4$. The crude product obtained after removal of the solvent is purified on silica-gel by flash-chromatography.

EXAMPLE 57

6-Isopropyl-2-propyl-3-(2'-((N-hydroxy-amino)sulfonyl-biphen-4-yl)methyl)-quinazolin-4(1H)-one Step 1: 6-Isopropyl-2-propyl-3-(2'-((O-tert-butyl-N-hydroxyamino)sulfonyl-biphen-4-yl)methyl)quinazolin-4(1H)-one 6-Isopropyl-2-propyl-quinazolin-4(1H)-one is added to a stirred suspension of sodium hydride in dimethylformamide at 0° C. under nitrogen. The mixture is then stirred at room temperature. A solution of 4'-bromomethylbiphenyl-2-(O-tert-butyl)-N-hydroxysulfonamide in dimethylformamide is added dropwise and the solution stirred at room temperature overnight. The crude product obtained after removal of the solvent in vacuo is purified by flash chromatography (silica gel) to give the titled compound.

Step 2: 6-Isopropyl-2-propyl-3-(2'-((N-hydroxyamino)sulfonyl-biphen-4-yl)methyl)quinazolin-4(1H)-one The compound obtained in Step 1 is treated with trifluoroacetic acid and a few drops of anisole at room temperature for several hours. Removal of the solvent in vacuo followed by recrystallization of the crude product from an appropriate solvent gives the titled product.

EXAMPLES 58 TO 65

The compounds of the Formula (II) exemplified in Table D are prepared from the appropriate substituted starting materials utilizing the general procedures outlined in the examples hereinabove and the noted schemes.

EXAMPLES 66 TO 76

The compounds of the formula (III) exemplified in Table E are prepared from the appropriately substituted starting material utilizing the general procedures outlined in the examples hereinabove and the noted schemes.

TABLE D

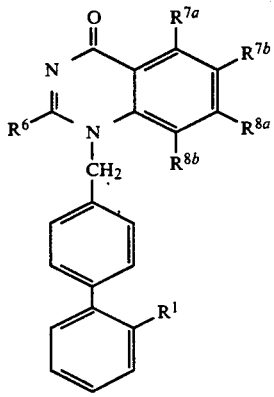

(II)

| Example # | R¹ | R⁶ | R⁷ᵃ | R⁷ᵇ | R⁸ᵃ | R⁸ᵇ | Scheme |
|---|---|---|---|---|---|---|---|
| 58 | —SO₂NHSO₂Me | Pr | Me | Me | H | H | 8 |
| 59 | —SO₂NHSO₂iPr | Pr | Me | H | H | H | 8 |
| 60 | (N—N—Ph triazole-sulfinamide) | Bu | H | H | iPr | H | 18-20 |
| 61 | (same as 60) | Pr | H | H | Me | H | 25 |
| 62 | —SO₂NHSO₂iPr | Pr | H | H | iPr | H | 8 |
| 63 | —SO₂NHP(O)(OCH₂Ph)OCH₂Ph | Bu | H | H | Me | H | 13 |
| 64 | (sulfamide ring with C=O) | Pr | H | H | iPr | H | 21 |
| 65 | (N—O isoxazole-NHSO₂Ph) | Bu | H | H | iPr | H | 11 |

TABLE E (III)

[Structure: substituted benzene ring with R7a, R7b, R8a, R8b substituents, N=C(R6)-N-C(=O) group, CH2 linker to biphenyl bearing R1]

| Example No. | R¹ | R⁶ | R⁷ᶜ | R⁷ᵈ | R⁸ᵃ | R⁸ᵇ | Scheme |
|---|---|---|---|---|---|---|---|
| 66 | —SO₂NHOH | Pr | Me | Me | Me | H | 26 |
| 67 | —SO₂NHOH | Pr | Me | H | iPr | H | 26 |
| 68 | —SO₂NHSO₂iPr | Pr | Me | H | Me | H | 8 |
| 69 | —SO₂NHSO₂Ph | Bu | Me | H | iPr | H | 8, 9 |
| 70 | —SO₂NHP(=O)(OCH₂Ph)(OCH₂Ph) | Pr | Me | H | iPr | H | 13 |
| 71 | [cyclic sulfamide with C=O, NH] | Bu | Me | Me | Me | H | 21 |
| 72 | [cyclic sulfamide with C=O, NH] | Pr | H | H | iPr | H | 21 |
| 73 | [oxadiazole with NHSO₂Ph] | Pr | H | H | Me | H | 21 |
| 74 | [cyclic N-Ph, S=O, NH] | Bu | H | H | iPr | H | 18-20 |
| 75 | [cyclic N-O, S=O, NH] | Pr | H | Me | H | Me | 16, 17 |
| 76 | [oxadiazole with NHSO₂CF₃] | Pr | H | H | Me | H | 23 |

EXAMPLES 77 TO 81

The compounds of the formula (IV) exemplified in Table F are prepared from the appropriate substituted starting material utilizing the general procedures outlined in the examples hereinabove and the noted schemes.

TABLE F (IV)

| Example No. | R¹ | R⁶ | R⁸ᵃ | Scheme |
|---|---|---|---|---|
| 77 | —SO₂NHOH | Pr | iPr | 26 |
| 78 | —SO₂NHOH | Bu | Me | 26 |
| 79 | —SO₂NHSO₂Ph | Pr | iPr | 8, 9 |
| 80 | (cyclic sulfonamide) | Pr | Me | 21 |
| 81 | (oxadiazole-NHSO₂Ph) | Bu | Me | 23 |

PREPARATION OF 6-N-SUBSTITUTED 3[(2'-(ALKOXYCARBONYL-SULPHONAMIDO)-BIPHEN-4-YL)METHYL]-2-ALKYL-QUINAZOLIN-4(3H)-ONES

EXAMPLE 82

6-Nitro-2-propyl-3-[(2'-(sulphonamido)biphen-4-yl)methyl]-quinazolin-4(3H)-one

To a solution of 6-nitro-2-propylquinazolin-4(1H)-one (2,44 g, 6.39 mmol) (prepared as described in Example 16) and 4'-bromomethylbiphenyl-2-tert-butyl-sulfonamide (1.56 g, 6.71 mmol) in DMF (50 mL) powdered K₂CO₃ was added (6.0 g) and the reaction was vigorously stirred for 72 hrs. The reaction mixture was diluted with water and the yellow precipitate formed was filtered and dried. To the crude intermediate anisole (1.5 mL) was added followed by the addition of TFA (25 mL). The solution was stirred overnight at room temperature, concentrated in vacuo, and the residue was dissolved in AcOEt and washed with 5% NaHCO₃. The crystalline product formed in the organic layer was filtered, washed with water and AcOEt to give the title compound.

¹H-NMR (CDCl₃): δ0.92–1.08 (t, J=7.4 Hz, 3H), 1.78–1.92 (m, 2H), 2.78 (t, J=7.4, 2H), 5.47 (s, 2H), 7.18–7.62 (m, 7H), 7.80 (d, J=9.0 Hz, 1H), 8.04–8.15 (m, 1H), 8.53 (dd, J=9.0, J=2.6 Hz, 1H), 9.09 (d, J=2.6 Hz, 1H).

EXAMPLE 83

2-Butyl-3-[(2'-(t-butylsulphonamido) biphen-4-yl) methyl]-6-nitro-quinazolin-4(3H)-one.

A mixture of 1.68 g (6.8 mmol) of 2-butyl-6-nitroquinazolin-4(1H)-one (prepared as described in Example 22), 2.88 g (7.5 mmol) of (4'-bromomethyl-biphenyl-2-tert-butyl-sulfonamide, 3.7 mL of 2N NaOH solution, 1.4 mL of 40% N-benzyl-N-dimethyl ammonium hydroxide in MeOH in 9 ml of toluene was heated at 90° C. for 18 hours. The suspension was cooled to room temperature and filtered. The residue was washed with 10 mL of water followed by 10 mL of EtOAc to provide the title compound. ¹H-NMR (CDCl₃-200 MHz): δ0.96 (t, 3H, J=7.3 Hz), 0.99 (s, 9H), 1.45 (m, 2H), 1.72 (m, 2H), 2.84 (t, 2H, J=8.1 Hz), 3.52 (s, 1H), 5.48 (bs, 2H), 7.29 (m, 3H), 7.52 (m, 3H), 7.80 (d, 1H, J=9 Hz), 8.16 (dd, 1H, J=7.2, 1.7 Hz), 8.54 (dd, 1H, J=2.5, 9.0 Hz), 9.17 (d, 1H, J=2.5 Hz).

The products of Examples 82 and 83 were then utilized as illustrated in Scheme 36, shown below (Rˣ=-ER⁶). Examples of preparations using each route are described hereinbelow.

SCHEME 36

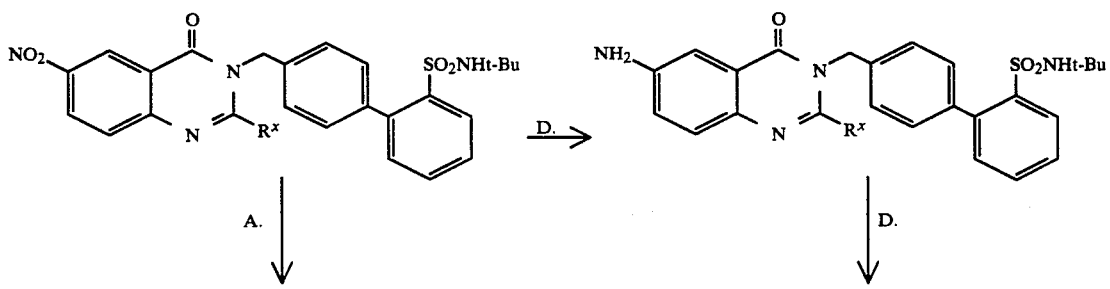

SCHEME 36 -continued

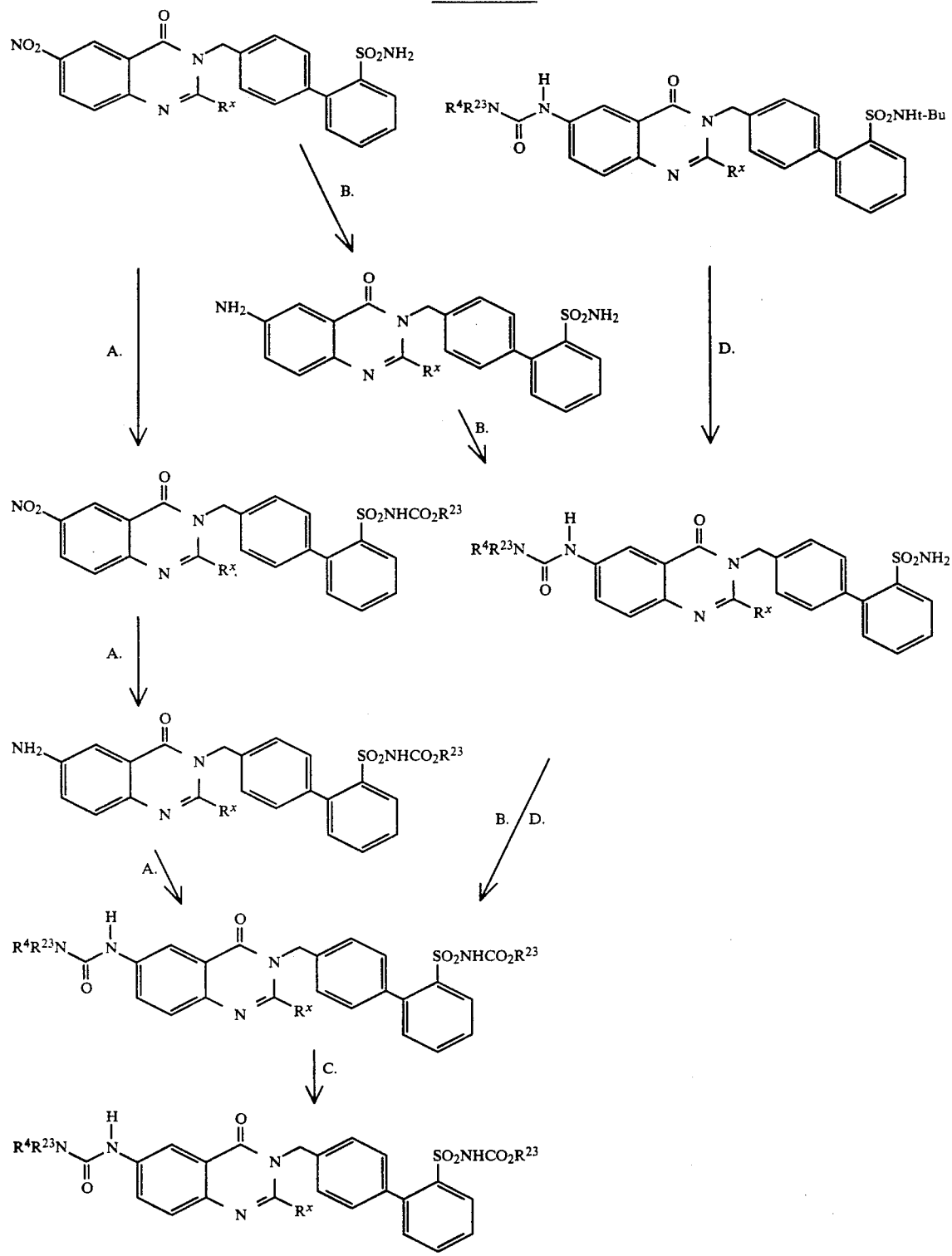

SYNTHESIS VIA SYNTHETIC ROUTE A

EXAMPLE 84

3-[(2'-(n-Butyloxycarbonylsulphonamido)biphen-4-yl)-methyl]-6-nitro-2-propyl-quinazolin-4(3H)-one To a stirred solution of the product of the Example 82 (100 mg, 0.21 mmol) and DMAP (40 mg, 0.33 mmol) in dry pyridine (3 mL) n-butylchloroformate (100 mL. 0.78 mmol) was added at room temperature and stirring was continued overnight. Dilute HCl was added and the product was extracted with AcOEt. Purification by silica gel chromatography provided the title compound.

$^1$H-NMR (CDCl$_3$): δ0.81 (t, J=7.2 Hz, 3H), 1.00–1.26 (m, 5H), 1.36–1.52 (m, 2H), 1.78–1.96 (m, 2H), 2.84 (t, J=7.2 Hz, 2H), 4.00 (t, J=6.6 Hz, 2H), 5.46 (s, 2H), 7.08 (bs, 1H), 7.21–7.36 (m, 4H), 7.51–7.68 (m, 3H), 7.77 (d, J=7.8 Hz, 1H), 8.24 (d, J=7.8 Hz, 1H), 8.51 (dd, J=9.6, J=2.6 Hz, 1H), 9.11 (d, J=2.6 Hz, 1H).

EXAMPLE 85

6-Amino-3-[(2'-(n-butyloxycarbonylsulphonamido)-biphen-4-yl)methyl]-2-propyl-quinazolin-4(3H)-one The product of the Example 84 (63 mg, 0.11 mmol) was hydrogenated overnight under 1 atm $H_2$ in dioxane (3 mL) in the presence of 10% Pd on carbon catalyst. The reaction mixture was filtered through Celite and evaporated. Purification with silica gel chromatography provided the title compound. $^1$H-NMR (CDCl$_3$/CD$_3$OD- 2/1): δ0.74 (t, J=7.4 Hz, 3H), 0.95–1.22 (m, 5H), 1.30–1.42 (m, 2H), 1.71–1.90 (m, 2H), 2.76 (t, J=8.0 Hz, 2H), 3.88 (t, J=6.6 Hz, 2H), 5.40 (s, 2H). 7.08–7.64 (m, 10H), 8.17 (dd, J=9.4, J=1.6 Hz, 1H).

EXAMPLE 86

6-[(N-n-Butylcarbamoyl)amino]-3-[(2'-(n-butyloxy-carbonylsulphonamido)biphen-4-yl)methyl]-2-propyl-quinazolin-4(3H)-one To the solution of the product of the Example 85 (16.3 mg, 0.03 mmol) in CH$_2$Cl$_2$/dioxane 1/1 (1.5 mL) n-butylisocyanate (0.1 mL, 0.89 mmol) was added at room temperature. After 48 hrs. the reaction mixture was purified by silica gel chromatography to provide the title compound. $^1$H-NMR (CDCl$_3$/CD$_3$OD- 2/1): δ0.75 (t, J=7.0 Hz, 3H), 0.83–1.20 (m, 8H), 1.26–1.54 (m, 6H), 1.73–1.89 (m, 2H), 2.81 (t, J=7.4 Hz, 2H), 3.18 (t, J=7.0 Hz, 2H), 3.90 (t, J=6.6 Hz, 2H), 5.41 (s, 2H), 7.13 (d, J=8.1 Hz, 2H), 7.21–7.30 (m, 3H), 7.42–7.64 (m, 4H), 7.92–8.06 (m, 2H), 8.16 (dd, J=7.8, J=1.4 Hz, 1H).

SYNTHESIS VIA SYNTHETIC ROUTE B

EXAMPLE 87

[6-(N-Ethylcarbamoyl)-amino]-2-propyl-3-[(2'-(sulphonamido) biphen-4-yl) methyl]-quinazolin-4(3H)-one The product of the Example 82 (1.77 g, 3.70 mmol) was hydrogenated under 1 atm $H_2$ in dioxane (3 mL) in the presence of 10% Pd on carbon catalyst until both the starting material and the reduction intermediate were consumed as monitored by TLC (CH$_2$Cl$_2$/MeOH-20/1). The reaction mixture was filtered through Celite and evaporated. The so obtained crude amine was dissolved in CH$_2$Cl$_2$ and ethyl isocyanate (2.0 mL, 25 mmol) was added. After 36 hrs. at room temperature, the precipitate formed was filtered off, boiled with 10 mL of MeOH and cooled and filtered to provide the title compound.

$^1$H-NMR (CDCl$_3$/CD$_3$OD-2/1): δ0.99 (t, J=7.2 Hz, 3H), 1.13 (t, J=7.4 Hz, 3H), 1.66–1.87 (m, 3H), 2.70–2.82 (m, 2H), 3.22 (q, J=7.2 Hz, 2H), 5.43 (s, 2H), 7.15–7.28 (m, 3H), 7.35–7.62 (m, 6H), 7.61–8.11 (m, 3H).

EXAMPLE 88

3-[(2'-(n-Butyloxycarbonylsulphonamido) biphen-4-yl)-methyl]-6-[(N-ethylcarbamoyl)-amino]-2-propyl-quinazolin-4(3H)-one To a stirred solution of the product of the Example 87 (45 mg, 0.092 mmol) and DMAP (10 mg, 0.082 mmol) in dry pyridine (1 mL) n-butylchloroformate (0.05 mL, 0.36 mmol) was added at room temperature and stirring was continued overnight. Dilute HCl was added and the product was extracted with AcOEt. Purification by silica gel chromatography provided the title compound.

$^1$H-NMR (CDCl$_3$): δ0.75(t, J=7.0 Hz, 3H), 0.95–1.22 (m,8H), 1.38–1.54 (m,2H),1.72–1.90(m, 2H), 2.78(t, J=7.4 Hz, 2H), 3.22(q, J=7.2 Hz, 2H), 3.89(t, J=6.6 Hz, 2H), 5.40(s, 2H), 7.12(d, J=8.2 Hz, 2H), 7.22–7.30(m, 3H), 7.45–7.66(m, 3H), 7.97–8.06(m, 2H), 8.17(dd, J=7.6, 1.6 Hz, 1H).

SYNTHESIS VIA SYNTHETIC ROUTE C

EXAMPLE 89

3-[(2'-(2-N,N-Dimethylamino(ethoxycarbonylsulphonamido))biphen-4-yl)methyl]-6-[(N-ethylcarbamoyl)amino]-2-propyl-quinazolin-4(3H)-one A solution of the product of the Example 88 (7 mg, 0.011 mmol) was heated in N,N-dimethylaminoethanol (0.5 mL) at 100° overnight. Excess of N,N-dimethylaminoethanol was removed in vac. and the product was purified on silica gel to provide the title compound.

$^1$H-NMR (CDCl$_3$/CD$_3$OD-2/1): δ0.98 (t, J=7.2 Hz, 3H), 1.09 (t, J=7.2 Hz, 3H), 1.73–1.84 (m,2H), 2.73 (s, 6H), 3.13–3.21 (m, 4H), 3.25–3.33 (m, 2H), 3.80–3.86(m, 2H), 5.35(s,2H), 7.04(d, J=8.1 Hz, 2H), 7.17(dd, J=7.2, 1.8 Hz, 1H), 7.32(d, J=8.1 Hz, 2H), 7.39–7.67(m,3H), 7.64(dd, J=9.0, J=2.4 Hz,1H), 8.11(dd, J=7.8, 1.5 Hz, 1H),8.22(d, J=2.4 Hz, 1H).

SYNTHESIS VIA SYNTHETIC ROUTE D

EXAMPLE 90

6-Amino-2-butyl-3-[(2'-(t-butylsulphonamido)-biphen-4-yl) methyl]-quinazolin-4(3H)-one The product of the Example 83 was hydrogenated analogously to the procedure described in Example 85 to provide the title compound.

EXAMPLE 91

2-Butyl-6-[(N-isopropyl-N-methylcarbamoyl)-amino]-3-[(2'-(t-butylsulphonamido) biphen-4-yl)methyl]-quinazolin-4(3H)-one To a flask containing triphosgene (100 mg, 0.34 mmol) a solution of the product of the Example 90 (185 mg. 0.357 mmol) in pyridine (2 mL) was cannulated (vigorous reaction) and the stirring was continued for 1 hr. at room temp. N-Isopropyl-N-methylamine was added and after 2 hrs the reaction mixture was diluted with water and extracted with AcOEt/THF mixture. The intermediate product was isolated by purification on silicagel Chromatotron plate (CH$_2$Cl$_2$/MeOH-20/1) to give 140 mg of yellow glass which was heated with the excess of N-isopropyl-N-methylamine (2.0 mL) in pressure vial at 100°–110° for 24 hrs. The mixture was evaporated to dryness and the residue was separated on silica gel Chromatotron plate (CH$_2$Cl$_2$/MeOH-20/1) to yield solid material which was deprotected overnight at room temp. with TFA as described in Example 1. After removing TFA in vac. the residue was separated on silicagel Chromatotron plate (CH$_2$Cl$_2$/MeOH-20/1) to give the title product and the 6-amino product.

$^1$H-NMR (CDCl$_3$): δ0.90(t, J=7.2 Hz, 3H), 1,15(d, J=8.0 Hz, 6H), 1.30–1.49(m, 2H), 1.64–1.83(m, 2H), 2.72(t, J=7.3 Hz, 2H), 4.50–4.63(m, 1H), 4,72(s, 2H), 5.36(s, 2H), 6.91(s, 1H), 7.14–7.28(m, 3H), 7.33–7.58(m, 5H), 7.85(d,J=2.5 Hz, 1H).8.03–820(m, 2H).

EXAMPLE 92

2-Butyl-[(N-isopropyl-N-methylcarbamoyl)-amino]-3-[(2'-(n-butyloxycarbonylsulphonamido) biphen-4-yl) methyl]-quinazolin-4(3H)-one

From the product of the Example 10 the title product was obtained as in the Example 91 Purification on silica gel (CH$_2$Cl$_2$/MeOH-30/1) gave the title product.

$^1$H-NMR (CDCl$_3$/CD$_3$OD-2/1): δ0.77(t, J=7.3 Hz, 3H), 0.92(t, J=7.2 Hz, 3H), 1.03–1.21 (m, 8H), 1.30–1.51(m, 4H), 1.61–1.81(m, 2H), 2.77–2.90(m, 5H), 3.91(t, J=6.4 Hz,2H), 4.44–4.59(m, 1H), 5.44(s, 2H), 7.14(d, J=8.8 Hz, 2H), 7.21–7.31(m,3H), 7.43–7.65(m, 3H), 7.98–8.20(m, 3H).

The following compounds, Examples 93–104, were prepared utilizing the protocols described above. Mass spec. data is also provided for example compounds previously described.

1H, J=8.6 Hz), 8.07 (dd, 1H, J=2, 8.7 Hz).1H, J=8.6 Hz), 8.07 (dd, 1H, J=2, 8.7 Hz).

STEP 2: 6-Iodo-2-propyl-3-[(2'-(t-butylsulphonamido)biphen-4-yl)methyl]-quinazolin-4(3H)-one Following the general procedure described above 6-iodo-2-propyl-quinazolin-4(3H)-one was alkylated with 4'-bromomethylbiphenyl-2-tert-butylsulfonamide to give, following flash chromatography over silica gel eluting with 20% EtOAc/hexanes, the title compound. $^1$H-NMR (CDCl$_3$, 200 MHz): δ0.97 (s, 9H), 1.01 (t, 3H, J=7.3 Hz), 1.82 (m, 2H), 2.73 (t, 2H, J=7.8 Hz), 5.43 (bs, 2H), 7.15–7.65 (m, 8H), 7.99 (dd, 1H, J=2.1, 8.6 Hz), 8.15 (dd, 1H, J=1.46, 7.5 Hz), 8.62 (d, 1H, J=2Hz).

STEP 3: 6-(2-Pyridyl)-2-propyl-3-[(2'-(t-butylsulphonamido)biphen-4-yl)methyl]-quinazolin-4(3H)-one A solution of 0.5 g (0.8 mmol) of 6-iodo-2-propyl-3-[(2'-(t-butylsulphonamido)biphen-4-yl)methyl]-quinazo-

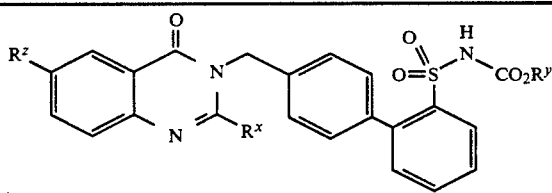

| R$^x$ | R$^y$ | R$^z$ | FAB-MS | Method | Example |
|---|---|---|---|---|---|
| Pr | butyl | NO2 | 578 | A | 84 |
| Pr | butyl | NH2 | 548 | A | 85 |
| Pr | butyl | BuNHCONH | 647 | A | 86 |
| Pr | butyl | EtNHCONH | 619 | B | 88 |
| Pr | 2-N,N-dimethylaminoethyl | EtNHCONH | 634 | C | 89 |
| Bu | butyl | iPrN(Me)CONH | 661 | D | 92 |
| Pr | butyl | iPrNHCONH | 633 | B | 93 |
| Pr | propyl | iPrNHCONH | 619 | B | 94 |
| Pr | pentyl | iPrNHCONH | 647 | B | 95 |
| Pr | butyl | MeNHCONH | 605 | B | 96 |
| Pr | 3-methylbutyl | EtNHCONH | 633 | B | 97 |
| Pr | 3-methylbutyl | MeNHCONH | 619 | B | 98 |
| Pr | butyl | n-PrNHCONH | 633 | A | 99 |
| Pr | 2-cyclopropylethyl | EtNHCONH | 631 | B | 100 |
| Pr | 3,3-dimethylbutyl | EtNHCONH | 647 | C | 101 |
| Bu | pentyl | iPrNHCONH | 661 | B | 102 |
| Bu | butyl | iPrNHCONH | 647 | B | 103 |
| Bu | 2-methoxyethyl | iPrNHCONH | 635 | B | 104 |
| Bu | 3-methylbutyl | EtNHCONH | 676 | B | 105 |
| Bu | butyl | EtNHCONH | 634 | B | 106 |
| Pr | benzyl | EtNHCONH | 654 | C | 107 |
| Pr | 3-methylbutyl | 2-furoyl-CONH | 657 | A | 108 |
| Pr | ethoxyethyl | EtNHCONH | 636 | B | 109 |
| Pr | 2-methoxyethyl | iPrNHCONH | 649 | B | 110 |
| Et | 2-cyclopropylethyl | EtNHCONH | 618 | B | 111 |
| Et | 3-methylbutyl | EtNHCONH | 620 | B | 112 |
| Pr | 2-methoxybenzyl | EtNHCONH | 683 | B | 113 |
| Pr | 3-methylbutyl | morpholino-CONH— | 675 | B | 114 |
| Et | benzyl | EtNHCONH | 639 | B | 115 |
| Pr | 2-cyclopentylmethyl | EtNHCONH | 618 | C | 116 |

Preparation of 6-aryl and 6-heteroaryl-3-[(2'-(alkoxycarbonylsulphonamido)biphen-4-yl)methyl]-2-alkyl-quinazolin-4(3H)-ones

EXAMPLE 117

6-(2-Pyridyl)-2-propyl-3-[(2'-(n-butyloxycarbonylsulphonamido)biphen-4-yl)methyl]-quinazolin-4(3H)-one

STEP 1: 6-Iodo-2-propyl-quinazolin-4(3H)-one

Following the procedure described as in the preparation of 6-nitro-2-propylquinazolin-4(1H)-one above. 25 g of 5-iodoanthranilic acid was converted into the title compound. $^1$H-NMR (CDCl$_3$, 200 MHz): δ1.02 (t, 3H, J=7.4 Hz), 1.81 (m, 2H), 2.63 (t, 2H, J=7.4 Hz), 7.40 (d, lin-4(3H)-one in 3 mL of dry DMF under nitrogen was treated with 0.24 g (1.1 mmol) of 2-trimethylstannylpyridine and 10 mg (0.01 mmol) bis(triphenylphophine)-palladium dichloride. The solution was heated at 80°–90° C. for 2 hours to give a black solution. The reaction mixture was concentrated in vacuo and the residue was purified by flash chromatography over silica gel eluting with 40% EtOAc/hexanes to give the title compound. $^1$H-NMR (CDCl$_3$, 200 MHz): δ0.98 (s, 9H), 1.06 (t, 3H,), 1.78 (m, 2H), 2.76 (t, 2H,), 5.49 (bs, 2H), 7.29 (m, 7H), 8.50 (m, 8H), 7.75–7.91 (m, 2H), .8.15 (dd,1H), 8.57 (dd, 1H), 8.71 (dm, 1H), 8.82 (d, 1H).

STEP 4: 6-(2-Pyridyl)-2-propyl-3-[(2'-(sulphonamido)biphen-4-yl)methyl]-quinazolin-4(3H)-one 0.15 g (0.26 mmol) of 6-(2-pyridyl)-2-propyl-3-[(2'-(t-butylsulphonamido)biphen-4-yl)methyl]quinazolin-4(3H)-one was stirred overnight in the presence of 0.5 mL of anisole and 5 mL of trifluoroacetic acid. The reaction mixture was concentrated in vacuo and the residue was purified by flash chromatography to give the title compound as a white solid. $^1$H-NMR (CDCl$_3$, 200 MHz): δ1.06 (t, 3H, J=7.4 Hz), 1.90 (m, 2H), 3.81 (t, 2H), 4.20 (bs, 2H), 5.40 (bs, 2HO, 7.28–7.62 (m, 8H), 7.85 (d, 1H, J =8.6 Hz), 7.96 (m, 2H), 8.14 (dd, 1H, J=1.6, 9.3 Hz), 8.50 (dd, 1H, J=2.0, 8.5 Hz), 8.84 (d, 1H, J=2 Hz).

STEP 5: 6-(2-Pyridyl)-2-propyl-3-[(2'-(n-butyloxycarbonylsulphonamido)biphen-4-yl)methyl]-quinazolin-4(3H)-one 0.066 g (0.13 mmol) of 6-(2-pyridyl)-2-propyl-3-[(2'-(sulphonamido)biphen-4-yl)methyl]quinazolin-4(3H)-one was dissolved in 1 mL of pyridine and treated with 65 mg of DMAP and 100 μL of n-butylchloroformate and stirred over night. The reaction mixture was diluted with 20 mL of EtOAc and washed with saturated NH$_4$Cl solution (1×5 mL), water (1×5 mL), brine (1×5 mL) and was dired over MgSO$_4$. The mixture was filtered and concentrated in vacuo to give a residue which was purified by Chromatotron chromatography eluting with 5% MeOH/CH$_2$Cl$_2$ to give the title compound.

$^1$H-NMR (CDCl$_3$, 200 MHz): 0.78 (t, 3H, J=7.3 Hz), 1.05 (t, 3H, J=7.3 Hz), 1.13 (m, 2H), 1.40 (m, 2H), 1.89 (m, 2H), 2.81 (t, 2H, J=8.0 Hz), 3.95 (t, 2H, J=6.5a Hz), 5.49 (bs, 2H), 7.29 (m, 6H), 7.59 (m, 2H), 7.82 (m, 3H), 8.26 (dd, 1H, J=1.4, 7.6 Hz), 8.54 (dd, 1H, J=8.6, 1.4 Hz), 8.72 (d, 1H, J=4.4 Hz), 8.83 (d, 1H, J=2.0 Hz).

The following compounds, having the general formula of the compounds of Examples 93–116, were prepared utilizing the above methods:

| Example | R$^x$ | R$^y$ | R$^z$ | MW |
|---|---|---|---|---|
| 118 | Pr | Bu | 2-Pyr | 610 |
| 119 | Pr | Bu | 3-Pyr | 610 |
| 120 | Pr | Bu | 4-Me-Ph | 635 |
| 120A | Pr | 3-methylbutyl | 2-Pyr | 624 |

PREPARATION OF 6-((PIPERAZINYL AND IMIDAZOLYL)METHYL)-2-PROPYL-QUINAZOLIN-4(3H)-ONES

EXAMPLE 121

6-(N1(N2-Cyclopropylcarbonyl)piperazinyl)methyl-2-propyl-3-[(2'-(n-butyloxycarbonylsulphonamido)biphen-4-yl)methyl]-quinazolin-4(3H)-one STEP 1: 6-Bromomethyl-2-propyl-quinazolin-4(3H)-one The product of Example 8 was converted into the title compound in the manner described in Example 18.

$^1$H-NMR (CDCl$_3$, 200 MHz): 1.07 (t, 3H, J=7.4 Hz), 1.90 (m, 2H), 2.73 (t, 2H, J=7.1 Hz), 4.61 (s, 2H), 7.5–8.2 (m, 3H).

STEP 2: 6-(N1(N2-t-Butoxycarbonyl)piperazinyl)methyl-2-propylquinazolin-4(3H)-one To a solution of 0.64 g (2.3 mmol) of 6-bromomethyl-2-propyl-quinazolin-4(3H)-one in 7 mL of dry DMF was added 0.64 g powdered K$_2$CO$_3$ and 1.64 g (3.4 mmol) of N1-CBZ-piperazine. The reaction mixture was stirred over night, diluted with 50 mL of EtOAc and washed with water (2×10 mL) and brine (1×10 mL). The organic phase was dried over MgSO$_4$, filtered and concentrated in vacuo. The residue was purified by flash chromatography over silica gel eluting with 5% MeOH/CH$_2$Cl$_2$ to provide the title compound.

$^1$H-NMR (CDCl$_3$, 200 MHz):1.07 (t, 3H, J=7.4 Hz), 1.89 (m, 2H), 2.42 (t, 4H, J=4.9 Hz), 2.77 (t, 2H, J=7.2 Hz), 3.52 (t, 4H, J=4.9 Hz), 3.64 (s, 2H), 5.12 (s, 2H), 7.32 (s, 4H), 7.65 (d, 1H, J=8.3), 7.77 (d, 1H, J=9.7 Hz), 8.16 (s, 1H), 11.71 (bs, 1H).

STEP 3: 6-(N1(N2-CBZ)piperazinyl)methyl-2-propyl-3-[(2'-(t-butylsulphonamido)biphen-4-yl)methyl]-quinazolin-4(3H)-one To a suspension of 0.4 g (0.95 mmol) of 6-(N1(N2-butoxycarbonyl)piperazinyl)methyl-2-propylquinazolin-4(3H)-one in 3 mL of dry DMF was added 0.24 mL (0.24 mmol) of a 1M solution of sodium hexamethydisilazide in THF at 0° C. to give a pale yellow solution. After 10 minutes a solution of 0.15 g (0.27 mmol) of 4'-bromomethylbiphenyl-2-tert-butylsulfonamide was added in 1 mL of dry DMF. The solution was stirred at room temperature over night, diluted with 25 mL of EtOAc and washed with water (2×20 mL) followed by brine (1×10 mL) and dried over MgSO$_4$. The solution was filtered and the filtrate was concentrated in vacuo and the residue was purified by flash chromatography over silica gel eluting with 65% EtOAc/hexanes to provide the title compound.

$^1$H-NMR (CDCl$_3$, 200 MHz): 0.97 (s, 9H), 1.03 (t, 3H), 1.88 (m, 2H), 2.42 (bs, 4H), 2.75 (t, 2H), 3.52 (m, 4H), 3.63 (s, 2H), 5.12 (s, 2H), 5.46 (bs, 2H), 7.28 (d, 2H, J=6.3 Hz), 7.34 (bs, 4H), 7.42–7.85 (m, 8H), 8.19 (bm, 2H).

STEP 4: 6-(N1(N2-Cyclopropylcarbonyl)-piperazinyl)methyl-2-propyl-3-[(2'-(n-butyloxycarbonylsulphonamido)biphen-4-yl)methyl]-quinazolin-4(3H)-one 0.5 g of 6-(N1(N2-CBZ)piperazinyl)methyl-2-propyl-3-[(2'-(t-butylsulphonamido)biphen-4-yl)methyl]-quinazolin-4(3H)-one was stirred over night in 5 mL of trifluoroacetic acid and 0.5 mL of anisole. The reaction mixture was concentrated in vacuo and the residue was purified by flash chromatography over silica gel to give 0.38 g of a colorless foam. 0.146 g of the product was stirred over 3 days with 220 uL of n-butyl choroformate in 1.5 mL of pyridine and a catalytic amount of DMAP. The reaction mixture was concentrated in vacuo and the residue was dissolved in MeOH. The MeOH solution was applied a column of Amberlyst A-27 resin in the basic cycle. The column was eluted with MeOH until the eluant was neutral. The column was then eluted with 5% Acetic acid to give the product as a colorless foam. The sulfonylcarbamate was hydrogenated over night at atmospheric pressure in MeOH in the presence of 10% Pd/C. The reaction mixture was filtered and concentrated in vacuo to give a glass. 30 mg of the resulting piperazine was acylated by stirring over night with 1 mL of CH$_2$Cl$_2$ and 17 ul of diisopropylethyl amine and 7 uL of cyclopropyl carbonyl chloride. The reaction mixture was diluted with 20 mL of EtOAc and washed with saturated NH$_4$Cl (1×5 mL) and brine (1×5 mL). The reaction mixture was dried over MgSO$_4$, filtered and concentrated in vacuo. The product was purified by silica gel chromatography eluting with 5% MeOH/CH$_2$Cl$_2$ to provide the title compound.

¹H-NMR (CDCl₃, 200 MHz): 0.7–0.85 (m, 2H), 0.80 (t, 3H, J=7.6 Hz), 0.95 (m, 2H), 1.03 (t, 3H, J=7.2 Hz), 1.15 (m, 2H), 1.41 (m, 2H), 1.72 (m, 1H), 1.72 (m, 2H), 2.49 (m, 4H), 2.78 (t, 2H, J=7.8 Hz), 3.65 (bs, 4H), 3.97 (t, 2H, J=6.6 Hz), 5.46 (bs, 2H), 7.26 (m, 4H), 7.50–7.82 (m, 4H), 8.20 (d, 1H, J=1.4 Hz), 8.24 (dd, 1H, J=1.41, 9.12 Hz).

EXAMPLE 122

6-(N1(N2-acetyl)piperazinyl)methyl-2-propyl-3-[(2'-(n-butyloxycarbonylsulphonamido)biphen-4-yl)methyl]-quinazolin-4(3H)-one Following the method described in Example 117, Step 4, the title compound was prepared by acylation of the piperazine from Example 108, Step 3, with acetyl choride in place of cyclopropylcarbonyl choride.

EXAMPLE 123

6-(N1-Imidazolylmethyl)-2-propyl-3-[(2'-(n-butyloxycarbonylsulphonamido)biphen-4-yl)methyl]-quinazolin-4(3H)-one STEP 1: 6-(N1-Imidazolylmethyl)-2-propyl-quinazolin-4(3H)-one To a solution of 0.20 g (3 mmol) of imidazole in 3 mL of dry DMF was added 79 mg of 80% NaH (3.3 mmol). After hydrogen evolution had ceased a solution of 0.28 g (1 mmol) of 6-bromomethyl-2-propylquinazolin-4(3H)-one was added in 1 mL of DMF. The reaction mixture was heated at 60° C. for 6 hours and was then stirred at room temperature for a further 2 days. The mixture was diluted with 25 mL of EtOAc and washed with saturated NaHCO₃ (1×5 mL), water (1×5 mL) and brine (1×5 mL) and was dried over MgSO₄. The solution was filtered and concentrated in vacuo and the residue was purified by flash chromatography over silica gel eluting with 7% MeOH/CH₂Cl₂ to provide the title compound.

¹H-NMR (CDCl₃, 200 MHz): δ1.06 (t, 3H, J=7.6 Hz), 1.83 (m, 2H), 2.70 (t, 2H, J=7.8 Hz), 5.23 (s, 2H), 6.92 (s, 1H), 7.10 (s, 1H), 7.47–7.70 (m, 3H), 8.11 (m, 1H).

STEP 2: 6-(N1-Imidazolylmethyl)-2-propyl-3-[(2'-t-butylsulphonamido)biphen-4-yl)methyl]-quinazolin-4(3H)-one 6-(N1-imidazolylmethyl)-2-propyl-quinazolin-4(3H)-one was alkylated with 4'-bromomethylbiphenyl-2-tert-butyl-sulfonamide to give the title compound in the manner described above, Example 121, Step 3, to give the title product.

STEP 3: 6-(N1-Imidazolylmethyl)-2-propyl-3-[(2'-(n-butyloxycarbonylsulphonamido)biphen-4-yl)methyl]-quinazolin-4(3H)-one Deprotection of the t-butyl sulfonamide and acylation of the resulting sulfonamide as described in Example 117, Steps 4 and 5, with n-butylchloroformate gave the title compound following purification by chromatography over silica eluting with 5% MeOH/CH₂Cl₂.

¹H-NMR (CDCl₃, 400 MHz): δ0.79 (t, 3H, J=7.36 Hz), 1.01 (t, 3H, J=7.4 Hz), 1.20 (m, 2H), 1.41 (m, 2H), 1.83 (m, 2H), 2.74 (t, 2H, J=7.4 Hz), 3.64 (t, 2H, J=6.6 Hz), 5.21 (s, 2H), 5.40 (bs, 2H), 6.92 (s, 1H), 7.09 (s, 1H), 7.16 (d, 2H, J=8 Hz), 7.25 (d, 2H, J=8 Hz), 7.40–7.65 (m, 6H), 8.16 (s, 1H), 8.20 (dd, 1H, J=1.4, 8.0 Hz).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 2-Propyl-6-[(N-ethyl-carbamoyl)amino]-3-[(2'-(3,3-dimethylbutyl)-oxycarbonylsulphonamido)-biphen-4-yl)methyl]-quinazolin-4(3H)-one | 50 |
| Lactose | 149 |
| Magnesium stearate | 1 |
| Capsule (size No. 1) | 200 |

2-Propyl-6-[(N-ethylcarbamoyl)amino]-3-[(2'-(3,3-dimethylbutyl)oxycarbonylsulphonamido)biphen-4-yl)methyl]-quinazolin-4(3H)-one (compound of Example 101) can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-propyl-6-[(N-ethylcarbamoyl)amino]-3-[(2'-(3,3-dimethylbutyl)oxycarbonylsulphonamido)biphen-4-yl)methyl]-quinazolin-4(3H)-one (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of 2-propyl-6-[(N-ethylcarbamoyl)amino]-3-[(2'-(3,3-dimethylbutyl)oxycarbonylsulphonamido)biphen-4-yl)methyl]quinazolin-4(3H)-one (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 2-propyl-6-[(N-ethylcarbamoyl)amino]-3-[(2'-(3,3-dimethylbutyl)oxycarbonylsulphonamido)biphen-4-yl)methyl]quinazolin-4(3H)-one (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-propyl-6-[(N-ethylcarbamoyl)amino]-3-[(2'-(3,3-dimethylbutyl)oxycarbonylsulphonamido)biphen-4-yl)methyl]-quinazolin-4(3H)-one (5.42 mg), sodium phosphate dibasic anhydrous (11.4 mg) benzyl alcohol (0.01 mL) and water for injection (1.0 mL). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of formula (I):

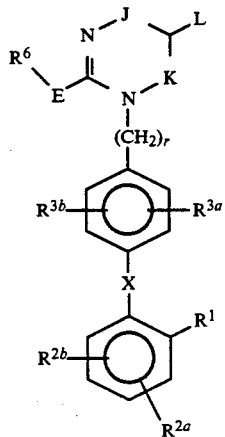

or a pharmaceutically acceptable salt thereof, wherein:

L is connected with J or K to form an aromatic ring as defined below;

J and L are connected together to form a 6 carbon aromatic ring substituted with $R^{7a}$, $R^{7b}$, $R^{8a}$ and $R^{8b}$;

K is —C(=O)—;

$R^1$ is —$SO_2NHCO_2R^{23}$;

$R^{2a}$ and $R^{2b}$ are each independently
 (a) H,
 (b) halogen, (Cl, Br, I, F),
 (c) $NO_2$,
 (d) $NH_2$,
 (e) $C_1$-$C_4$-alkylamino,
 (f) di($C_1$-$C_4$-alkyl)amino,
 (g) $SO_2NHR^9$,
 (h) $CF_3$,
 (i) $C_1$-$C_6$-alkyl,
 (j) $C_1$-$C_6$-alkoxy,
 (k) ($C_1$-$C_6$-alkoxy)—$CH_2$—,
 (l) ($C_1$-$C_6$-alkyl-S)—$CH_2$—,
 (m) $C_1$-$C_6$-alkyl—S—,
 (n) —$CH_2NR^9R^9$,
 (o) $C_2$-$C_6$-alkenyl,
 (p) $C_2$-$C_6$-alkynyl;
 (q) aryl as defined below,
 (r) aryl($C_1$-$C_4$-alkyl), or
 (s) $C_3$-$C_7$-cycloalkyl;

$R^{3a}$ is
 (a) H,
 (b) halogen (Cl, Br, I, F),
 (c) $C_1$-$C_6$-alkyl,
 (d) $C_1$-$C_6$-alkoxy, or
 (e) $C_1$-$C_6$-alkoxyalkyl;

$R^{3b}$ is
 (a) H,
 (b) halogen (Cl, Br, I, F),
 (c) $NO_2$,
 (d) $C_1$-$C_6$-alkyl,
 (e) $C_1$-$C_6$-acyloxy, or
 (f) $C_3$-$C_7$-cycloalkyl,
 (g) $C_1$-$C_6$-alkoxy,
 (h) —$NHSO_2R^4$,
 (i) hydroxy($C_1$-$C_4$-alkyl),
 (j) aryl($C_1$-$C_4$-alkyl),
 (k) $C_1$-$C_4$-alkylthio,
 (l) $C_1$-$C_4$-alkyl sulfinyl,
 (m) $C_1$-$C_4$-alkyl sulfonyl,
 (n) $NH_2$,
 (o) $C_1$-$C_4$-alkylamino,
 (p) di($C_1$-$C_4$-alkyl)amino,
 (q) fluoro-$C_1$-$C_4$-alkyl-,
 (r) —$SO_2$—$NHR^9$,
 (s) aryl as defined below,
 (t) furyl,
 (u) $CF_3$,
 (v) $C_2$-$C_6$-alkenyl, or
 (w) $C_2$-$C_6$-alkynyl;

wherein aryl is phenyl or naphthyl optionally substituted with one or two substituents selected from the group consisting of halogen(Cl, Br, I, F), $N(R^4)_2$, $CO_2R^4$, $C_1$-$C_4$-alkyl, $C_1$-$C_4$-alkoxy, $NO_2$, $CF_3$, $C_1$-$C_4$-alkylthio, OH, —$SO_2NR^9R^{10}$, $C_3$-$C_7$-cycloalkyl, $C_3$-$C_{10}$-alkenyl, and —$S(O)_x(C_1$-$C_4$-alkyl);

$R^4$ is H, aryl as defined above, straight chain or branched $C_1$-$C_6$ alkyl optionally substituted with aryl as defined above, or heteroaryl, wherein heteroaryl is an unsubstituted, monosubstituted or disubstituted heteroaromatic 5 or 6 membered ring which can contain one or two heteroatoms selected from the group consisting of N, O, and S, and wherein the substituents are members selected from the group consisting of —OH, —SH, $C_1$-$C_4$-alkyl, $C_1$-$C_4$-alkoxy, —$CF_3$, halogen (Cl, Br, I, F), and $NO_2$;

$R^{4a}$ is aryl as defined above, $C_1$-$C_6$-alkyl, or aryl-$C_1$-$C_6$-alkyl $R^5$ is H,

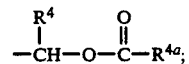

E is a single bond, —$NR^{13}(CH_2)_s$—, —$S(O)_x(CH_2)_s$— where x is 0 to 2 and s is 0 to 5, —$CH(OH)$—, —O—, or CO—;

$R^6$ is
 (a) aryl,
 (b) straight chain or branched $C_1$-$C_6$-alkyl, $C_2$-$C_5$-alkenyl or $C_2$-$C_5$-alkynyl each of which can be optionally substituted with a substituent selected from the group consisting of aryl as defined above, $C_3$-$C_7$-cycloalkyl, halogen (Cl, Br, I, F), $CF_3$, $CF_2CF_3$, —$NH_2$, —$NH(C_1$-$C_4$-alkyl), —$OR^4$ —$N(C_1$-$C_4$-alkyl)_2$, —$NH$—$SO_2R^4$, —$COOR^4$, and —$SO_2NHR^9$,
 (c) heteroaryl as defined hereinabove,
 (d) $C_3$-$C_7$-cycloalkyl,
 (e) perfluoro-$C_1$-$C_4$-alkyl, or
 (f) H;

$R^{7a}$ and $R^{7b}$ are independently
 (a) H,
 (b) straight chain or branched $C_1$-$C_6$-alkyl, $C_2$-$C_6$-alkenyl or $C_2$-$C_6$-alkynyl,
 (c) halogen (Cl, Br, I, F),
 (d) $CF_3$, or (e) when $R^{7a}$ and $R^{7b}$ are bonded to adjacent carbon atoms, they can be joined to form a phenyl ring;

$R^{8a}$ and $R^{8b}$ are independently
- (a) H,
- (b) $C_1$-$C_6$-alkyl optionally substituted with a substituent selected from the group consisting of —OH, -guanidino, $C_1$-$C_4$-alkoxy, —N($R^4$)$_2$, COOR$^4$, —CON($R^4$)$_2$, —O—COR$^4$, -aryl, -heteroaryl, —S(O)$_x$—R$^{23}$, -tetrazol-5-yl, —CONHSO$_2$R$^{23}$, —SO$_2$NH-heteroaryl, —SO$_2$NHCOR$^{23}$, —PO(OR$^4$)$_2$, —PO(OR$^4$)R$^9$, —SO$_2$NH—CN, —NR$^{10}$COOR$^{23}$, morpholino, —N—($C_1$-$C_6$-alkyl)piperazine, —COR$^4$,

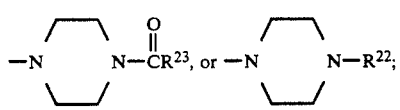

- (c) —CO-aryl,
- (d) —$C_3$-$C_7$-cycloalkyl,
- (e) halogen (Cl, Br, I, F),
- (f) —OH,
- (g) —OR$^{23}$,
- (h) —$C_1$-$C_4$-perfluoroalkyl,
- (i) —S(O)$_x$—R$^{23}$,
- (j) —COOR$^4$,
- (k) —SO$_3$H,
- (l) —NR$^4$R$^{23}$,
- (m) —NR$^{24}$COR$^{23}$,
- (n) —NR$^{24}$COOR$^{23}$,
- (o) —SO$_2$NR$^9$R$^{10}$,
- (p) —NO$_2$,
- (q) —NR$^{24}$SO$_2$R$^{23}$,
- (r) —NR$^{24}$CONR$^4$R$^{23}$,
- (s)

- (t) -aryl or -heteroaryl as defined above,
- (u) —NR$^{24}$SO$_2$CF$_3$,
- (v) —SO$_2$NH-heteroaryl,
- (w) —SO$_2$NHCOR$^{23}$,
- (x) —CONHSO$_2$R$^{23}$,
- (y) —PO(OR$^4$)$_2$,
- (z) —PO(OR$^4$)R$^9$,
- (aa) -tetrazol-5-yl,
- (bb) —CONH(tetrazol-5-yl),
- (cc) —COR$^4$,
- (dd) —SO$_2$NHCN
- (ff) —CO-heteroaryl,
- (gg) —NR$^{24}$SO$_2$NR$^{23}$R$^9$,
- (hh)

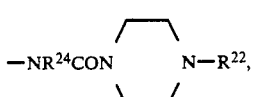

(ii)

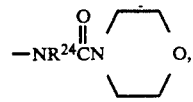

(jj)

(kk)

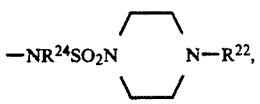

(ll)

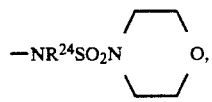

(mm)

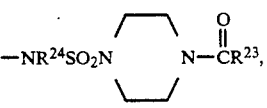

(nn)

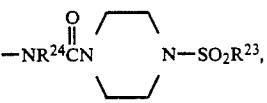

or
(oo)

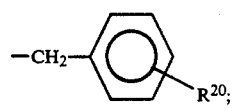

$R^9$ is H, $C_1$-$C_5$-alkyl, aryl or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxyalkyl, or

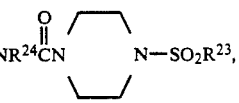

$R^{12}$ is —CN, —NO$_2$, —CF$_3$ or —CO$_2$R$^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;

$R^{16}$ is H, $C_1$-$C_6$-alkyl, $C_3$-$C_6$-cycloalkyl, aryl or arylmethyl;

$R^{17}$ is —$NR^9R^{10}$, —$OR^{10}$, —$NHCONH_2$, —$NHCSNH_2$,

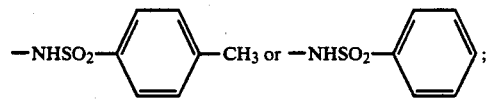

$R^{18}$ and $R^{19}$ are independently $C_1$-$C_4$-alkyl or taken together are —$(CH_2)_q$- where q is 2 or 3;

$R^{20}$ is H, —$NO_2$, —$NH_2$, —OH or —$OCH_3$;

$R^{21}$ is H, aryl, or $C_1$-$C_4$-alkyl optionally substituted with aryl, —$NH_2$, —$NH(C_1$-$C_4$-alkyl), —$N(C_1$-$C_4$-alkyl$)_2$, —$CO_2R^4$, —OH, —$SO_3H$, or —$SO_2NH_2$;

$R^{22}$ is
   (a) aryl as defined above,
   (b) heteroaryl as defined above, or
   (c) $C_1$-$C_4$-alkyl optionally substituted with a substituent selected from the group consisting of aryl as defined above, heteroaryl as defined above, —OH, —$NH_2$, —$NH(C_1$-$C_4$-alkyl), —$N(C_1$-$C_4$-alkyl$)_2$, —$CO_2R^4$, halogen (Cl, Br, F, I), and —$CF_3$;

$R^{23}$ is
   (a) aryl as defined above,
   (b) heteroaryl as defined above,
   (c) $C_3$-$C_7$-cycloalkyl,
   (d) $C_1$-$C_6$-alkyl optionally substituted with a substituent selected from the group consisting of aryl as defined above, heteroaryl as defined above, —OH, —SH, $C_1$-$C_4$-alkyl, —$O(C_1$-$C_4$-alkyl), $C_3$-$C_7$-cycloalkyl, —$S(O)_x(C_1$-$C_4$-alkyl), —$CF_3$, halogen (Cl, Br, F, I), —$NO_2$, —$CO_2H$, $CO_2$—$C_1$-$C_4$-alkyl, —$NH_2$, —$NH(C_1$-$C_4$-alkyl), —$N(C_1$-$C_4$-alkyl$)_2$, —$PO_3H_2$, —PO(OH)(O—$C_1$-$C_4$-alkyl), —$N(C_1$-$C_4$-alkyl)$COR^{4a}$, —$CON(C_1$-$C_4$-alkyl$)_2$, or —$PO(OR^4)R^9$,
   (e) perfluoro-$C_1$-$C_4$-alkyl, or
   (f) CH(aryl)$_2$;

$R^{24}$ is
   (a) $C_1$-$C_6$ alkyl,
   (b) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, $C_1$-$C_4$ alkylthio, $C_1$-$C_4$ alkylsulfinyl or $C_1$-$C_4$ alkyl sulfonyl,
   (c) $C_2$-$C_6$ alkenyl,
   (d) phenyl $C_1$-$C_6$ alkyl,
   (e) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-$C_4$ alkyl)amino, $CF_3$, phenyl $C_1$-$C_4$ alkoxy, $C_1$-$C_4$ alkylthio, $C_1$-$C_4$ alkylsulfinyl, or $C_1$-$C_4$ alkylsulfonyl,
   (f) heteroaryl $C_1$-$C_6$ alkyl,
   (g) substituted heteroaryl $C_1$-$C_6$ alkyl, in which the substituent on the heteroaryl group is F, Cl, $NO_2$, $CO_2R^2$, or di-($C_1$-$C_4$ alkyl)amino, and
   (h) H;

$R^{25}$ is
   (a) H,
   (b) aryl as defined above, or
   (c) $C_1$-$C_6$-alkyl optionally substituted with aryl, F, Cl, Br, —OH, —$NH_2$, —$NH(C_1$-$C_4$-alkyl), —$N(C_1$-$C_4$-alkyl$)_2$, or $CF_3$;

$R^{26}$ is
   (a) aryl as defined above,
   (b) $C_1$-$C_6$-alkyl optionally substituted with aryl, F, Cl, Br, —OH, —$NH_2$, —$NH(C_1$-$C_4$-alkyl), —$N(C_1$-$C_4$-alkyl$)_2$, $CF_3$, —$COOR^4$, or CN,
   (c) —$OCH(R^4)$—O—CO—$R^{4a}$, or
   (d) —OH or —O—$C_1$-$C_6$-alkyl wherein alkyl is as defined in (b);

$R^{27}$ is
   (a) H,
   (b) $C_1$-$C_6$-alkyl optionally substituted with aryl, F, Cl, Br, —OH, —$NH_2$, —$NH(C_1$-$C_4$-alkyl), —$N(C_1$-$C_4$-alkyl$)_2$, $CF_3$, —$COOR^4$, or CN, or
   (c) F, Cl, Br;

X is
   (a) a carbon-carbon single bond,
   (b) —CO—,
   (c) —O—,
   (d) —S—,
   (e) 
   (f) 
   (g) 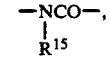
   (h) —$OCH_2$—,
   (i) —$CH_2O$—,
   (j) —$SCH_2$—,
   (k) —$CH_2S$—,
   (l) —$NHC(R^9)(R^{10})$,
   (m) —$NR^9SO_2$—,
   (n) —$SO_2NR^9$—,
   (o) —$C(R^9)(R^{10})NH$—,
   (p) —CH=CH—,
   (q) —CF=CF—,
   (r) —CH=CF—,
   (s) —CF=CH—,
   (t) —$CH_2CH_2$—,
   (u) —$CF_2CF_2$—,
   (v) 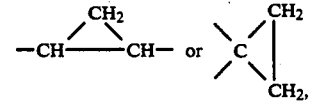
   (w)
   (x) 

(y)

or (z)

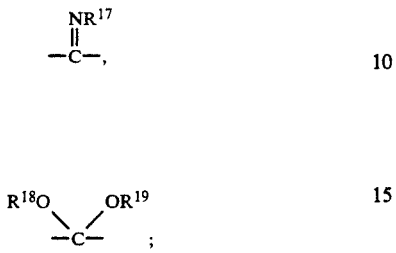

n is 1 to 3;
r is 1 or 2; and
x is 0 to 2.

2. The compound according to claim 1 wherein:
K is —C(O)—;
J and L are connected together to form a 6 carbon aromatic ring substituted with $R^{7a}$, $R^{7b}$, $R^{8a}$ and $R^{8b}$;
$R^1$ is —$SO_2NHCO_2R^{23}$;
X is a single bond;
$R^{2a}$ is H;
$R^{2b}$ is H, F, Cl, $CF_3$, $C_1$-$C_6$-alkyl, $C_2$-$C_4$-alkenyl, or $C_2$-$C_4$-alkynyl;
$R^{3a}$ is H;
$R^{3b}$ is H, F, Cl, $CF_3$, $C_1$-$C_4$-alkyl, $C_2$-$C_4$-alkenyl, $C_2$-$C_4$-alkynyl, $C_5$-$C_6$-cycloalkyl, —$COOCH_3$, —$COOC_2H_5$, —$SO_2$-$CH_3$, $NH_2$, —$N(C_1$-$C_4$-alkyl)$_2$ or —NH—$SO_2CH_3$;
E is a single bond, —O— or —S—;
$R^6$ is
(a) $C_1$-$C_5$ alkyl optionally substituted with a substituent selected from the group consisting of $C_3$-$C_5$-cycloalkyl, Cl, $CF_3$, $CCl_3$, —O—$CH_3$, —$OC_2H_5$, —S—$CH_3$, —S—$C_2H_5$, phenyl, or F,
(b) $C_2$-$C_5$-alkenyl or $C_2$-$C_5$-alkynyl, or,
(c) $C_3$-$C_5$-cycloalkyl;
$R^{7a}$ and $R^{7b}$ are each H;
$R^{8a}$ and $R^{8b}$ are independently
(a) H,
(b) $C_1$-$C_4$-alkyl optionally substituted with $COOR^4$, $OCOR^{4a}$, OH, aryl, heteroaryl, morpholinyl,

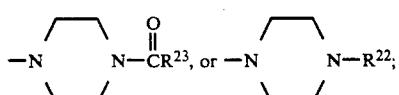

(c) $C_2$-$C_4$-alkenyl,
(d) —OH,
(e) —$NO_2$,
(f) —$NR^{24}COR^{23}$,
(g) —$C_1$-$C_4$-alkoxy,
(h) —$NR^{24}CO_2R^{23}$,
(i) —$NR^4R^{23}$,
(j) halogen (Cl, F, Br),
(k) —$CF_3$,
(l) —$CO_2R^4$,
(m) —CO—aryl as defined above,
(n) heteroaryl,
(o) —$S(O)_x$—$C_1$-$C_4$-alkyl,
(p) —$SO_2$—NH—$C_1$-$C_4$-alkyl,
(q) —$SO_2$—NH-aryl as defined above,
(r) —$NR^{24}SO_2CH_3$,
(s) aryl as defined above,
(t) —$NR^{24}CONR^4R^{23}$, (u)

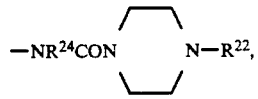

(v)

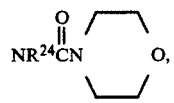

(w)

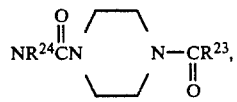

or
(x)

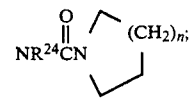

X is a single bond;
r is one; and
x is 0 to 2.

3. The compound according to claim 2 wherein:
$R^1$ is: —$SO_2NHCO_2R^{23}$; and
X is a single bond;
E is a single bond;
r is one;
x is 0 to 2;
$R^{2a}$, $R^{2b}$, $R^{3a}$ and $R^{3b}$ are each H, —$C_1$-$C_6$-alkyl, —$C_2$-$C_4$-alkynyl, —Cl, —F, —$NO_2$, or —$CF_3$;
$R^6$ is methyl, ethyl, -n-propyl, isopropyl, -n-butyl, -trans-2-butenyl, $CH_2CH_2CF_3$, —$CH_2CH_2CH_2CF_3$, -cyclopropyl, or -cyclopropylmethyl;
$R^{8a}$ and $R^{8b}$ are each independently H, —$NO_2$, —$C_1$-$C_4$-alkyl, —$NHR^4$, —$NR^{24}CO$-$R^{23}$, —$S(O)_x$-($C_1$-$C_4$-alkyl), —$N(CH_3)_2$, —$OCH_3$, —$NR^{24}COCH_2NH_2$, —$NR^{24}COCH_2N(CH_3)_2$, —COOH, —$COOCH_3$, —$CH_2OCOCH_3$, Cl, —$CH_2COOCH_3$, —$NR^{24}CON(R^4)_2$, —$NR^{24}CON$-furoyl, —$NR^{24}CO_2R^4$, —$CH_2COOH$, $CH_2OH$, aryl, heteroaryl, —$CH_2$-heteroaryl,

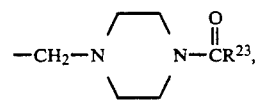

-continued

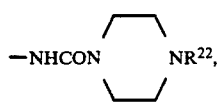

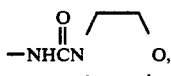

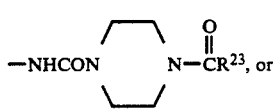

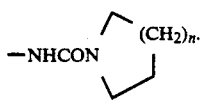

4. The compound according to claim 3 wherein:

$R^1$ is $-SO_2NHCO_2R^{23}$;

X is a single bond;

$R^{2a}$, $R^{2b}$, $R^{3a}$ and $R^{3b}$ are each H, $-C_1-C_4$-alkyl, $-Cl$ or F;

$R^6$ is methyl, ethyl, -n-propyl, isopropyl, -n-butyl, -trans-2-butenyl, $CH_2CH_2CF_3$, $-CH_2CH_2CH_2CF_3$, -cyclopropyl, or -cyclopropylmethyl;

$R^{8a}$ and $R^{8b}$ are each independently H, $-NO_2$, $-C_1-C_4$-alkyl, $-NHR^4$, $-NR^{24}CO-R^{23}$, $-S(O)_x$-$(C_1-C_4$-alkyl), $-N(CH_3)_2$, $-OCH_3$, $-NR^2$-$^4COCH_2NH_2$, $-NR^{24}CON$-furoyl, $-NR^2$-$^4COCH_2N(CH_3)_2$, $-COOH$, $-COOCH_3$, $-CH_2OCOCH_3$, Cl, $-CH_2COOCH_3$, $-NR^2$-$^4CON(R^4)_2$, $-NR^{24}CO_2R^4$, $-CH_2COOH$, $CH_2OH$, aryl, heteroaryl, $-CH_2$-heteroaryl,

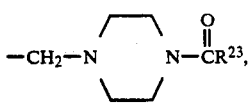

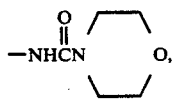

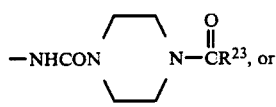

5. The compound according to claim 4 which is

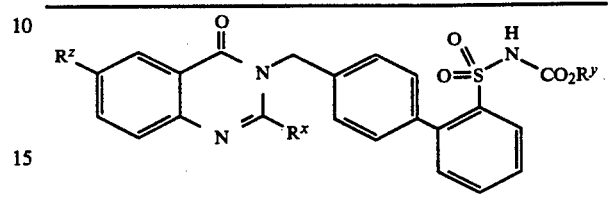

wherein:

| $R^x$ | $R^y$ | $R^z$ |
|---|---|---|
| Pr | butyl | $NO_2-$ |
| Pr | butyl | $NH_2-$ |
| Pr | butyl | BuNHCONH— |
| Pr | butyl | EtNHCONH— |
| Pr | 2-dimethyaminoethyl | EtNHCONH— |
| Bu | butyl | iPrN(Me)CONH— |
| Pr | butyl | iPrNHCONH— |
| Pr | propyl | iPrNHCONH— |
| Pr | pentyl | iPrNHCONH— |
| Pr | butyl | MeNHCONH— |
| Pr | 3-methylbutyl | EtNHCONH— |
| Pr | 3-methylbutyl | MeNHCONH— |
| Pr | butyl | n-PrNHCONH— |
| Pr | 2-cyclopropylethyl | EtNHCONH— |
| Pr | 3,3-dimethylbutyl | EtNHCONH— |
| Bu | pentyl | iPrNHCONH— |
| Bu | butyl | iPrNHCONH— |
| Bu | 2-methoxyethyl | iPrNHCONH— |
| Et | 3-methylbutyl | EtNHCONH— |
| Bu | 2-cyclopropylethyl | morpholinylCONH— |
| Bu | 3-methylbutyl | EtNHCONH— |
| Et | 2-cyclopropylethyl | EtNHCONH— |
| Pr | 2-cyclopentylmethyl | EtNHCONH— |
| Bu | 2-methoxyethyl | EtNHCONH— |
| Pr | Butyl | 2-pyridyl- |
| Pr | Butyl | 3-pyridyl- |
| Pr | Butyl | 4-Me—Ph— |
| Pr | Butyl | methyl(piperazinyl-N-acetyl) |
| Pr | Butyl | methyl(piperazinyl-N-cyclopropylcarbonyl) |
| Pr | Butyl | -methyl(N1-imidazolyl) |
| Pr | benzyl | EtNHCONH— |
| Pr | 2-methoxybenzyl | EtNHCONH— |
| Bu | butyl | EtNHCONH— |
| Pr | ethoxyethyl | EtNHCONH— |
| Pr | benzyl | nPrNHCONH— |
| Pr | 3-methylbutylyl | 2-pyridyl |
| Pr | 3-methylbutyl | 2-furoyl-CONH— or |
| Et | benzyl | EtNHCONH—. |

6. A pharmaceutical composition useful in the treatment of hypertension which comprises a pharmaceutically acceptable carrier and a pharmaceutically effective amount of a compound of claim 1.

7. A method of treating hypertension which comprises administering to a patient in need of such treatment a pharmaceutically effective amount of a compound of claim 1.

8. An ophthalmological formulation for the treatment of ocular hypertension comprising an ophthalmologically acceptable carrier and an effective ocular antihypertensive amount of a compound of claim 1.

9. A method of treating ocular hypertension comprising administering to a patient in need of such treatment an effective ocular antihypertensive amount of a compound of claim 1.

* * * * *